United States Patent
Choi et al.

(10) Patent No.: US 12,137,610 B2
(45) Date of Patent: Nov. 5, 2024

(54) NEAR-INFRARED ABSORBERS, NEAR-INFRARED ABSORBING/BLOCKING FILMS, PHOTOELECTRIC DEVICES, ORGANIC SENSORS, AND ELECTRONIC DEVICES

(71) Applicant: Samsung Electronics Co., Ltd., Suwon-si (KR)

(72) Inventors: Hyesung Choi, Seoul (KR); Ohkyu Kwon, Seoul (KR); Hwang Suk Kim, Suwon-si (KR); Kwang Hee Lee, Hwaseong-si (KR); Dong-Seok Leem, Seongnam-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 912 days.

(21) Appl. No.: 16/953,991

(22) Filed: Nov. 20, 2020

(65) Prior Publication Data

US 2021/0159423 A1  May 27, 2021

(30) Foreign Application Priority Data

Nov. 22, 2019 (KR) .................. 10-2019-0151737
Nov. 25, 2019 (KR) .................. 10-2019-0152735

(51) Int. Cl.
*H10K 85/60* (2023.01)
*C07D 519/00* (2006.01)
*H10K 30/40* (2023.01)

(52) U.S. Cl.
CPC ......... *H10K 85/657* (2023.02); *C07D 519/00* (2013.01); *H10K 30/40* (2023.02)

(58) Field of Classification Search
CPC ...... H10K 85/657; H10K 30/40; H10K 39/32; H10K 39/10; H10K 85/631; H10K 85/636;

(Continued)

(56) References Cited

U.S. PATENT DOCUMENTS

2015/0311258 A1* 10/2015 Kim .................. H10K 39/32
                                                      257/40
2021/0036251 A1    2/2021 Kim et al.

FOREIGN PATENT DOCUMENTS

CN    106661057 A    5/2017
CN    107459516 A    12/2017
(Continued)

OTHER PUBLICATIONS

Takahiro Kono et al., "Dithienylbenzobis(thiadiazole) based organic semiconductors with low LUMO levels and narrow energy gaps" Chemcomm, published Apr. 13, 2010, 46, 3265-3267.

(Continued)

*Primary Examiner* — Michael Y Sun
(74) *Attorney, Agent, or Firm* — Harness, Dickey & Pierce, P.L.C.

(57) ABSTRACT

A near-infrared absorber includes a compound represented by Chemical Formula 1. A near-infrared absorbing/blocking film, a photoelectric device, an organic sensor, and an electronic device may include the near-infrared absorber.

[Chemical Formula 1]

(Continued)

In Chemical Formula 1, Ar, $Ar^1$, $Ar^2$, $Ar^3$, $Ar^4$, $X^1$, $X^2$, $L^1$, $L^2$, $R^1$, and $R^2$ are the same as defined in the detailed description.

48 Claims, 14 Drawing Sheets

(58) Field of Classification Search
CPC .... H10K 85/655; H10K 30/00; C07D 519/00; C07D 513/04; Y02E 10/52; Y02E 10/549; C07F 11/005; C08K 5/46; G02B 5/208; H01L 31/022441; H01L 31/0543
See application file for complete search history.

(56) References Cited

FOREIGN PATENT DOCUMENTS

| EP | 3252051 A1 | 12/2017 |
|---|---|---|
| EP | 3798270 A1 | 3/2021 |
| JP | 2018-111673 A | 7/2018 |
| JP | 2018111675 A * | 7/2018 |
| KR | 1020190078963 A * | 7/2019 |

OTHER PUBLICATIONS

Gang Qian et al., "Simple and Efficient Near-Infrared Organic Chromophores for Light-Emitting Diodes with Single Electroluminescent Emission above 1000nm" Adv. Matter, 2009, 21, 111-116.

Yongwoo Shin et al., "Deliberate Charge Conjugation Symmetry Breaking for Π-Conjugated Electron Acceptor Design", The Journal of Physical Chemistry, 119.23, pp. 12808-12814, DOI: 10.1021/acs.jpcc.5b01340.

Yanbing Zhang, et al., "Near-Infrared Fluorescent Thienothiadiazole Dyes with Large Strokes Shifts and High Photostability", The Journal of Organic Chemistry, 82, pp. 5597-5606, 2017, DOI: 10.1021/acs.joc.7b00422.

Ji Qi et al., "Highly Stable Organic Small Molecular Nanoparticles as an Advanced and Bicompatible Phototheranostic Agent of Tumor in Living Mice", ACS Nano, vol. 11, No. 7, pp. 7177-7188, 2017, DOI: 10.1021/acs.nano.7b03062.

Yi Liu et al., "Toward Benzobis(thiadiazole)-based Diradicaloids", Chemistry—an Asian Journal, Extended Aromatic Structures, vol. 12, No. 17, pp. 2177-2182, 2017, DOI: 10.1002/asia.201700732.

Anup Thomas et al., "Comparative Study of the Semiconducting Properties of Benzothiadiazole and Benzobis(thiadiazole) Derivatives Using Computational Techniques", Articles, ChemPhysChem, vol. 13, No. 2, pp. 597-605, 2012, DOI: 10.1002/cphc.201100565.

Gang Qian et al., "Synthesis and Application of Thiadiazoloquinoxaline-Containing Chromophores as Dopants for Efficient Near-Infrared Organic Light-Emitting Diodes", J. Phys. Chem., vol. 113, No. 4, pp. 1589-1595, 2009, DOI: 10.1021/jp809568a.

Minquan Tian et al., "Search for Squaraine Derivatives That Can Be Sublimed without Thermal Decomposition", J. Phys. Chem. B., vol. 106, No. 17, pp. 4370-4376, 2002, DOI: 10.1021/jp013698r.

Bogyu Lim et al., "Ternary Bulk Heterojunction Solar Cells: Addition of Soluble NIR Dyes for Photocurrent Generation beyond 800 nm", ACS Applied Materials & Interfaces, 6, pp. 6905-6913, 2014, dx.doi.org/10.1021/am5007172.

Kohsuke Kawabata et al., "Very Small Bandgap Π-Conjugated Polymers with Extended Thienoquinoids", Journal of the American Chemical Society, 138, pp. 7725-7732, 2016, DOI: 10.1021/jacs.6b03688.

Extended European Search Report dated Apr. 22, 2021, issued in corresponding European Patent Application No. 20209044.5.

Office Action for Chinese Application No. 202011324156.7 dated Feb. 19, 2024 and English translation.

* cited by examiner

NEAR-INFRARED ABSORBERS, NEAR-INFRARED ABSORBING/BLOCKING FILMS, PHOTOELECTRIC DEVICES, ORGANIC SENSORS, AND ELECTRONIC DEVICES

CROSS-REFERENCE TO RELATED APPLICATIONS

This application claims priority to and the benefit of, under 35 U.S.C. § 119, Korean Patent Application No. 10-2019-0151737 filed in the Korean Intellectual Property Office on Nov. 22, 2019, and Korean Patent Application No. 10-2019-0152735 filed in the Korean Intellectual Property Office on Nov. 25, 2019, the entire contents of each of which are incorporated herein by reference.

BACKGROUND

1. Field

A near-infrared (NIR) absorber, a near-infrared absorbing/blocking film, a photoelectric device, an organic sensor, and an electronic device are disclosed.

2. Description of the Related Art

An imaging device is used in a digital camera and a camcorder, etc., to capture an image and to store it as an electrical signal, and the imaging device includes a sensor separating incident light according to a wavelength and converting each component to an electrical signal.

Recently, photoelectric devices in the near-infrared region for improving sensitivity of a sensor in a low-illumination environment or for use as a biometric device have been studied.

SUMMARY

Some example embodiments provide a near-infrared absorber having improved near-infrared light absorption characteristics.

Some example embodiments provide a film including the near-infrared absorber.

Some example embodiments provide a photoelectric device including the near-infrared absorber.

Some example embodiments provide an organic sensor including the near-infrared absorber or the photoelectric device.

Some example embodiments provide an electronic device including the photoelectric device or the organic sensor.

According to some example embodiments, a near-infrared absorber including a compound represented by Chemical Formula 1 is provided.

[Chemical Formula 1]

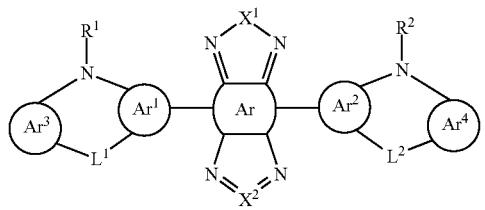

In Chemical Formula 1,

Ar is a substituted or unsubstituted C6 to C30 aromatic ring, a substituted or unsubstituted C3 to C30 heteroaromatic ring, or a combination thereof, $X^1$ is O, S, Se, Te, S(=O), S(=$O_2$), $NR^a$, $CR^bR^c$, $SiR^dR^e$, $GeR^fR^g$, $CR^hCR^i$, or $CR^{hh}$=$CR^{ii}$ (wherein $R^a$, $R^b$, $R^c$, $R^d$, $R^e$, $R^f$, $R^g$, $R^h$, and $R^i$ are independently hydrogen, deuterium, a C1 to C30 alkyl group, a C1 to C30 haloalkyl group, a C6 to C30 aryl group, a C6 to C30 aryloxy group, a C3 to C30 heteroaryl group, a halogen, a cyano group, or a combination thereof, $R^{hh}$ and $R^{ii}$ are independently $(CH)_w$ where w is a positive integer or at least one heteroatom of O, N, S, Se, or Te, and $R^{hh}$ and $R^{ii}$ are linked to each other to form an aromatic ring or a heteroaromatic ring), $X^2$ is O, S, Se, Te, C, $CR^x$—$CR^y$, $CR^{xx}$—$CR^{yy}$, S(=O), or S(=$O_2$) (wherein $R^x$ and $R^y$ are independently hydrogen, deuterium, a C1 to C30 alkyl group, a C1 to C30 haloalkyl group, a C6 to C30 aryl group, a C6 to C30 aryloxy group, a C3 to C30 heteroaryl group, a halogen, a cyano group, or a combination thereof, $R^{xx}$ and $R^{yy}$ are independently $(CH)_v$ where v is a positive integer or at least one heteroatom of O, N, S, Se, or Te, and $R^{xx}$ and $R^{yy}$ are linked to each other to form an aromatic ring or a heteroaromatic ring), $Ar^1$ and $Ar^2$ are independently a heteroarene group including at least one heteroatom of O, S, Se, or Te, $Ar^3$ and $Ar^4$ are independently a substituted or unsubstituted C6 to C30 arene group, a substituted or unsubstituted C3 to C30 heteroarene group, or a condensed ring group thereof, $R^1$ and $R^2$ are independently hydrogen, deuterium, a halogen, a cyano group, a nitro group, a hydroxyl group, a substituted or unsubstituted C1 to C10 alkyl group, a substituted or unsubstituted C1 to C10 alkoxy group, a substituted or unsubstituted C6 to C10 aryl group, or a substituted or unsubstituted C3 to C10 heteroaryl group, and $L^1$ and $L^2$ are independently a single bond, —O—, —S—, —Se—, —Te—, —N=, —$NR^a$—, —$SiR^bR^c$—, —$GeR^dR^e$—, —$(CR^fR^g)_n$—, or —$(C(R^h)=C(R^i))$— (wherein $R^a$, $R^b$, $R^c$, $R^d$, $R^e$, $R^f$, $R^g$, $R^h$, and $R^i$ are independently hydrogen, deuterium, a halogen, a cyano group, a substituted or unsubstituted C1 to C10 alkyl group, or a substituted or unsubstituted C6 to C10 aryl group, wherein $R^b$ and $R^c$, $R^d$ and $R^e$, $R^f$ and $R^g$, or $R^h$ and $R^i$ are independently present or are linked to each other to form a separate ring, and n of —$(CR^fR^g)_n$— is an integer of 1 or 2).

In Chemical Formula 1, Ar may be benzene ring, a substituted or unsubstituted naphthalene ring, a substituted or unsubstituted anthracene ring, a substituted or unsubstituted phenanthrene ring, a substituted or unsubstituted tetracene ring, or a substituted or unsubstituted pyrene ring.

In Chemical Formula 1, Ar may be a substituted or unsubstituted quinoline ring, a substituted or unsubstituted isoquinoline ring, a substituted or unsubstituted quinoxaline ring, a substituted or unsubstituted quinazoline ring, or a substituted or unsubstituted phenanthroline ring.

In Chemical Formula 1, Ar may be one moiety of a set of moieties represented by Chemical Formula A-1, each moiety including at least one aromatic ring and left and right linking groups.

[Chemical Formula A-1]

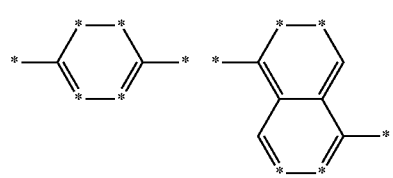

-continued

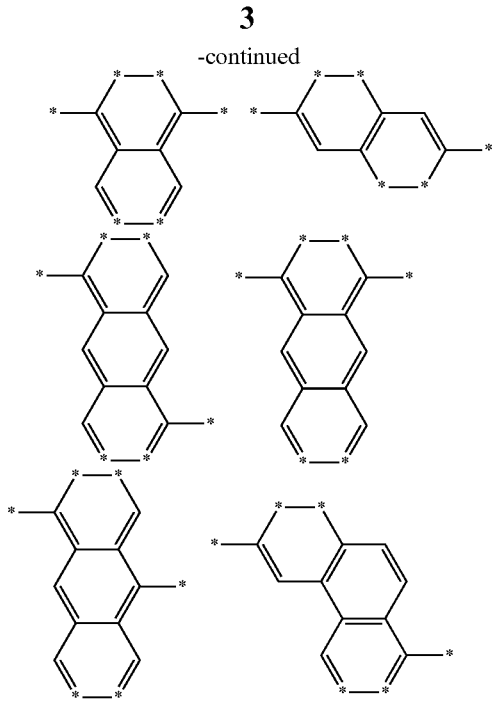

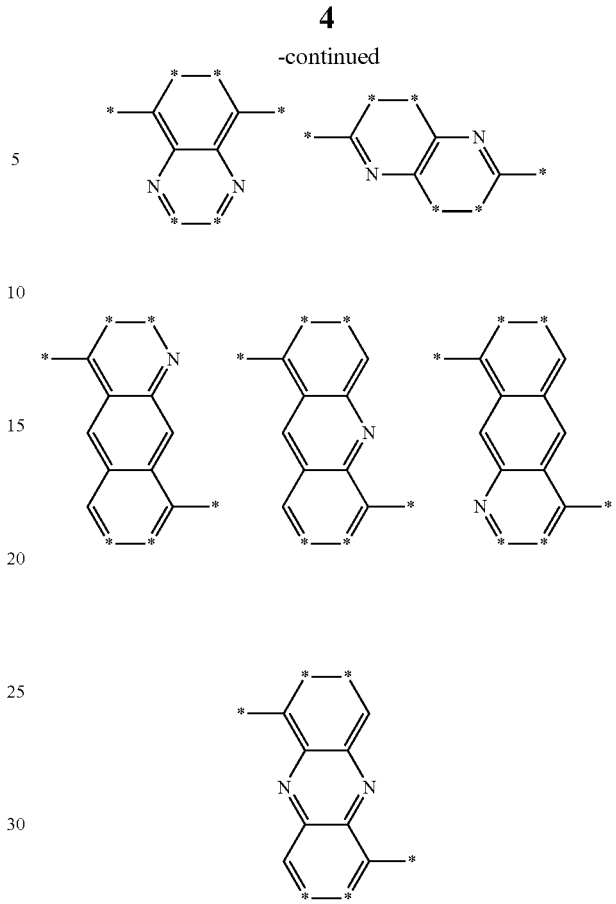

In Chemical Formula A-1, hydrogen of each aromatic ring may be replaced by a halogen, a cyano group, a C1 to C10 alkyl group, a C1 to C10 alkoxy group, a C1 to C10 haloalkyl group, a silyl group, or a C1 to C10 alkylsilyl group, separate adjacent pairs of *'s inside the at least one aromatic ring are linking portions with separate, respective ones of an N—$X^1$—N-containing ring of Chemical Formula 1 or —N=$X^2$=N-containing ring of Chemical Formula 1, and

*'s of the left and right linking groups are portions linked to separate, respective ones of $Ar^1$ or $Ar^2$ of Chemical Formula 1.

In Chemical Formula 1, Ar may be one moiety of a set of moieties represented by Chemical Formula A-2, each moiety including at least one aromatic ring and left and right linking groups.

[Chemical Formula A-2]

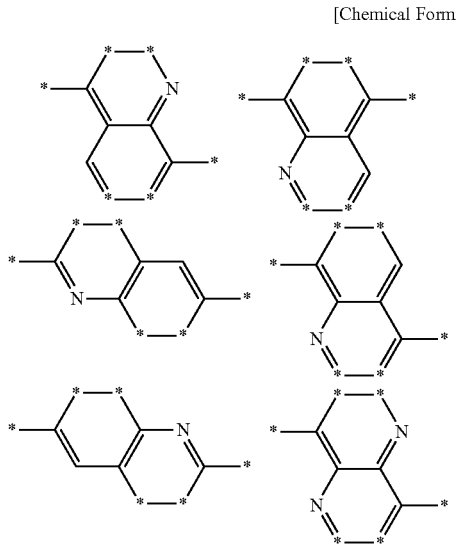

In Chemical Formula A-2, hydrogen of each aromatic ring may be replaced by a halogen, a cyano group, a C1 to C10 alkyl group, a C1 to C10 alkoxy group, a C1 to C10 haloalkyl group, —$SiH_3$, or a C1 to C10 alkylsilyl group, separate adjacent pairs of *'s inside the at least one aromatic ring are linking portions with separate, respective ones of an N—$X^1$—N-containing ring of Chemical Formula 1 and —N=$X^2$=N-containing ring of Chemical Formula 1, and

*'s of the left and right linking groups are portions linked to separate, respective ones of $Ar^1$ and $Ar^2$ of Chemical Formula 1.

In Chemical Formula 1, when $X^2$ is $CR^{xx}$—$CR^{yy}$, the aromatic ring formed by linking $R^{xx}$ with $R^{yy}$ may be a substituted or unsubstituted benzene ring, a substituted or unsubstituted naphthalene ring, a substituted or unsubstituted acenaphthene ring, a substituted or unsubstituted anthracene ring, a substituted or unsubstituted phenanthrene ring, a substituted or unsubstituted tetracene ring or a substituted or unsubstituted pyrene ring; or a substituted or unsubstituted quinoline ring, a substituted or unsubstituted isoquinoline ring, a substituted or unsubstituted quinoxaline ring, a substituted or unsubstituted quinazoline ring, a substituted or unsubstituted phenanthroline ring, a substituted or unsubstituted pyrimidine ring, or a substituted or unsubstituted benzodithiophene ring.

In Chemical Formula 1, when $X^2$ is $CR^{xx}$—$CR^{yy}$, the aromatic ring formed by linking $R^{xx}$ with $R^{yy}$ may be one moiety of a set of moieties represented by Chemical Formula B-1, each moiety including at least one aromatic ring.

[Chemical Formula B-1]

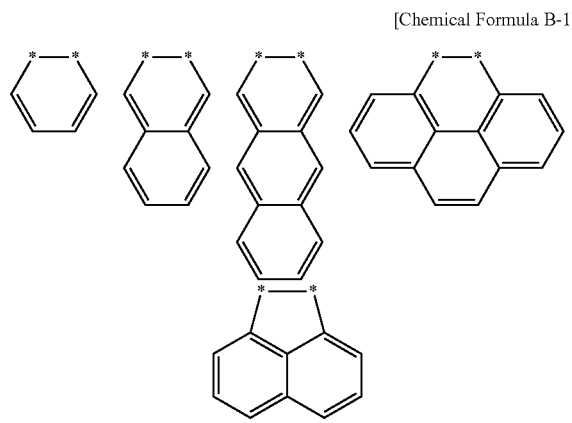

In Chemical Formula B-1, hydrogen of each aromatic ring may be replaced by a halogen, a cyano group, a C1 to C30 alkyl group, a C1 to C30 alkoxy group, a C1 to C30 haloalkyl group, —SiH$_3$, a C1 to C30 alkylsilyl group, a C6 to C30 aryl group, a C6 to C30 aryloxy group, or a C3 to C30 heteroaryl group, and

*'s inside the at least one aromatic ring are linking portions with a carbon of CR$^{xx}$—CR$^{yy}$.

In Chemical Formula 1, when X$^2$ is CR$^{xx}$—CR$^{yy}$, the aromatic ring formed by linking R$^{xx}$ with R$^{yy}$ may be one moiety of a set of moieties represented by Chemical Formula B-2, each moiety including at least one aromatic ring.

[Chemical Formula B-2]

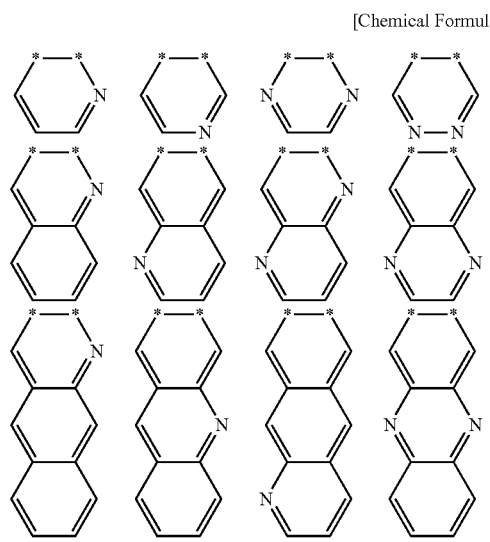

In Chemical Formula B-2, hydrogen of each aromatic ring may be replaced by a halogen, a cyano group, a C1 to C30 alkyl group, a C1 to C30 alkoxy group, a C1 to C30 haloalkyl group, —SiH$_3$, a C1 to C30 alkylsilyl group, a C6 to C30 aryl group, a C6 to C30 aryloxy group, or a C3 to C30 heteroaryl group, and

*'s inside the at least one aromatic ring are linking portions with a carbon of CR$^{xx}$—CR$^{yy}$.

In Chemical Formula 1, when X$^2$ is CR$^{xx}$—CR$^{yy}$, the aromatic ring formed by linking R$^{xx}$ with R$^{yy}$ may be one of moieties represented by Chemical Formulas B-3-1 and B-3-2.

[Chemical Formula B-3-1]

[Chemical Formula B-3-2]

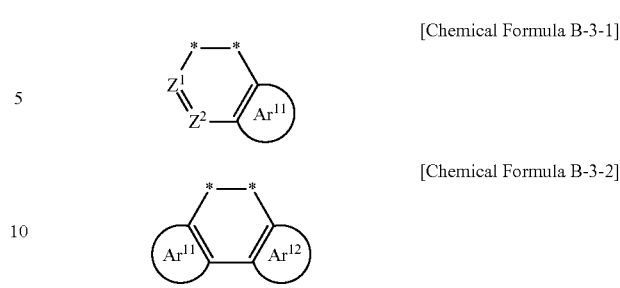

In Chemical Formulas B-3-1 and B-3-2,

Ar$^{11}$ and Ar$^{12}$ are independently a substituted or unsubstituted C6 to C30 arene group or a substituted or unsubstituted C3 to C30 heteroarene group, in Chemical Formula B-3-1, Z$^1$ and Z$^2$ are independently CR$^a$ or N (wherein R$^a$ is hydrogen, deuterium, a C1 to C30 alkyl group, a C1 to C30 haloalkyl group, —SiH$_3$, a C1 to C30 alkylsilyl group, —NH$_2$, a C1 to C30 alkylamine group, a C6 to C30 arylamine group, a C6 to C30 aryl group, C6 to C30 aryloxy group, C3 to C30 heteroaryl group, a halogen, a cyano group, or a combination thereof), hydrogen of each aromatic ring may be replaced by a halogen, a cyano group, a C1 to C30 alkyl group, a C1 to C30 alkoxy group, a C1 to C30 haloalkyl group, —SiH$_3$, a C1 to C30 alkylsilyl group, a C6 to C30 aryl group, a C6 to C30 aryloxy group, or a C3 to C30 heteroaryl group, and

*'s inside the at least one aromatic ring are linking portions with a carbon of CR$^{xx}$—CR$^{yy}$.

The moiety represented by Chemical Formula B-3-1 may be one moiety of a set of moieties represented by Chemical Formula B-3-11, each moiety including at least one aromatic ring.

[Chemical Formula B-3-11]

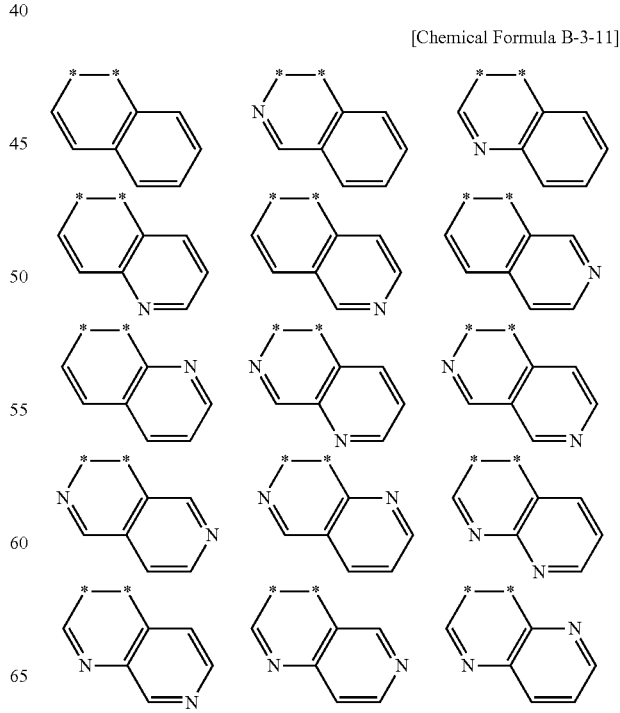

-continued

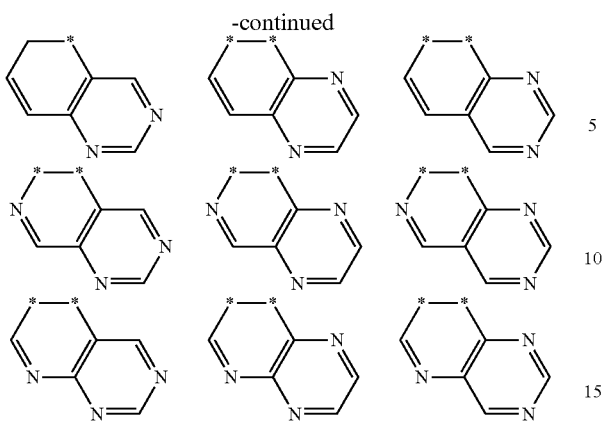

In Chemical Formula B-3-11, hydrogen of each aromatic ring may be replaced by a halogen, a cyano group, a C1 to C30 alkyl group, a C1 to C30 alkoxy group, a C1 to C30 haloalkyl group, —SiH₃, a C1 to C30 alkylsilyl group, a C6 to C30 aryl group, a C6 to C30 aryloxy group, or a C3 to C30 heteroaryl group, and

*'s inside the at least one aromatic ring are linking portions with the carbon of $CR^{xx}$—$CR^{yy}$.

The moiety represented by Chemical Formula B-3-2 may be one moiety of a set of moieties represented by Chemical Formula B-3-21, each moiety including at least one aromatic ring.

[Chemical Formula B-3-21]

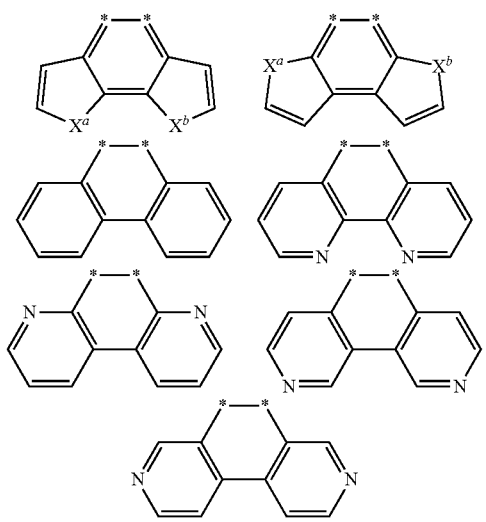

In Chemical Formula B-3-21, hydrogen of each aromatic ring may be replaced by a halogen, a cyano group, a C1 to C30 alkyl group, a C1 to C30 alkoxy group, a C1 to C30 haloalkyl group, —SiH₃, a C1 to C30 alkylsilyl group, a C6 to C30 aryl group, a C6 to C30 aryloxy group, or a C3 to C30 heteroaryl group, $X^a$ and $X^b$ are independently O, S, Se, Te, $NR^a$, $SiR^bR^c$, or $GeR^dR^e$ (wherein $R^a$, $R^b$, $R^c$, $R^d$, and $R^e$ are independently hydrogen, a halogen, a cyano group, a substituted or unsubstituted C1 to C30 alkyl group, a substituted or unsubstituted C1 to C30 alkoxy group, a substituted or unsubstituted C6 to C30 aryl group, or a substituted or unsubstituted C6 to C30 aryloxy group), and

*'s inside the aromatic ring are linking portions with the carbon of $CR^{xx}$—$CR^{yy}$.

In Chemical Formula 1, $Ar^1$ and $Ar^2$ may be the same or different and may be each represented by one of Chemical Formula C-1-1, Chemical Formula C-1-2, or Chemical Formula C-1-3 that each include at least one aromatic ring.

[Chemical Formula C-1-1]

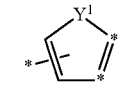

[Chemical Formula C-1-2]

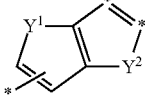

[Chemical Formula C-1-3]

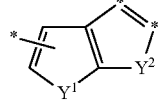

In Chemical Formulas C-1-1 to C-1-3, hydrogen of each aromatic ring may be replaced by a halogen, a cyano group, a C1 to C30 alkyl group, a C1 to C30 alkoxy group, a C1 to C30 haloalkyl group, —SiH₃, a C1 to C30 alkylsilyl group, a C6 to C30 aryl group, a C6 to C30 aryloxy group, or a C3 to C30 heteroaryl group, $Y^1$ is O, S, Se, Te, S(═O), S(═O)₂, $NR^{a1}$, $SiR^{b1}R^{c1}$, or $GeR^{d1}R^{e1}$ (wherein $R^{a1}$, $R^{b1}$, $R^{c1}$, $R^{d1}$, and $R^{e1}$ are independently hydrogen, a C1 to C10 alkyl group, a C1 to C10 haloalkyl group, a C1 to C10 alkoxy group, —SiH₃, a C1 to C10 alkylsilyl group, —NH₃, a C1 to C10 alkylamine group, a C6 to C10 arylamine group, a C6 to C14 aryl group, a C6 to C14 aryloxy group, a C3 to C12 heteroaryl group, a halogen, a cyano group, or a combination thereof), $Y^2$ is O, S, Se, Te, S(═O), S(═O)₂, $NR^{a2}$, $SiR^{b2}R^{c2}$, $GeR^{d2}R^{e2}$, or $CR^{f2}R^{g2}$ (wherein $R^{a2}$, $R^{b2}$, $R^{c2}$, $R^{d2}$, $R^{e2}$, $R^{f2}$, and $R^{g2}$ are independently hydrogen, a C1 to C10 alkyl group, a C1 to C10 haloalkyl group, a C1 to C10 alkoxy group, —SiH₃, a C1 to C10 alkylsilyl group, —NH₃, a C1 to C10 alkylamine group, a C6 to C10 arylamine group, a C6 to C14 aryl group, a C6 to C14 aryloxy group, a C3 to C12 heteroaryl group, a halogen, a cyano group, or a combination thereof), $R^{b1}$ and $R^{c1}$, $R^{d1}$ and $R^{e1}$, $R^{b2}$ and $R^{c2}$, $R^{d2}$ and $R^{e2}$, and $R^{f2}$ and $R^{g2}$ may be independently present or combined with each other to from a spiro ring, an * outside the at least one aromatic ring is a linking point with Ar of Chemical Formula 1, and

*'s inside the at least one aromatic ring are linking portions with an N($R^1$)-containing ring that includes $R^1$ of Chemical Formula 1 and an N($R^2$)-containing ring that includes $R^2$ of Chemical Formula 1.

In Chemical Formula 1, $Ar^1$ and $Ar^2$ are the same or different and may be each represented by one of Chemical Formulas C-2-1 to C-2-4 that each include at least one aromatic ring.

[Chemical Formula C-2-1]

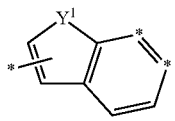

-continued

[Chemical Formula C-2-2]

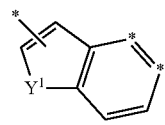

[Chemical Formula C-2-3]

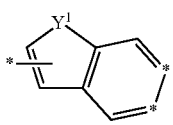

[Chemical Formula C-2-4]

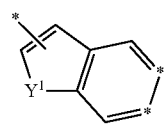

-continued

[Chemical Formula C-3-4]

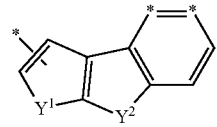

[Chemical Formula C-3-5]

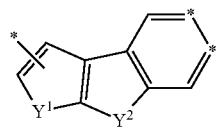

[Chemical Formula C-3-6]

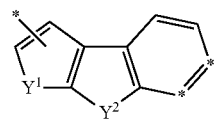

In Chemical Formulas C-2-1 to C-2-4, hydrogen of each aromatic ring may be replaced by a halogen, a cyano group, a C1 to C30 alkyl group, a C1 to C30 alkoxy group, a C1 to C30 haloalkyl group, —SiH$_3$, a C1 to C30 alkylsilyl group, a C6 to C30 aryl group, a C6 to C30 aryloxy group, or a C3 to C30 heteroaryl group, $Y^1$ is O, S, Se, Te, S(═O), S(═O)$_2$, NR$^{a1}$, SiR$^{b1}$R$^{c1}$, or GeR$^{d1}$R$^{e1}$ (wherein R$^{a1}$, R$^{b1}$, R$^{c1}$, R$^{d1}$, and R$^{e1}$ are independently hydrogen, a C1 to C10 alkyl group, a C1 to C10 haloalkyl group, a C1 to C10 alkoxy group, —SiH$_3$, a C1 to C10 alkylsilyl group, —NH$_3$, a C1 to C10 alkylamine group, a C6 to C10 arylamine group, a C6 to C14 aryl group, a C6 to C14 aryloxy group, a C3 to C12 heteroaryl group, a halogen, a cyano group, or a combination thereof), R$^{b1}$ and R$^{c1}$ and R$^{d1}$ and R$^{e1}$ are independently present or combined with each other to from a spiro ring, an * outside the at least one aromatic ring is a linking point with Ar of Chemical Formula 1, and

*'s inside the at least one aromatic ring are linking portions with an N(R$^1$)-containing ring that includes R$^1$ of Chemical Formula 1 and an N(R$^2$)-containing ring that includes R$^2$ of Chemical Formula 1.

In Chemical Formula 1, Ar$^1$ and Ar$^2$ may be the same or different and may be each represented by one of Chemical Formulas C-3-1 to C-3-6 that each include at least one aromatic ring.

[Chemical Formula C-3-1]

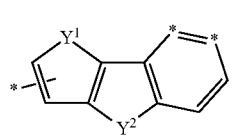

[Chemical Formula C-3-2]

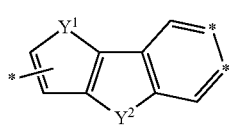

[Chemical Formula C-3-3]

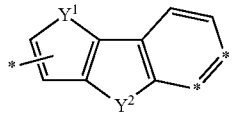

In Chemical Formulas C-3-1 to C-3-6, hydrogen of each aromatic ring may be replaced by a halogen, a cyano group, a C1 to C30 alkyl group, a C1 to C30 alkoxy group, a C1 to C30 haloalkyl group, —SiH$_3$, a C1 to C30 alkylsilyl group, a C6 to C30 aryl group, a C6 to C30 aryloxy group, or a C3 to C30 heteroaryl group, $Y^1$ is O, S, Se, Te, S(═O), S(═O)$_2$, NR$^{a1}$, SiR$^{b1}$R$^{c1}$, or GeR$^{d1}$R$^{e1}$ (wherein R$^{a1}$, R$^{b1}$, R$^{c1}$, R$^{d1}$ and R$^{e1}$ are independently hydrogen, a C1 to C10 alkyl group, a C1 to C10 haloalkyl group, a C1 to C10 alkoxy group, —SiH$_3$, a C1 to C10 alkylsilyl group, —NH$_3$, a C1 to C10 alkylamine group, a C6 to C10 arylamine group, a C6 to C14 aryl group, a C6 to C14 aryloxy group, a C3 to C12 heteroaryl group, a halogen, a cyano group, or a combination thereof), $Y^2$ is O, S, Se, Te, S(═O), S(═O)$_2$, NR$^{a2}$, SiR$^{b2}$R$^{c2}$, GeR$^{d2}$R$^{e2}$, or CR$^{f2}$R$^{g2}$ (wherein R$^{a2}$, R$^{b2}$, R$^{c2}$, R$^{d2}$, R$^{e2}$, R$^{f2}$ and R$^{g2}$ are independently hydrogen, a C1 to C10 alkyl group, a C1 to C10 haloalkyl group, a C1 to C10 alkoxy group, —SiH$_3$, a C1 to C10 alkylsilyl group, —NH$_3$, a C1 to C10 alkylamine group, a C6 to C10 arylamine group, a C6 to C14 aryl group, a C6 to C14 aryloxy group, a C3 to C12 heteroaryl group, a halogen, a cyano group, or a combination thereof), R$^{b1}$ and R$^{c1}$, R$^{d1}$ and R$^{e1}$, R$^{b2}$ and R$^{c2}$, R$^{d2}$ and R$^{e2}$, and R$^{f2}$ and R$^{g2}$ may be independently present or combined with each other to from a spiro ring, an * outside the at least one aromatic ring is a linking point with Ar of Chemical Formula 1, and

*'s inside the at least one aromatic ring are linking portions with an N(R$^1$)-containing ring that includes R$^1$ of Chemical Formula 1 and an N(R$^2$)-containing ring that includes R$^2$ of Chemical Formula 1.

In Chemical Formula 1, Ar$^1$ and Ar$^2$ may be the same or different and may be each represented by one of Chemical Formula C-4-1 or Chemical Formula C-4-2 that each include at least one aromatic ring.

[Chemical Formula C-4-1]

[Chemical Formula C-4-2]

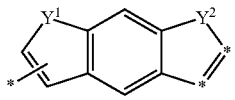

In Chemical Formulas C-4-1 and C-4-2, hydrogen of each aromatic ring may be replaced by a halogen, a cyano group, a C1 to C30 alkyl group, a C1 to C30 alkoxy group, a C1 to C30 haloalkyl group, —SiH$_3$, a C1 to C30 alkylsilyl group, a C6 to C30 aryl group, a C6 to C30 aryloxy group, or a C3 to C30 heteroaryl group, $Y^1$ is O, S, Se, Te, S(=O), S(=O)$_2$, NR$^{a1}$, SiR$^{b1}$R$^{c1}$, or GeR$^{d1}$R$^{e1}$ (wherein R$^{a1}$, R$^{b1}$, R$^{c1}$, R$^{d1}$ and R$^{e1}$ are independently hydrogen, a C1 to C10 alkyl group, a C1 to C10 haloalkyl group, a C1 to C10 alkoxy group, —SiH$_3$, a C1 to C10 alkylsilyl group, —NH$_3$, a C1 to C10 alkylamine group, a C6 to C10 arylamine group, a C6 to C14 aryl group, a C6 to C14 aryloxy group, a C3 to C12 heteroaryl group, a halogen, a cyano group, or a combination thereof), $Y^2$ is O, S, Se, Te, S(=O), S(=O)$_2$, NR$^{a2}$, SiR$^{b2}$R$^{c2}$, GeR$^{d2}$R$^{e2}$, or CR$^{f2}$R$^{g2}$ (wherein R$^{a2}$, R$^{b2}$, R$^{c2}$, R$^{d2}$, R$^{e2}$, R$^{f2}$ and R$^{g2}$ are independently hydrogen, a C1 to C10 alkyl group, a C1 to C10 haloalkyl group, a C1 to C10 alkoxy group, —SiH$_3$, a C1 to C10 alkylsilyl group, —NH$_3$, a C1 to C10 alkylamine group, a C6 to C10 arylamine group, a C6 to C14 aryl group, a C6 to C14 aryloxy group, a C3 to C12 heteroaryl group, a halogen, a cyano group, or a combination thereof), R$^{b1}$ and R$^{c1}$, R$^{d1}$ and R$^{e1}$, R$^{b2}$ and R$^{c2}$, R$^{d2}$ and R$^{e2}$, and R$^{f2}$ and R$^{g2}$ may be independently present or combined with each other to from a spiro ring, an * outside the at least one aromatic ring is a linking point with Ar of Chemical Formula 1, and

*'s inside the aromatic ring are linking portions with an N(R$^1$)-containing ring that includes R$^1$ of Chemical Formula 1 and an N(R$^2$)-containing ring that includes R$^2$ of Chemical Formula 1.

In Chemical Formula 1, Ar$^1$ and Ar$^2$ may be the same or different and may be each represented by one of Chemical Formulas C-5-1 to C-5-8 that each include at least one aromatic ring.

[Chemical Formula C-5-1]

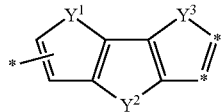

[Chemical Formula C-5-2]

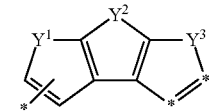

[Chemical Formula C-5-3]

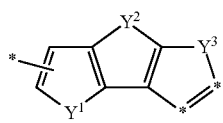

[Chemical Formula C-5-4]

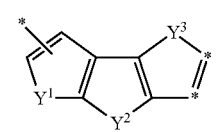

[Chemical Formula C-5-5]

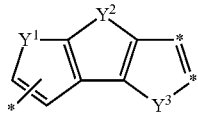

[Chemical Formula C-5-6]

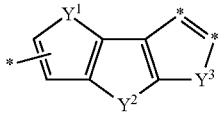

[Chemical Formula C-5-7]

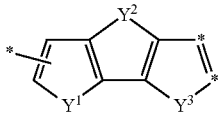

[Chemical Formula C-5-8]

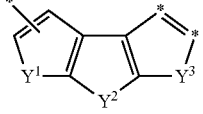

In Chemical Formulas C-5-1 to C-5-8, hydrogen of each aromatic ring may be replaced by a halogen, a cyano group, a C1 to C30 alkyl group, a C1 to C30 alkoxy group, a C1 to C30 haloalkyl group, —SiH$_3$, a C1 to C30 alkylsilyl group, a C6 to C30 aryl group, a C6 to C30 aryloxy group, or a C3 to C30 heteroaryl group, $Y^1$ is O, S, Se, Te, S(=O), S(=O)$_2$, NR$^{a1}$, SiR$^{b1}$R$^{c1}$, or GeR$^{d1}$R$^{e1}$ (wherein R$^{a1}$, R$^{b1}$, R$^{c1}$, R$^{d1}$, and R$^{e1}$ are independently hydrogen, a C1 to C10 alkyl group, a C1 to C10 haloalkyl group, a C1 to C10 alkoxy group, —SiH$_3$, a C1 to C10 alkylsilyl group, —NH$_3$, a C1 to C10 alkylamine group, a C6 to C10 arylamine group, a C6 to C14 aryl group, a C6 to C14 aryloxy group, a C3 to C12 heteroaryl group, a halogen, a cyano group, or a combination thereof), $Y^2$ and $Y^3$ are independently O, S, Se, Te, S(=O), S(=O)$_2$, NR$^{a2}$, SiR$^{b2}$R$^{c2}$, GeR$^{d2}$R$^{e2}$, or CR$^{f2}$R$^{g2}$ (wherein R$^{a2}$, R$^{b2}$, R$^{c2}$, R$^{d2}$, R$^{e2}$, R$^{f2}$, and R$^{g2}$ are independently hydrogen, a C1 to C10 alkyl group, a C1 to C10 haloalkyl group, a C1 to C10 alkoxy group, —SiH$_3$, a C1 to C10 alkylsilyl group, —NH$_3$, a C1 to C10 alkylamine group, a C6 to C10 arylamine group, a C6 to C14 aryl group, a C6 to C14 aryloxy group, a C3 to C12 heteroaryl group, a halogen, a cyano group, or a combination thereof), R$^{b1}$ and R$^{c1}$, R$^{d1}$ and R$^{e1}$, R$^{b2}$ and R$^{c2}$, R$^{d2}$ and R$^{e2}$, and R$^{f2}$ and R$^{g2}$ may be independently present or combined with each other to from a spiro ring, an * outside the at least one aromatic ring is a linking point with Ar of Chemical Formula 1, and

*'s inside the at least one aromatic ring are linking portions with an N(R$^1$)-containing ring that includes R$^1$ of Chemical Formula 1 and an N(R$^2$)-containing ring that includes R$^2$ of Chemical Formula 1.

A peak absorption wavelength of the near-infrared absorber may be in a wavelength region of about 750 nm to about 3000 nm.

According to some example embodiments, a near-infrared absorbing/blocking film (absorbing and/or blocking film) including the near-infrared absorber is provided.

According to some example embodiments, a photoelectric device includes a first electrode and a second electrode facing each other, and an active layer between the first electrode and the second electrode, wherein the active layer includes a near-infrared absorber including the compound represented by Chemical Formula 1.

According to some example embodiments, an organic layer including the photoelectric device is provided.

According to some example embodiments, an electronic device including the photoelectric device or the organic sensor is provided.

According to some example embodiments, a photoelectric device may include a first electrode and a second electrode facing each other, an active layer between the first electrode and the second electrode, and a charge auxiliary layer between the active layer and the first electrode, or between the active layer and the second electrode. The charge auxiliary layer may include a near-infrared absorber that includes a compound represented by Chemical Formula 1:

[Chemical Formula 1]

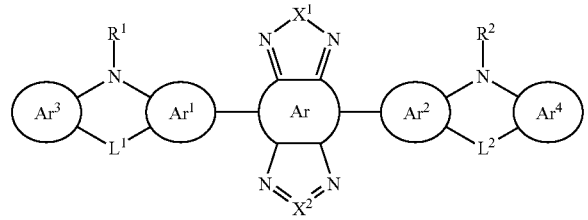

wherein, in Chemical Formula 1,

Ar is a substituted or unsubstituted C6 to C30 aromatic ring, a substituted or unsubstituted C3 to C30 heteroaromatic ring, or a combination thereof, $X^1$ is O, S, Se, Te, S(=O), S(=O$_2$), NR$^a$, CR$^b$R$^c$, SiR$^d$R$^e$, GeR$^f$R$^g$, CR$^h$CR$^i$, or CR$^{hh}$=CR$^{ii}$, wherein R$^a$, R$^b$, R$^c$, R$^d$, R$^e$, R$^f$, R$^g$, R$^h$, and R$^i$ are independently hydrogen, deuterium, a C1 to C30 alkyl group, a C1 to C30 haloalkyl group, a C6 to C30 aryl group, a C6 to C30 aryloxy group, a C3 to C30 heteroaryl group, a halogen, a cyano group, or a combination thereof, R$^{hh}$ and R$^{ii}$ are independently (CH)$_w$ or at least one heteroatom of O, N, S, Se, or Te where w is a positive integer, and R$^{hh}$ and R$^{ii}$ are linked to each other to form an aromatic ring or a heteroaromatic ring, $X^2$ is O, S, Se, Te, C, CR$^x$—CR$^y$, CR$^{xx}$—CR$^{yy}$, S(=O) or S(=O$_2$), wherein R$^x$ and R$^y$ are independently hydrogen, deuterium, a C1 to C30 alkyl group, a C1 to C30 haloalkyl group, a C6 to C30 aryl group, a C6 to C30 aryloxy group, a C3 to C30 heteroaryl group, a halogen, a cyano group, or a combination thereof, R$^{xx}$ and R$^{yy}$ are independently (CH)$_v$ where v is a positive integer or at least one heteroatom of O, N, S, Se, or Te, and R$^{xx}$ and R$^{yy}$ are linked to each other to form an aromatic ring or a heteroaromatic ring, Ar$^1$ and Ar$^2$ are independently a heteroarene group including at least one heteroatom of O, S, Se, or Te, Ar$^3$ and Ar$^4$ are independently a substituted or unsubstituted C6 to C30 arene group, a substituted or unsubstituted C3 to C30 heteroarene group, or a condensed ring group thereof, R$^1$ and R$^2$ are independently hydrogen, deuterium, a halogen, a cyano group, a nitro group, a hydroxyl group, a substituted or unsubstituted C1 to C10 alkyl group, a substituted or unsubstituted C1 to C10 alkoxy group, a substituted or unsubstituted C6 to C10 aryl group, or a substituted or unsubstituted C3 to C10 heteroaryl group, and L$^1$ and L$^2$ are independently a single bond, —O—, —S—, —Se—, —Te—, —N=, —NR$^a$—, —SiR$^b$R$^c$—, —GeR$^d$R$^e$—, —(CR$^f$R$^g$)$_n$—, or —(C(R$^h$)=C(R$^i$))—, wherein R$^a$, R$^b$, R$^c$, R$^d$, R$^e$, R$^f$, R$^g$, R$^h$, and R$^i$ are independently hydrogen, deuterium, a halogen, a cyano group, a substituted or unsubstituted C1 to C10 alkyl group, or a substituted or unsubstituted C6 to C10 aryl group, wherein R$^b$ and R$^c$, R$^d$ and R$^e$, R$^f$ and R$^g$, or R$^h$ and R$^i$ are independently present or are linked to each other to form a separate ring, and n of —(CR$^f$R$^g$)$_n$— is an integer of 1 or 2.

The active layer may further include the near-infrared absorber.

According to some example embodiments, an organic sensor may include a semiconductor substrate, a first photoelectric device on the semiconductor substrate, the first photoelectric device configured to selectively absorb light in a first near-infrared wavelength region, and an additional sensor configured to selectively absorb light in a separate wavelength region that is different from the first near-infrared wavelength region. The first photoelectric device may include a near-infrared absorber that includes a compound represented by Chemical Formula 1:

[Chemical Formula 1]

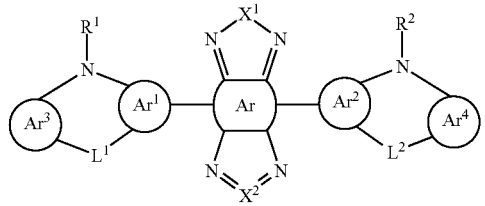

wherein, in Chemical Formula 1,

Ar is a substituted or unsubstituted C6 to C30 aromatic ring, a substituted or unsubstituted C3 to C30 heteroaromatic ring, or a combination thereof, $X^1$ is O, S, Se, Te, S(=O), S(=O$_2$), NR$^a$, CR$^b$R$^c$, SiR$^d$R$^e$, GeR$^f$R$^g$, CR$^h$CR$^i$, or CR$^{hh}$=CR$^{ii}$, wherein R$^a$, R$^b$, R$^c$, R$^d$, R$^e$, R$^f$, R$^g$, R$^h$, and R$^i$ are independently hydrogen, deuterium, a C1 to C30 alkyl group, a C1 to C30 haloalkyl group, a C6 to C30 aryl group, a C6 to C30 aryloxy group, a C3 to C30 heteroaryl group, a halogen, a cyano group, or a combination thereof, R$^{hh}$ and R$^{ii}$ are independently (CH)$_w$ where w is a positive integer or at least one heteroatom of O, N, S, Se, or Te, and R$^{hh}$ and R$^{ii}$ are linked to each other to form an aromatic ring or a heteroaromatic ring, $X^2$ is O, S, Se, Te, C, CR$^x$—CR$^y$, CR$^{xx}$—CR$^{yy}$, S(=O) or S(=O$_2$), wherein R$^x$ and R$^y$ are independently hydrogen, deuterium, a C1 to C30 alkyl group, a C1 to C30 haloalkyl group, a C6 to C30 aryl group, a C6 to C30 aryloxy group, a C3 to C30 heteroaryl group, a halogen, a cyano group, or a combination thereof, R$^{xx}$ and R$^{yy}$ are independently (CH)$_v$ where v is a positive integer or at least one heteroatom of O, N, S, Se, or Te, and R$^{xx}$ and R$^{yy}$ are linked to each other to form an aromatic ring or a heteroaromatic ring, Ar$^1$ and Ar$^2$ are independently a heteroarene group including at least one heteroatom of O, S, Se, or Te, Ar$^3$ and Ar$^4$ are independently a substituted or unsubstituted C6 to C30 arene group, a substituted or unsubstituted C3 to C30 heteroarene group, or a condensed ring group thereof, R$^1$ and R$^2$ are independently hydrogen, deuterium, a halogen, a cyano group, a nitro group, a hydroxyl group, a substituted or unsubstituted C1 to C10 alkyl group, a substituted or unsubstituted C1 to C10 alkoxy group, a substituted or unsubstituted C6 to C10 aryl group, or a substituted or unsubstituted C3 to C10 heteroaryl group, and $L^1$ and $L^2$ are independently a single bond, —O—, —S—, —Se—, —Te—, —N=, —NR$^a$—, —SiR$^b$R$^c$—, —GeR$^d$R$^e$—, —(CR$^f$R$^g$)$_n$—, or —(C(R$^h$)=C(R$^i$))—, wherein R$^a$, R$^b$, R$^c$, R$^d$, R$^e$, R$^f$, R$^g$, R$^h$, and R$^i$ are independently hydrogen, deuterium, a halogen, a cyano group, a substituted or unsubstituted C1 to C10 alkyl group, or a substituted or unsubstituted C6 to C10 aryl group, wherein R$^b$ and R$^c$, R$^d$ and R$^e$, R$^f$ and R$^g$, or R$^h$ and R$^i$ are independently present or are linked to each other to form a separate ring, and n of —(CR$^f$R$^g$)$_n$— is an integer of 1 or 2.

The additional sensor may be an infrared light sensor at least partially embedded within the semiconductor substrate, and the separate wavelength region may be a separate near-infrared wavelength region that is different from the first near-infrared wavelength region, and the first photoelectric device and the infrared light sensor may overlap in a vertical direction that is perpendicular to a top surface of the semiconductor substrate.

The additional sensor may include a plurality of photodiodes at least partially embedded within the semiconductor substrate, the plurality of photodiodes configured to selectively absorb light in separate visible wavelength regions, and the first photoelectric device and the plurality of photodiodes may overlap in a vertical direction that is perpendicular to a top surface of the semiconductor substrate.

The organic sensor may further include an additional photoelectric device on the semiconductor substrate, the additional photoelectric device being between the first photoelectric device and the semiconductor substrate, the additional photoelectric device configured to selectively absorb light in an additional wavelength region that is different from the first near-infrared wavelength region and the separate visible wavelength regions.

The additional sensor may include at least one additional photoelectric device vertically stacked between the first photoelectric device and the semiconductor substrate, each separate photoelectric device of the at least one additional photoelectric device including a separate photoelectric conversion layer and configured to selectively absorb light in a separate, respective wavelength region that is different from the first near-infrared wavelength region.

The first photoelectric device may include a first electrode and a second electrode facing each other; and an active layer between the first electrode and the second electrode, wherein the active layer includes the near-infrared absorber.

The first photoelectric device may include a first electrode and a second electrode facing each other; an active layer between the first electrode and the second electrode; and a charge auxiliary layer between the active layer and the first electrode, or between the active layer and the second electrode. The charge auxiliary layer may include the near-infrared absorber.

The near-infrared absorber may exhibit good absorbing properties in the near-infrared region and thus, may be effectively used in photoelectric devices and/or organic sensors.

DETAILED DESCRIPTION

Figure 1:
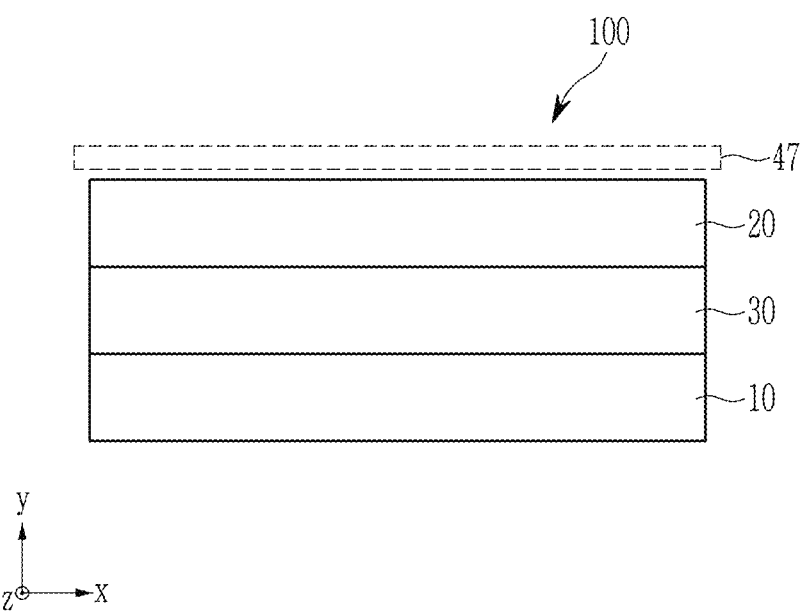
FIG. 1 is a cross-sectional view showing a photoelectric device according to some example embodiments.

Hereinafter, example embodiments will hereinafter be described in detail, and may be easily performed by a person having an ordinary skill in the related art. However, this disclosure may be embodied in many different forms and is not to be construed as limited to the example embodiments set forth herein.

In the drawings, the thickness of layers, films, panels, regions, etc., are exaggerated for clarity.

It will be understood that when an element such as a layer, film, region, or substrate is referred to as being "on" another element, it may be directly on the other element or intervening elements may also be present. In contrast, when an element is referred to as being "directly on" another element, there are no intervening elements present. It will further be understood that when an element is referred to as being "on" another element, it may be above or beneath the other element.

It will be understood that elements and/or properties thereof may be recited herein as being "the same" or "equal" as other elements, and it will be further understood that elements and/or properties thereof recited herein as being "the same" as or "equal" to other elements may be "the same" as or "equal" to or "substantially the same" as or "substantially equal" to the other elements and/or properties thereof. Elements and/or properties thereof that are "substantially the same" as or "substantially equal" to other elements and/or properties thereof will be understood to include elements and/or properties thereof that are the same as or equal to the other elements and/or properties thereof within manufacturing tolerances and/or material tolerances. Elements and/or properties thereof that are the same or substantially the same as other elements and/or properties thereof may be structurally the same or substantially the same, functionally the same or substantially the same, and/or compositionally the same or substantially the same.

It will be understood that elements and/or properties thereof described herein as being the "substantially" the same encompasses elements and/or properties thereof that have a relative difference in magnitude that is equal to or less than 10%.

Further, regardless of whether elements and/or properties thereof are modified as "substantially," it will be understood that these elements and/or properties thereof should be construed as including a manufacturing or operational tolerance (e.g., ±10%) around the stated elements and/or properties thereof.

When the terms "about" or "substantially" are used in this specification in connection with a numerical value, it is intended that the associated numerical value include a tolerance of ±10% around the stated numerical value. When ranges are specified, the range includes all values therebetween such as increments of 0.1%.

In the drawings, parts having no relationship with the description are omitted for clarity of the embodiments, and the same or similar constituent elements are indicated by the same reference numeral throughout the specification.

As used herein, "at least one of A, B, or C," "one of A, B, C, or a combination thereof" and "one of A, B, C, and a combination thereof" refer to each constituent element, and a combination thereof (e.g., A; B; C; A and B; A and C; B and C; or A, B, and C).

Hereinafter, "combination" includes a mixture of two or more, inter-substitution, and a laminate structure of two or more.

As used herein, when specific definition is not otherwise provided, "substituted" refers to replacement of a hydrogen of a compound or a functional group by a substituent selected from a halogen atom (F, Br, Cl, or I), a hydroxy group, a nitro group, a cyano group, an amino group, an azido group, an amidino group, an amine group (—NR'R", wherein R' and R" are the same or different, and are a hydrogen atom, a C1 to C20 alkyl group, or a C6 to C30 aryl group), a hydrazino group, a hydrazono group, a carbonyl group, a carbamyl group, a thiol group, an ester group, a carboxyl group or a salt thereof, a sulfonic acid group or a salt thereof, a phosphoric acid group or a salt thereof, a silyl group (—SiR$^1$R$^2$R$^3$, wherein R$^1$ to R$^3$ is hydrogen, a C1 to C10 alkyl group, or a C6 to C10 aryl group), a C1 to C20 alkyl group, a C1 to C20 alkoxy group, a C2 to C20 alkenyl group, a C2 to C20 alkynyl group, a C6 to C30 aryl group, a C7 to C30 arylalkyl group, a C1 to C30 alkoxy group, a C1 to C20 heteroalkyl group, a C3 to C20 heteroaryl group, a C3 to C20 heteroarylalkyl group, a C3 to C30 cycloalkyl group, a C3 to C15 cycloalkenyl group, a C6 to C15 cycloalkynyl group, a C3 to C30 heterocycloalkyl group, and a combination thereof.

As used herein, when specific definition is not otherwise provided, "hetero" refers to one including 1 to 4 heteroatoms selected from N, O, S, Se, Te, Si, and P.

As used herein, when a definition is not otherwise provided, "aromatic ring" refers to a functional group in which all atoms in the cyclic functional group have a p-orbital, and wherein these p-orbitals are conjugated and "heteroaromatic ring" refers to the aromatic ring including a heteroatom. The "aromatic ring" refers to a C6 to C30 arene group, for example a C6 to C20 arene group or a C6 to C30 aryl group, for example a C6 to C20 aryl group. The "heteroaromatic ring" refers to a C3 to C30 heteroarene group, for example a C3 to C20 heteroarene group or a C6 to C30 heteroaryl group, for example a C6 to C20 heteroaryl group.

As used herein, "arene group" refers to a hydrocarbon ring group having an aromatic ring, and includes monocyclic and polycyclic hydrocarbon ring groups, and the additional ring of the polycyclic hydrocarbon ring group may be an aromatic ring or a nonaromatic ring. The arene group may be a C6 to C30 arene group, a C6 to C20 arene group, or a C6 to C10 arene group. The heteroarene group means an arene group including 1 to 3 heteroatoms selected from N, O, S, P, and Si in the ring. The heteroarene group may be a C3 to C30 heteroarene group, a C3 to C20 heteroarene group, or a C3 to C10 heteroarene group.

As used herein, when a definition is not otherwise provided, "aryl group" refers to a group including at least one hydrocarbon aromatic moiety, and may include a group in which all elements of the hydrocarbon aromatic moiety have p-orbitals which form conjugation, for example a phenyl group, a naphthyl group, and the like; a group in which two or more hydrocarbon aromatic moieties may be linked by a sigma bond, for example a biphenyl group, a terphenyl group, a quarterphenyl group, and the like; and a group in which two or more hydrocarbon aromatic moieties are fused directly or indirectly to provide a non-aromatic fused ring, for example a fluorenyl group. The aryl group may include a monocyclic, polycyclic or fused polycyclic (i.e., rings sharing adjacent pairs of carbon atoms) functional group.

As used herein, when a definition is not otherwise provided, "heteroaryl group" refers to an aryl group including at least one heteroatom selected from N, O, S, Se, Te, P, and Si instead of carbon (C) in the ring. When the heteroaryl group is a fused ring, at least one of rings of the heteroaryl group may have a heteroatom or each ring may have a heteroatom.

As used herein, when a definition is not otherwise provided, "ring" refers to an aromatic ring, a non-aromatic ring, a heteroaromatic ring, a hetero non-aromatic ring, a fused ring thereof, and/or a combination thereof. The aromatic ring are the same as described above and the non-aromatic ring may be a C3 to C30 cycloalkyl group, a C3 to C30 cycloalkenyl group, or a C3 to C30 cycloalkynyl group.

As used herein, when a definition is not otherwise provided, "halogen" may be one of F, Cl, Br, or I and the haloalkyl group may be an alkyl group in which at least one hydrogen is replaced by a halogen and may be, for example, a perfluoroalkyl group such as —CF$_3$.

Hereinafter, a near-infrared absorber according to some example embodiments is described. The near-infrared absorber may be referred to herein interchangeably as a "near-infrared absorbing compound."

The near-infrared absorber includes a compound represented by Chemical Formula 1.

[Chemical Formula 1]

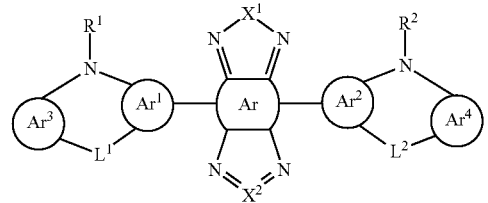

In Chemical Formula 1,

Ar is a substituted or unsubstituted C6 to C30 aromatic ring, a substituted or unsubstituted C3 to C30 heteroaromatic ring, or a combination thereof, X$^1$ is O, S, Se, Te, S(=O), S(=O)$_2$, NR$^a$, CR$^b$R$^c$, SiR$^d$R$^e$, GeR$^f$R$^g$, CR$^h$CR$^i$, or CR$^{hh}$=CR$^{ii}$ (wherein R$^a$, R$^b$, R$^c$, R$^d$, R$^e$, R$^f$, R$^g$, R$^h$, and R$^i$ are independently hydrogen, deuterium, a C1 to C30 alkyl group, a C1 to C30 haloalkyl group, a C6 to C30 aryl group, a C6 to C30 aryloxy group, a C3 to C30 heteroaryl group, a halogen, a cyano group, or a combination thereof, R$^{hh}$ and R$^{ii}$ are independently (CH)$_w$ where w is a positive integer or at least one heteroatom of O, N, S, Se, or Te, and $R^{hh}$ and $R^{ii}$ are linked to each other to form an aromatic ring or a heteroaromatic ring), $X^2$ is O, S, Se, Te, C, $CR^x$—$CR^y$, $CR^{xx}$—$CR^{yy}$, S(=O) or S(=$O_2$) (wherein $R^x$ and $R^y$ are independently hydrogen, deuterium, a C1 to C30 alkyl group, a C1 to C30 haloalkyl group, a C6 to C30 aryl group, a C6 to C30 aryloxy group, a C3 to C30 heteroaryl group, a halogen, a cyano group, or a combination thereof, $R^{xx}$ and $R^{yy}$ are independently $(CH)_v$ where v is a positive integer or at least one heteroatom of O, N, S, Se, or Te, and $R^{xx}$ and $R^{yy}$ are linked to each other to form an aromatic ring or a heteroaromatic ring), $Ar^1$ and $Ar^2$ are independently a heteroarene group including at least one heteroatom of O, S, Se, or Te, $Ar^3$ and $Ar^4$ are independently a substituted or unsubstituted C6 to C30 arene group, a substituted or unsubstituted C3 to C30 heteroarene group, or a condensed ring group thereof, $R^1$ and $R^2$ are independently hydrogen, deuterium, a halogen, a cyano group, a nitro group, a hydroxyl group, a substituted or unsubstituted C1 to C10 alkyl group, a substituted or unsubstituted C1 to C10 alkoxy group, a substituted or unsubstituted C6 to C10 aryl group, or a substituted or unsubstituted C3 to C10 heteroaryl group, $L^1$ and $L^2$ are independently a single bond, —O—, —S—, —Se—, —Te—, —N=, —$NR^a$—, —$SiR^bR^c$—, —$GeR^dR^e$—, —$(CR^fR^g)_n$—, or —$(C(R^h)=C(R^i))$— (wherein $R^a$, $R^b$, $R^c$, $R^d$, $R^e$, $R^f$, $R^g$, $R^h$, and $R^i$ are independently hydrogen, deuterium, a halogen, a cyano group, a substituted or unsubstituted C1 to C10 alkyl group, or a substituted or unsubstituted C6 to C10 aryl group, wherein $R^b$ and $R^c$, $R^d$ and $R^e$, $R^f$ and $R^g$, or $R^h$ and R' are independently present or are linked to each other to form a separate ring, and n of —$(CR^fR^g)_n$— is an integer of 1 or 2).

It is desirable that a material absorbing light in a long wavelength like the near-infrared light has small HOMO-LUMO bandgap energy, also referred to herein as small bandgap energy, low bandgap energy, or the like. In order to have the small bandgap energy, a conjugation length thereof may be made to be longer, but when the conjugation length becomes long, a deposition process is difficult to apply. The near-infrared absorber represented by Chemical Formula 1 has a donor-acceptor-donor structure that a core of a conjugation structure having electron-accepting characteristics (Ar-containing ring in Chemical Formula 1) is linked to an aromatic fused ring having electron-donating characteristics ($Ar^1$-(a ring including N($R^1$) and $L^1$)-$Ar^3$) and ($Ar^2$-(a ring including N($R^2$) and $L^2$)-$Ar^4$), and thus the near-infrared absorber has strong charge transfer characteristics and may effectively absorb light in a near-infrared wavelength region due to low bandgap energy. In addition, the near-infrared absorber has improved thermal stability and may be appropriate for a deposition process. Accordingly, a layer and/or structure that includes the near-infrared absorber may have improved sensitivity to and/or absorbance of light in the near-infrared wavelength region. A device configured to selectively absorb and/or convert (into electrical signals, e.g., photoelectrically convert) near-infrared light (e.g., a sensor) may have improved performance and/or efficiency based on including the near-infrared absorber, for example in an active layer configured to selectively absorb and/or convert (into electrical signals, e.g., photoelectrically convert) said near-infrared light.

Hereinafter, the "ring including N($R^1$) and $L^1$" may be called to be an "N($R^1$)-containing ring," and the "ring including N($R^2$) and $L^2$" may be called to be an "N($R^2$)-containing ring."

The "N($R^1$)-containing ring" and "ring including N($R^2$) and $L^2$" may be individually a pentagonal ring (e.g., a substituted or unsubstituted pyrrole ring), a hexagonal ring (e.g., a substituted or unsubstituted pyridine ring, a substituted or unsubstituted oxazine ring, a substituted or unsubstituted thiazine ring, a substituted or unsubstituted selenoazine ring, or a substituted or unsubstituted pyrazine ring), or a heptagonal ring (e.g., a substituted or unsubstituted azepine ring) depending on $L^1$ and $L^2$.

In Chemical Formula 1, Ar may be benzene ring, a substituted or unsubstituted naphthalene ring, a substituted or unsubstituted anthracene ring, a substituted or unsubstituted phenanthrene ring, a substituted or unsubstituted tetracene ring, or a substituted or unsubstituted pyrene ring.

In Chemical Formula 1, Ar may be a substituted or unsubstituted quinoline ring, a substituted or unsubstituted isoquinoline ring, a substituted or unsubstituted quinoxaline ring, a substituted or unsubstituted quinazoline ring, or a substituted or unsubstituted phenanthroline ring.

In Chemical Formula 1, Ar may be one moiety of a set of moieties represented by Chemical Formula A-1, each moiety including at least one aromatic ring and left and right linking groups.

[Chemical Formula A-1]

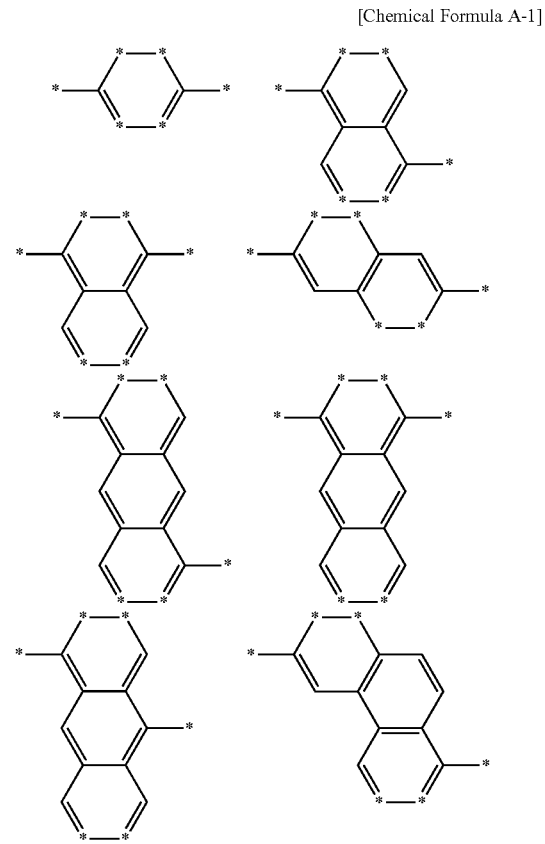

In Chemical Formula A-1, hydrogen of each aromatic ring may be replaced by a halogen, a cyano group, a C1 to C10 alkyl group, a C1 to C10 alkoxy group, a C1 to C10 haloalkyl group, —$SiH_3$, or a C1 to C10 alkylsilyl group, separate adjacent pairs of *'s inside the at least one aromatic ring are linking portions with separate, respective ones of an N—$X^1$—N-containing ring of Chemical Formula 1 or —N=$X^2$=N-containing ring of Chemical Formula 1, and

*'s of the left and right linking groups are portions linked to separate, respective ones of Ar¹ or Ar² of Chemical Formula 1.

In Chemical Formula 1, Ar may be one moiety of a set of moieties represented by Chemical Formula A-2, each moiety including at least one aromatic ring and left and right linking groups.

[Chemical Formula A-2]

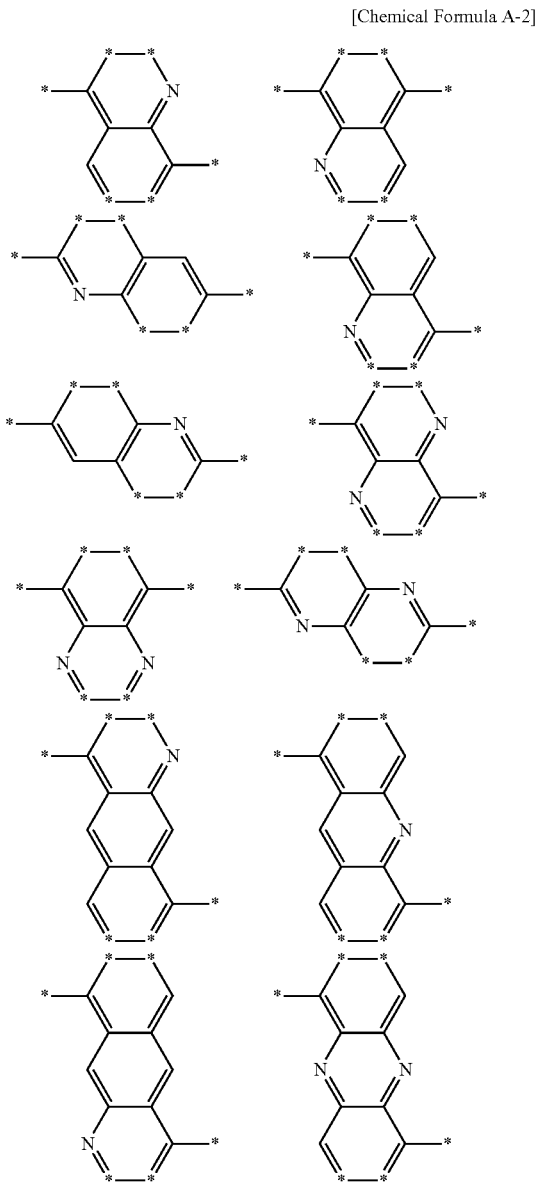

In Chemical Formula A-2, hydrogen of each aromatic ring may be replaced by a halogen, a cyano group, a C1 to C10 alkyl group, a C1 to C10 alkoxy group, a C1 to C10 haloalkyl group, —SiH$_3$, or a C1 to C10 alkylsilyl group, separate adjacent pairs of *'s inside the at least one aromatic ring are linking portions with separate, respective ones of an N—X¹—N-containing ring of Chemical Formula 1 or —N=X²=N-containing ring of Chemical Formula 1, and

*'s of the left and right linking groups are portions linked to separate, respective ones of Ar¹ or Ar² of Chemical Formula 1.

In Chemical Formula 1, when $X^2$ is $CR^{xx}$—$CR^{yy}$, $R^{xx}$ and $R^{yy}$ may be linked to each other to form an aromatic ring. In this way, when the aromatic ring is further fused, an absorption wavelength of the compound is shifted to a long wavelength and stability of the compound may be increased.

The aromatic ring may be substituted or unsubstituted benzene ring, a substituted or unsubstituted naphthalene ring, a substituted or unsubstituted acenaphthene ring, a substituted or unsubstituted anthracene ring, a substituted or unsubstituted phenanthrene ring, a substituted or unsubstituted tetracene ring or a substituted or unsubstituted pyrene ring; or a substituted or unsubstituted quinoline ring, a substituted or unsubstituted isoquinoline ring, a substituted or unsubstituted quinoxaline ring, a substituted or unsubstituted quinazoline ring, a substituted or unsubstituted phenanthroline ring, a substituted or unsubstituted pyrimidine ring, or a substituted or unsubstituted benzodithiophene ring.

The aromatic ring may be one moiety of a set of moieties represented by Chemical Formula B-1, each moiety including at least one aromatic ring.

[Chemical Formula B-1]

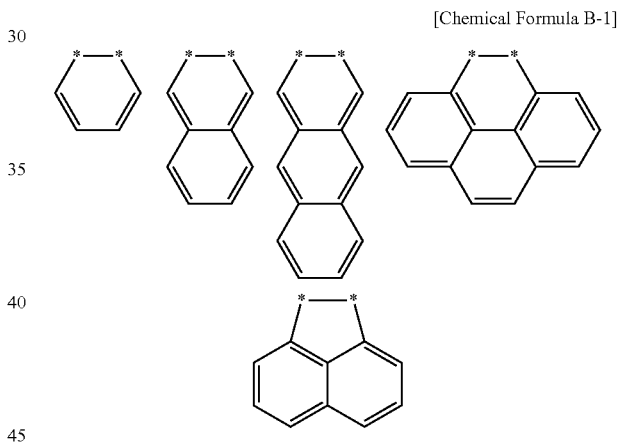

In Chemical Formula B-1, hydrogen of each aromatic ring may be replaced by a halogen, a cyano group, a C1 to C30 alkyl group (e.g., a C1 to C20 alkyl group or a C1 to C10 alkyl group), a C1 to C30 alkoxy group (e.g., a C1 to C20 alkoxy group or a C1 to C10 alkoxy group), a C1 to C30 haloalkyl group (e.g., a C1 to C20 haloalkyl group or a C1 to C10 haloalkyl group), —SiH$_3$, a C1 to C30 alkylsilyl group (e.g., a C1 to C20 alkylsilyl group or a C1 to C10 alkylsilyl group), a C6 to C30 aryl group (e.g., a C6 to C20 aryl group or a C6 to C10 aryl group), a C6 to C30 aryloxy group (e.g., a C6 to C20 aryloxy group or a C6 to C10 aryloxy group), or a C3 to C30 heteroaryl group (e.g., a C3 to C20 heteroaryl group or a C3 to C10 heteroaryl group), and

*'s inside the at least one aromatic ring are linking portions with a carbon of $CR^{xx}$—$CR^{yy}$.

The at least one aromatic ring may be one moiety of a set of moieties represented by Chemical Formula B-2, each moiety including at least one aromatic ring.

[Chemical Formula B-2]

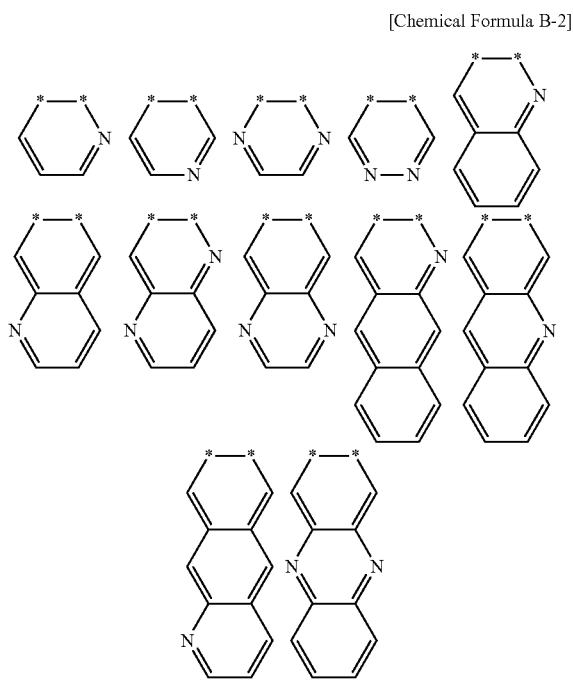

In Chemical Formula B-2, hydrogen of each aromatic ring may be replaced by a halogen, a cyano group, a C1 to C30 alkyl group (e.g., a C1 to C20 alkyl group or a C1 to C10 alkyl group), a C1 to C30 alkoxy group (e.g., a C1 to C20 alkoxy group or a C1 to C10 alkoxy group), a C1 to C30 haloalkyl group (e.g., a C1 to C20 haloalkyl group or a C1 to C10 haloalkyl group), —SiH$_3$, a C1 to C30 alkylsilyl group (e.g., a C1 to C20 alkylsilyl group or a C1 to C10 alkylsilyl group), a C6 to C30 aryl group (e.g., a C6 to C20 aryl group or a C6 to C10 aryl group), a C6 to C30 aryloxy group (e.g., a C6 to C20 aryloxy group or a C6 to C10 aryloxy group), or a C3 to C30 heteroaryl group (e.g., a C3 to C20 heteroaryl group or a C3 to C10 heteroaryl group), and

*'s inside the at least one aromatic ring are linking portions with a carbon of CR$^{xx}$—CR$^{yy}$.

The aromatic ring may be a moiety represented by Chemical Formulas B-3-1 or Chemical Formula B-3-2, each moiety including at least one aromatic ring.

[Chemical Formula B-3-1]

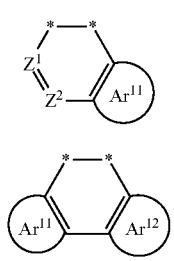

[Chemical Formula B-3-2]

In Chemical Formulas B-3-1 and B-3-2,

Ar$^{11}$ and Ar$^{12}$ are independently a substituted or unsubstituted C6 to C30 arene group or a substituted or unsubstituted C3 to C30 heteroarene group.

In Chemical Formula B-3-1, Z$^1$ and Z$^2$ are independently CR$^a$ or N (wherein R$^a$ is hydrogen, deuterium, a C1 to C30 alkyl group (e.g., a C1 to C20 alkyl group or a C1 to C10 alkyl group), a C1 to C30 alkoxy group (e.g., a C1 to C20 alkoxy group or a C1 to C10 alkoxy group), a C1 to C30 haloalkyl group (e.g., a C1 to C20 haloalkyl group or a C1 to C10 haloalkyl group), —SiH$_3$, a C1 to C30 alkylsilyl group (e.g., a C1 to C20 alkylsilyl group or a C1 to C10 alkylsilyl group), —NH$_2$, a C1 to C30 alkylamine group (e.g., a C1 to C20 alkylamine group or a C1 to C10 alkylamine group), a C6 to C30 arylamine group (e.g., a C6 to C20 arylamine group or a C6 to C10 arylamine group), a C6 to C30 aryl group (e.g., a C6 to C20 aryl group or a C6 to C10 aryl group), a C6 to C30 aryloxy group (e.g., a C6 to C20 aryloxy group or a C6 to C10 aryloxy group), a C3 to C30 heteroaryl group, a halogen, a cyano group, or a combination thereof), and

*'s inside the at least one aromatic ring are linking portions with a carbon of CR$^{xx}$—CR$^{yy}$.

A moiety represented by Chemical Formula B-3-1 may be one moiety of a set of moieties represented by Chemical Formula B-3-11, each moiety including at least one aromatic ring.

[Chemical Formula B-3-11]

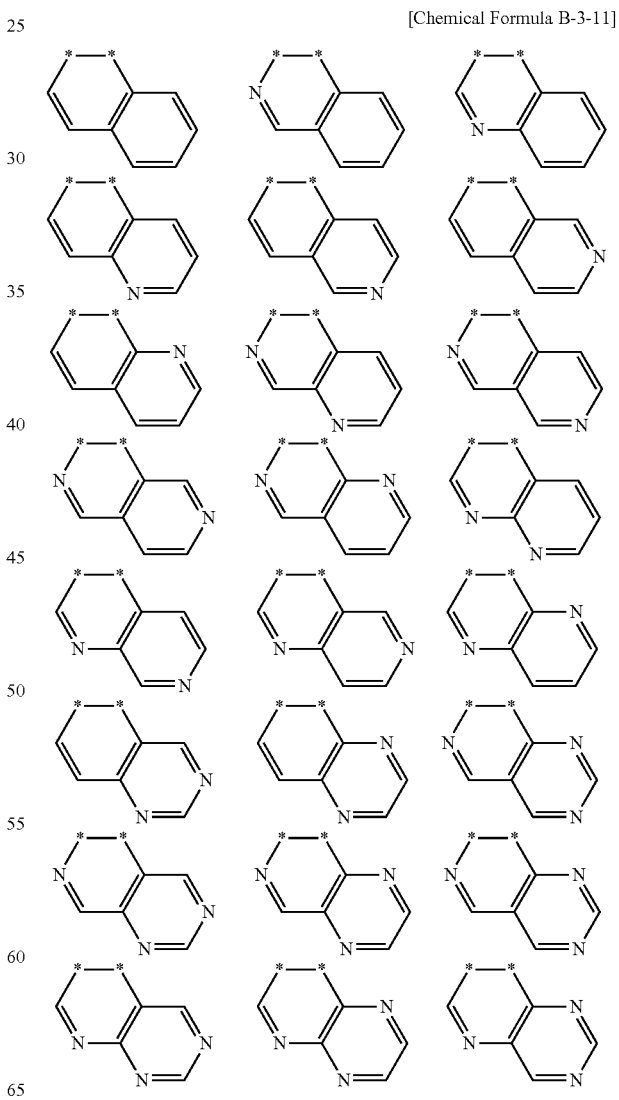

In Chemical Formula B-3-11, hydrogen of each aromatic ring may be replaced by a halogen, a cyano group, a C1 to C30 alkyl group (e.g., a C1 to C20 alkyl group or a C1 to C10 alkyl group), a C1 to C30 alkoxy group (e.g., a C1 to C20 alkoxy group or a C1 to C10 alkoxy group), a C1 to C30 haloalkyl group (e.g., a C1 to C20 haloalkyl group or a C1 to C10 haloalkyl group), —SiH$_3$, a C1 to C30 alkylsilyl group (e.g., a C1 to C20 alkylsilyl group or a C1 to C10 alkylsilyl group), a C6 to C30 aryl group (e.g., a C6 to C20 aryl group or a C6 to C10 aryl group), a C6 to C30 aryloxy group (e.g., a C6 to C20 aryloxy group or a C6 to C10 aryloxy group), or a C3 to C30 heteroaryl group (e.g., a C3 to C20 heteroaryl group or a C3 to C10 heteroaryl group), and

*'s inside the at least one aromatic ring are linking portions with the carbon of CR$^{xx}$—CR$^{yy}$.

A moiety represented by Chemical Formula B-3-2 may be one moiety of a set of moieties represented by Chemical Formula B-3-21, each moiety including at least one aromatic ring.

[Chemical Formula B-3-21]

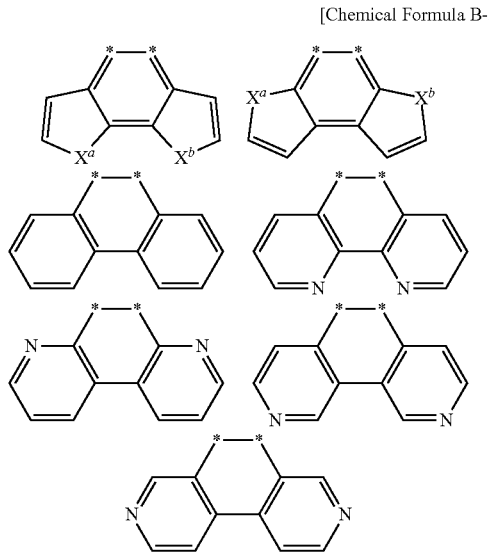

In Chemical Formula B-3-21, hydrogen of each aromatic ring may be replaced by a halogen, a cyano group, a C1 to C30 alkyl group (e.g., a C1 to C20 alkyl group or a C1 to C10 alkyl group), a C1 to C30 alkoxy group (e.g., a C1 to C20 alkoxy group or a C1 to C10 alkoxy group), a C1 to C30 haloalkyl group (e.g., a C1 to C20 haloalkyl group or a C1 to C10 haloalkyl group), —SiH$_3$, a C1 to C30 alkylsilyl group (e.g., a C1 to C20 alkylsilyl group or a C1 to C10 alkylsilyl group), a C6 to C30 aryl group (e.g., a C6 to C20 aryl group or a C6 to C10 aryl group), a C6 to C30 aryloxy group (e.g., a C6 to C20 aryloxy group or a C6 to C10 aryloxy group), or a C3 to C30 heteroaryl group (e.g., a C3 to C20 heteroaryl group or a C3 to C10 heteroaryl group), X$^a$ and X$^b$ are independently O, S, Se, Te, NR$^a$, SiR$^b$R$^c$, or GeR$^d$R$^e$ (wherein R$^a$, R$^b$, R$^c$, R$^d$, and R$^e$ are independently hydrogen, a halogen, a cyano group, a substituted or unsubstituted C1 to C30 alkyl group (e.g., a C1 to C20 alkyl group or a C1 to C10 alkyl group), a substituted or unsubstituted C1 to C30 alkoxy group (e.g., a C1 to C20 alkoxy group or a C1 to C10 alkoxy group), a substituted or unsubstituted C6 to C30 aryl group (e.g., a C6 to C20 aryl group or a C6 to C10 aryl group), or a substituted or unsubstituted C6 to C30 aryloxy group (e.g., a C6 to C20 aryloxy group or a C6 to C10 aryloxy group)), and

*'s inside the at least one aromatic ring are linking portions with the carbon of CR$^{xx}$—CR$^{yy}$.

For example, in Chemical Formulas B-3-11 and B-3-21, halogen may be any of F, Cl, Br, and I, and the haloalkyl group may be an alkyl group in which at least one hydrogen is replaced by a halogen, for example, a perfluoroalkyl group such as —CF$_3$.

In Chemical Formula 1, Ar$^1$ and Ar$^2$ are heteroatom-containing ring groups, and the heteroatoms included in the rings may reinforce charge transfer characteristics and decrease bandgap energy. In addition, the number of aromatic rings of Ar$^1$ and Ar$^2$ may be changed to easily adjust an absorption wavelength. Since the structure that the plurality of aromatic rings is fused (Ar$^1$-(the ring including N(R$^1$) and L$^1$)-Ar$^3$) and (Ar$^2$-(the ring including N(R$^2$) and L$^2$)-Ar$^4$) provides a donor structure and thus increases a length of the conjugation structure, light of a long wavelength in a near-infrared region may be absorbed.

In Chemical Formula 1, Ar$^1$ and Ar$^2$ may be the same or different and may each be represented by one of Chemical Formula C-1-1, Chemical Formula C-1-2, or Chemical Formula C-1-3 that each include at least one aromatic ring.

[Chemical Formula C-1-1]

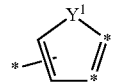

[Chemical Formula C-1-2]

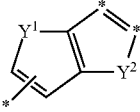

[Chemical Formula C-1-3]

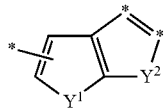

In Chemical Formulas C-1-1 to C-1-3, hydrogen of each aromatic ring may be replaced by a halogen, a cyano group, a C1 to C30 alkyl group (e.g., a C1 to C20 alkyl group or a C1 to C10 alkyl group), a C1 to C30 alkoxy group (e.g., a C1 to C20 alkoxy group or a C1 to C10 alkoxy group), a C1 to C30 haloalkyl group (e.g., a C1 to C20 haloalkyl group or a C1 to C10 haloalkyl group), —SiH$_3$, a C1 to C30 alkylsilyl group (e.g., a C1 to C20 alkylsilyl group or a C1 to C10 alkylsilyl group), a C6 to C30 aryl group (e.g., a C6 to C20 aryl group or a C6 to C10 aryl group), a C6 to C30 aryloxy group (e.g., a C6 to C20 aryloxy group or a C6 to C10 aryloxy group), or a C3 to C30 heteroaryl group (e.g., a C3 to C20 heteroaryl group or a C3 to C10 heteroaryl group), Y$^1$ is O, S, Se, Te, S(=O), S(=O)$_2$, NR$^{a1}$, SiR$^{b1}$R$^{c1}$, or GeR$^{d1}$R$^{e1}$ (wherein R$^{a1}$, R$^{b1}$, R$^{c1}$, R$^{d1}$, and R$^{e1}$ are independently hydrogen, a C1 to C10 alkyl group, a C1 to C10 haloalkyl group, a C1 to C10 alkoxy group, —SiH$_3$, a C1 to C10 alkylsilyl group, —NH$_3$, a C1 to C10 alkylamine group, a C6 to C10 arylamine group, a C6 to C14 aryl group, a C6 to C14 aryloxy group, a C3 to C12 heteroaryl group, a halogen, a cyano group, or a combination thereof), Y$^2$ is O, S, Se, Te, S(=O), S(=O)$_2$, NR$^{a2}$, SiR$^{b2}$R$^{c2}$, GeR$^{d2}$R$^{e2}$, or CR$^{f2}$R$^{g2}$ (wherein R$^{a2}$, R$^{b2}$, R$^{c2}$, R$^{d2}$, R$^{e2}$, R$^{f2}$, and $R^{g2}$ are independently hydrogen, a C1 to C10 alkyl group, a C1 to C10 haloalkyl group, a C1 to C10 alkoxy group, —SiH$_3$, a C1 to C10 alkylsilyl group, —NH$_3$, a C1 to C10 alkylamine group, a C6 to C10 arylamine group, a C6 to C14 aryl group, a C6 to C14 aryloxy group, a C3 to C12 heteroaryl group, a halogen, a cyano group, or a combination thereof), $R^{b1}$ and $R^{c1}$, $R^{d1}$ and $R^{e1}$, $R^{b2}$ and $R^{c2}$, $R^{d2}$ and $R^{e2}$, and $R^{f2}$ and $R^{g2}$ may be independently present or combined with each other to from a spiro ring (e.g., a C4 to C8 cycloalkyl group, a C5 cycloalkyl group, or a C6 cycloalkyl group), an * outside the at least one aromatic ring is a linking point with Ar of Chemical Formula 1, and

*'s inside the at least one aromatic ring are linking portions with an N(R$^1$)-containing ring that includes R$^1$ of Chemical Formula 1 and an N(R$^2$)-containing ring that includes R$^2$ of Chemical Formula 1.

In Chemical Formula 1, Ar$^1$ and Ar$^2$ may be the same or different and may each be represented by one of Chemical Formulas C-2-1 to C-2-4 that each include at least one aromatic ring.

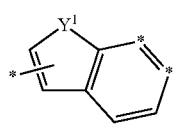

[Chemical Formula C-2-1]

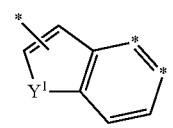

[Chemical Formula C-2-2]

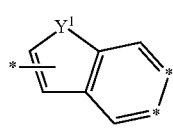

[Chemical Formula C-2-3]

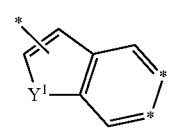

[Chemical Formula C-2-4]

In Chemical Formulas C-2-1 to C-2-4, hydrogen of each aromatic ring may be replaced by a halogen, a cyano group, a C1 to C30 alkyl group (e.g., a C1 to C20 alkyl group or a C1 to C10 alkyl group), a C1 to C30 alkoxy group (e.g., a C1 to C20 alkoxy group or a C1 to C10 alkoxy group), a C1 to C30 haloalkyl group (e.g., a C1 to C20 haloalkyl group or a C1 to C10 haloalkyl group), —SiH$_3$, a C1 to C30 alkylsilyl group (e.g., a C1 to C20 alkylsilyl group or a C1 to C10 alkylsilyl group), a C6 to C30 aryl group (e.g., a C6 to C20 aryl group or a C6 to C10 aryl group), a C6 to C30 aryloxy group (e.g., a C6 to C20 aryloxy group or a C6 to C10 aryloxy group), or a C3 to C30 heteroaryl group (e.g., a C3 to C20 heteroaryl group or a C3 to C10 heteroaryl group), Y$^1$ is O, S, Se, Te, S(=O), S(=O)$_2$, NR$^{a1}$, SiR$^{b1}$R$^{c1}$, or GeR$^{d1}$R$^{e1}$ (wherein R$^{a1}$, R$^{b1}$, R$^{c1}$, R$^{d1}$, and R$^{e1}$ are independently hydrogen, a C1 to C10 alkyl group, a C1 to C10 haloalkyl group, a C1 to C10 alkoxy group, —SiH$_3$, a C1 to C10 alkylsilyl group, —NH$_3$, a C1 to C10 alkylamine group, a C6 to C10 arylamine group, a C6 to C14 aryl group, a C6 to C14 aryloxy group, a C3 to C12 heteroaryl group, a halogen, a cyano group, or a combination thereof), R$^{b1}$ and R$^{c1}$ and R$^{d1}$ and R$^{e1}$ may independently be present or combined with each other to from a spiro ring (e.g., a C4 to C8 cycloalkyl group, a C5 cycloalkyl group, or a C6 cycloalkyl group), an * outside the at least one aromatic ring is a linking point with Ar of Chemical Formula 1, and

*'s inside the at least one aromatic ring are linking portions with an N(R$^1$)-containing ring that includes R$^1$ of Chemical Formula 1 and an N(R$^2$)-containing ring that includes R$^2$ of Chemical Formula 1.

In Chemical Formula 1, Ar$^1$ and Ar$^2$ may be the same or different and may each be represented by one of Chemical Formulas C-3-1 to C-3-6 that each include at least one aromatic ring.

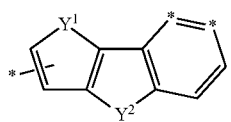

[Chemical Formula C-3-1]

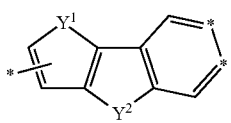

[Chemical Formula C-3-2]

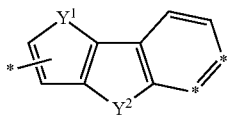

[Chemical Formula C-3-3]

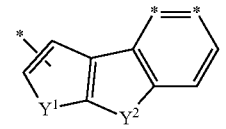

[Chemical Formula C-3-4]

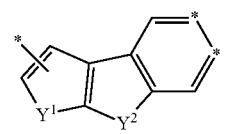

[Chemical Formula C-3-5]

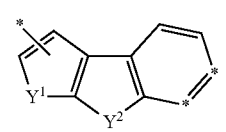

[Chemical Formula C-3-6]

In Chemical Formulas C-3-1 to C-3-6, hydrogen of each aromatic ring may be replaced by a halogen, a cyano group, a C1 to C30 alkyl group (e.g., a C1 to C20 alkyl group or a C1 to C10 alkyl group), a C1 to C30 alkoxy group (e.g., a C1 to C20 alkoxy group or a C1 to C10 alkoxy group), a C1 to C30 haloalkyl group (e.g., a C1 to C20 haloalkyl group or a C1 to C10 haloalkyl group), —SiH$_3$, a C1 to C30 alkylsilyl group (e.g., a C1 to C20 alkylsilyl group or a C1 to C10 alkylsilyl group), a C6 to C30 aryl group (e.g., a C6 to C20 aryl group or a C6 to C10 aryl group), a C6 to C30 aryloxy group (e.g., a C6 to C20 aryloxy group or a C6 to C10 aryloxy group), or a C3 to C30 heteroaryl group (e.g., a C3 to C20 heteroaryl group or a C3 to C10 heteroaryl group), Y$^1$ is O, S, Se, Te, S(=O), S(=O)$_2$, NR$^{a1}$, SiR$^{b1}$R$^{c1}$, or GeR$^{d1}$R$^{e1}$ (wherein R$^{a1}$, R$^{b1}$, R$^{c1}$, R$^{d1}$, and R$^{e1}$ are independently hydrogen, a C1 to C10 alkyl group, a C1 to C10 haloalkyl group, a C1 to C10 alkoxy group, —SiH$_3$, a C1 to C10 alkylsilyl group, —NH$_3$, a C1 to C10 alkylamine group, a C6 to C10 arylamine group, a C6 to C14 aryl group, a C6 to C14 aryloxy group, a C3 to C12 heteroaryl group, a halogen, a cyano group, or a combination thereof), $Y^2$ is O, S, Se, Te, S(=O), S(=O)$_2$, NR$^{a2}$, SiR$^{b2}$R$^{c2}$, GeR$^{d2}$R$^{e2}$, or CR$^{f2}$R$^{g2}$ (wherein R$^{a2}$, R$^{b2}$, R$^{c2}$, R$^{d2}$, R$^{e2}$, R$^{f2}$, and R$^{g2}$ are independently hydrogen, a C1 to C10 alkyl group, a C1 to C10 haloalkyl group, a C1 to C10 alkoxy group, —SiH$_3$, a C1 to C10 alkylsilyl group, —NH$_3$, a C1 to C10 alkylamine group, a C6 to C10 arylamine group, a C6 to C14 aryl group, a C6 to C14 aryloxy group, a C3 to C12 heteroaryl group, a halogen, a cyano group, or a combination thereof), R$^{b1}$ and R$^{c1}$, R$^{d1}$ and R$^{e1}$, R$^{b2}$ and R$^{c2}$, R$^{d2}$ and R$^{e2}$, and R$^{f2}$ and R$^{g2}$ may be independently present or combined with each other to from a spiro ring (e.g., a C4 to C8 cycloalkyl group, a C5 cycloalkyl group, or a C6 cycloalkyl group), an * outside the at least one aromatic ring is a linking point with Ar of Chemical Formula 1, and

*'s inside the at least one aromatic ring are linking portions with an N(R$^1$)-containing ring that includes R$^1$ of Chemical Formula 1 and an N(R$^2$)-containing ring that includes R$^2$ of Chemical Formula 1.

In Chemical Formula 1, Ar$^1$ and Ar$^2$ may be the same or different and may each be represented by one of Chemical Formulas C-4-1 and C-4-2 that each include at least one aromatic ring.

[Chemical Formula C-4-1]

[Chemical Formula C-4-2]

In Chemical Formulas C-4-1 and C-4-2, hydrogen of each aromatic ring may be replaced by a halogen, a cyano group, a C1 to C30 alkyl group, a C1 to C30 alkoxy group, a C1 to C30 haloalkyl group, —SiH$_3$, a C1 to C30 alkylsilyl group, a C6 to C30 aryl group, a C6 to C30 aryloxy group, or a C3 to C30 heteroaryl group, $Y^1$ is O, S, Se, Te, S(=O), S(=O)$_2$, NR$^{a1}$, SiR$^{b1}$R$^{c1}$, or GeR$^{d1}$R$^{e1}$ (wherein R$^{a1}$, R$^{b1}$, R$^{c1}$, R$^{d1}$, and R$^{e1}$ are independently hydrogen, a C1 to C10 alkyl group, a C1 to C10 haloalkyl group, a C1 to C10 alkoxy group, —SiH$_3$, a C1 to C10 alkylsilyl group, —NH$_3$, a C1 to C10 alkylamine group, a C6 to C10 arylamine group, a C6 to C14 aryl group, a C6 to C14 aryloxy group, a C3 to C12 heteroaryl group, a halogen, a cyano group, or a combination thereof), $Y^2$ is O, S, Se, Te, S(=O), S(=O)$_2$, NR$^{a2}$, SiR$^{b2}$R$^{c2}$, GeR$^{d2}$R$^{e2}$, or CR$^{f2}$R$^{g2}$ (wherein R$^{a2}$, R$^{b2}$, R$^{c2}$, R$^{d2}$, R$^{e2}$, R$^{f2}$, and R$^{g2}$ are independently hydrogen, a C1 to C10 alkyl group, a C1 to C10 haloalkyl group, a C1 to C10 alkoxy group, —SiH$_3$, a C1 to C10 alkylsilyl group, —NH$_3$, a C1 to C10 alkylamine group, a C6 to C10 arylamine group, a C6 to C14 aryl group, a C6 to C14 aryloxy group, a C3 to C12 heteroaryl group, a halogen, a cyano group, or a combination thereof), R$^{b1}$ and R$^{c1}$, R$^{d1}$ and R$^{e1}$, R$^{b2}$ and R$^{c2}$, R$^{d2}$ and R$^{e2}$, and R$^{f2}$ and R$^{g2}$ may be independently present or combined with each other to from a spiro ring, an * outside the at least one aromatic ring is a linking point with Ar of Chemical Formula 1, and

*'s inside the at least one aromatic ring are linking portions with an N(R$^1$)-containing ring that includes R$^1$ of Chemical Formula 1 and an N(R$^2$)-containing ring that includes R$^2$ of Chemical Formula 1.

In Chemical Formula 1, Ar$^1$ and Ar$^2$ may be the same or different and may each be represented by one of Chemical Formulas C-5-1 to C-5-8 that each include at least one aromatic ring.

[Chemical Formula C-5-1]

[Chemical Formula C-5-2]

[Chemical Formula C-5-3]

[Chemical Formula C-5-4]

[Chemical Formula C-5-5]

[Chemical Formula C-5-6]

[Chemical Formula C-5-7]

[Chemical Formula C-5-8]

In Chemical Formulas C-5-1 to C-5-8, hydrogen of each aromatic ring may be replaced by a halogen, a cyano group, a C1 to C30 alkyl group (e.g., a C1 to C20 alkyl group or a C1 to C10 alkyl group), a C1 to C30 alkoxy group (e.g., a C1 to C20 alkoxy group or a C1 to C10 alkoxy group), a C1 to C30 haloalkyl group (e.g., a C1 to C20 haloalkyl group or a C1 to C10 haloalkyl group), —SiH$_3$, a C1 to C30 alkylsilyl group (e.g., a C1 to C20 alkylsilyl group or a C1 to C10 alkylsilyl group), a C6 to C30 aryl group (e.g., a C6 to C20 aryl group or a C6 to C10 aryl group), a C6 to C30 aryloxy group (e.g., a C6 to C20 aryloxy group or a C6 to C10 aryloxy group), or a C3 to C30 heteroaryl group (e.g., a C3 to C20 heteroaryl group or a C3 to C10 heteroaryl group), $Y^1$ is O, S, Se, Te, S(=O), S(=O)$_2$, NR$^{a1}$, SiR$^{b1}$R$^{c1}$, or GeR$^{d1}$R$^{e1}$ (wherein R$^{a1}$, R$^{b1}$, R$^{c1}$, R$^{d1}$, and R$^{e1}$ are independently hydrogen, a C1 to C10 alkyl group, a C1 to C10 haloalkyl group, a C1 to C10 alkoxy group, —SiH$_3$, a C1 to C10 alkylsilyl group, —NH$_3$, a C1 to C10 alkylamine group, a C6 to C10 arylamine group, a C6 to C14 aryl group, a C6 to C14 aryloxy group, a C3 to C12 heteroaryl group, a halogen, a cyano group, or a combination thereof), $Y^2$ and $Y^3$ are independently O, S, Se, Te, S(=O), S(=O)$_2$, NR$^{a2}$, SiR$^{b2}$R$^{c2}$, GeR$^{d2}$R$^{e2}$, or CR$^{f2}$R$^{g2}$ (wherein R$^{a2}$, R$^{b2}$, R$^{c2}$, R$^{d2}$, R$^{e2}$, R$^{f2}$, and R$^{g2}$ are independently hydrogen, a C1 to C10 alkyl group, a C1 to C10 haloalkyl group, a C1 to C10 alkoxy group, —SiH$_3$, a C1 to C10 alkylsilyl group, —NH$_3$, a C1 to C10 alkylamine group, a C6 to C10 arylamine group, a C6 to C14 aryl group, a C6 to C14 aryloxy group, a C3 to C12 heteroaryl group, a halogen, a cyano group, or a combination thereof), R$^{b1}$ and R$^{c1}$, R$^{d1}$ and R$^{e1}$, R$^{b2}$ and R$^{c2}$, R$^{d2}$ and R$^{e2}$, and R$^{f2}$ and R$^{g2}$ may be independently present or combined with each other to from a spiro ring (e.g., a C4 to C8 cycloalkyl group, a C5 cycloalkyl group, or a C6 cycloalkyl group), an * outside the at least one aromatic ring is a linking point with Ar of Chemical Formula 1, and

*'s inside the at least one aromatic ring are linking portions with an N(R$^1$)-containing ring that includes R$^1$ of Chemical Formula 1 and an N(R$^2$)-containing ring that includes R$^2$ of Chemical Formula 1.

The near-infrared absorber may absorb light in a near-infrared wavelength region. The near-infrared absorber may have a peak absorption wavelength (Amax) of, for example, greater than or equal to about 750 nm, greater than or equal to about 770 nm, greater than or equal to about 780 nm, greater than or equal to about 790 nm, greater than or equal to about 800 nm, greater than or equal to about 810 nm, greater than or equal to about 820 nm, or greater than or equal to about 830 nm. The near-infrared absorber may have a peak absorption wavelength (Amax) of, for example, about 750 nm to about 3000 nm, about 750 nm to about 2500 nm, about 780 nm to about 2200 nm, about 790 nm to about 2100 nm, about 800 nm to about 2000 nm, about 810 nm to about 2000 nm, about 820 nm to about 2000 nm, or about 830 nm to about 2000 nm.

The near-infrared absorber may exhibit good charge transfer characteristics, and thus, it has good photoelectric conversion characteristics that absorb (e.g., selectively absorb) light and/or convert it (e.g., photoelectrically convert it) into an electrical signal, and thus may be effectively used as a photoelectric conversion material for photoelectric devices. Accordingly, a photoelectric device that includes the near-infrared absorber, for example in an active layer and/or charge auxiliary layer of the photoelectric device (e.g., active layer 30 shown in FIGS. 1 and 2 and/or charge auxiliary layers 40 and 45 shown in FIG. 2) may have improved operational performance and/or efficiency, for example having improved operational performance and/or efficiency with regard to implementing photoelectric conversion of incident near-infrared light, based on including the near-infrared absorber.

The near-infrared absorber has good heat resistance, and thus may prevent or reduce thermal decomposition during deposition, and thus may be repeatedly deposited. The near-infrared absorber may be thermally or vacuum deposited and may be deposited, for example, by sublimation. For example, deposition by sublimation may be confirmed by thermogravimetric analysis (TGA), and at a thermogravimetric analysis at a pressure of less than or equal to about 10 Pa, a temperature at which a 10% weight loss relative to an initial weight may be less than or equal to about 400° C., for example less than or equal to about 390° C., less than or equal to about 380° C., or less than or equal to about 370° C. For example, at a thermogravimetric analysis of the near-infrared absorber at a pressure of less than or equal to about 10 Pa, for example temperature at which a 10% weight loss relative to an initial weight may be about 230° C. to about 400° C.

Some example embodiments provide a near-infrared absorbing/blocking film including the near-infrared absorber.

The near-infrared absorbing/blocking film may be applied to various fields requiring light absorption characteristics in a near-infrared wavelength region.

The near-infrared absorber has both light absorption characteristics and photoelectric characteristics in a near-infrared wavelength region, and thus it may be effectively used as a photoelectric conversion material.

FIG. 1 is a cross-sectional view of a photoelectric device according to some example embodiments.

Referring to FIG. 1, a photoelectric device 100 according to some example embodiments includes a first electrode 10 and a second electrode 20 facing each other and an active layer 30 disposed between the first electrode 10 and the second electrode 20.

A substrate (not shown) may be disposed at the side of the first electrode 10 or the second electrode 20. The substrate may be for example made of (e.g., may at least partially comprise) an inorganic material such as glass; an organic material such as polycarbonate, polymethylmethacrylate, polyethyleneterephthalate, polyethylenenaphthalate, polyamide, polyethersulfone, or a combination thereof; or a silicon wafer. The substrate may be omitted.

One of the first electrode 10 or the second electrode 20 is an anode and the other is a cathode. For example, the first electrode 10 may be a cathode and the second electrode 20 may be an anode.

At least one of the first electrode 10 or the second electrode 20 may be a light-transmitting electrode and the light-transmitting electrode may be for example made of a conductive oxide such as an indium tin oxide (ITO), indium zinc oxide (IZO), zinc oxide (ZnO), tin oxide (SnO$_2$), aluminum tin oxide (AITO), and/or fluorine doped tin oxide (FTO), or a metal thin layer of a single layer or a multilayer. When one of the first electrode 10 and the second electrode 20 is a non-light-transmitting electrode, it may be made of for example an opaque conductor such as aluminum (Al), silver (Ag), or gold (Au). For example, the first electrode 10 and the second electrode 20 may be all light-transmitting electrodes. For example, the second electrode 20 may be a light receiving electrode disposed at a light receiving side.

The active layer 30 is a layer including a p-type semiconductor and an n-type semiconductor configured to provide a pn junction, which is a layer that may produce excitons by receiving light from outside (e.g., an exterior of the active layer 30) and then separating holes and electrons from the produced excitons.

The p-type semiconductor and the n-type semiconductor may be independently a light absorbing material that is configured to absorb (e.g., selectively absorb) light in at least one portion of a wavelength region and the aforementioned near-infrared absorber may be a p-type semiconductor or an n-type semiconductor. For example, the aforementioned near-infrared absorber may be used for a p-type semiconductor and fullerene or a fullerene derivative may be included as an n-type semiconductor. Accordingly, it will be understood that the active layer 30 may at least partially comprise the aforementioned near-infrared absorber (e.g., may include the near-infrared absorber and either fullerene or a fullerene derivative).

Additionally, it will be understood that the active layer 30 may have a peak absorption wavelength (λmax) of, for example, greater than or equal to about 750 nm, greater than or equal to about 770 nm, greater than or equal to about 780 nm, greater than or equal to about 790 nm, greater than or equal to about 800 nm, greater than or equal to about 810 nm, greater than or equal to about 820 nm, or greater than or equal to about 830 nm, or a peak absorption wavelength (λmax) of about 750 nm to about 3000 nm, about 750 nm to about 2500 nm, about 780 nm to about 2200 nm, about 790 nm to about 2100 nm, about 800 nm to about 2000 nm, about 810 nm to about 2000 nm, about 820 nm to about 2000 nm, or about 830 nm to about 2000 nm. The active layer 30, and thus the photoelectric device 100 may have improved near-infrared light absorption characteristics (e.g., may have improved sensitivity to light in a near-infrared wavelength region, improved absorbance of light in the near-infrared wavelength region, etc.) and thus improved photoelectric conversion performance and/or efficiency and/or improved thermal stability based on the active layer including the aforementioned near-infrared absorber. In some example embodiments, the active layer 30 may be a near-infrared absorbing/blocking film that includes the near-infrared absorber.

The active layer 30 may include an intrinsic layer in which the aforementioned near-infrared absorber (e.g., p-type semiconductor) and fullerene or a fullerene derivative (e.g., n-type semiconductor) are co-deposited. Herein, the p-type semiconductor and the n-type semiconductor may be included in a volume ratio of about 1:9 to about 9:1, for example about 2:8 to about 8:2, about 3:7 to about 7:3, about 4:6 to about 6:4, or about 5:5.

The active layer 30 may further include a p-type layer and/or an n-type layer in addition to the intrinsic layer. The p-type layer may include the aforementioned near-infrared absorber (e.g., p-type semiconductor) and the n-type layer may include the aforementioned n-type semiconductor. For example, they may be included in various combinations of p-type layer/I layer, I layer/n-type layer, p-type layer/I layer/n-type layer, and the like.

The photoelectric device 100 may further include an auxiliary layer between the first electrode 10 and the active layer 30 and/or the second electrode 20 and the active layer 30. The auxiliary layer may be a charge auxiliary layer or an optical auxiliary layer.

Figure 2:
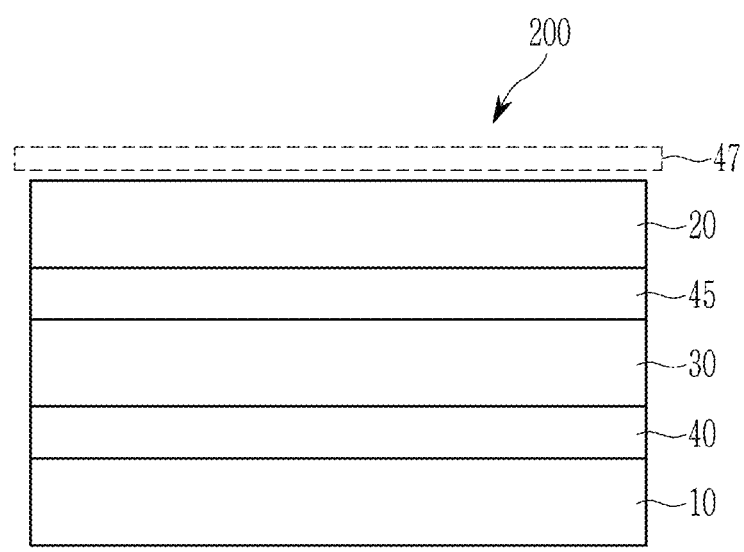
FIG. 2 is a cross-sectional view showing a photoelectric device according to some example embodiments.
Figure 2:
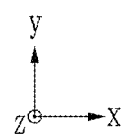

This photoelectric device (e.g., optoelectronic device) is shown in FIG. 2.

FIG. 2 is a cross-sectional view showing a photoelectric device according to some example embodiments.

Referring to FIG. 2, a photoelectric device 200 includes a first electrode 10 and a second electrode 20 facing each other, an active layer 30 between the first electrode 10 and the second electrode 20, a first auxiliary layer 40 between the first electrode 10 and the active layer 30, and a second auxiliary layer 45 between the second electrode 20 and the active layer 30. In some example embodiments, only one of the first auxiliary layer 40 or the second auxiliary layer 45 is included in the photoelectric device 200.

The first auxiliary layer 40 and the second auxiliary layer 45 may each be a charge auxiliary layer that may make holes and electrons separated in the active layer 30 be transported more easily to improve efficiency of the photoelectric device 200.

The charge auxiliary layers may include at least one selected from a hole injection layer (HIL) for facilitating hole injection, a hole transport layer (HTL) for facilitating hole transport, an electron blocking layer (EBL) for preventing electron transport, an electron injection layer (EIL) for facilitating electron injection, an electron transport layer (ETL) for facilitating electron transport, and a hole blocking layer (HBL) for preventing hole transport.

The charge auxiliary layers 40 and/or 45 may include for example an organic material, an inorganic material, or an organic/inorganic material. The organic material may be an organic material having hole or electron characteristics and the inorganic material may be for example a metal oxide such as a molybdenum oxide, a tungsten oxide, or a nickel oxide.

The charge auxiliary layers 40 and 45 may include for example the aforementioned near-infrared absorber. In some example embodiments, the charge auxiliary layers 40 and/or 45 may include the aforementioned near-infrared absorber and the active layer 30 may also include the aforementioned near-infrared absorber. In some example embodiments, the charge auxiliary layers 40 and/or 45 may include the aforementioned near-infrared absorber and the active layer 30 may not include the aforementioned near-infrared absorber. The charge auxiliary layers 40 and/or 45, and thus the photoelectric device 200, may have improved near-infrared light absorption characteristics (e.g., may have improved sensitivity to light in a near-infrared wavelength region, improved absorbance of light in the near-infrared wavelength region, etc.) and thus improved photoelectric conversion performance and/or efficiency, and/or improved thermal stability based on the charge auxiliary layers 40 and/or 45 including the aforementioned near-infrared absorber.

The optical auxiliary layer may be disposed in the light incident direction of the photoelectric device. For example, when the second electrode 20 is a light receiving electrode (e.g., the electrode proximate to a surrounding environment from which light is received at the photoelectric device 200), the optical auxiliary layer may be disposed on the active layer 30. For example, the optical auxiliary layer may be disposed between the second electrode 20 and the active layer 30.

The photoelectric devices 100 and 200 may further include an anti-reflection layer 47 on one surface of the first electrode 10 or the second electrode 20. The anti-reflection layer 47 is disposed at a light incidence side and lowers reflectance of light of incident light and thereby light absorbance is further improved. For example, when light enters from the first electrode 10, the anti-reflection layer 47 may be disposed on the first electrode 10 while when light enters from the second electrode 20, the anti-reflection layer may be disposed under the second electrode 20.

The anti-reflection layer 47 may include, for example a material having a refractive index of about 1.6 to about 2.5 and may include for example at least one of a metal oxide, a metal sulfide, or an organic material having a refractive index within the ranges. The anti-reflection layer 47 may include, for example a metal oxide or chalcogen oxide such as an aluminum-containing oxide, a molybdenum-containing oxide, a tungsten-containing oxide, a vanadium-containing oxide, a rhenium-containing oxide, a niobium-containing oxide, a tantalum-containing oxide, a titanium-containing oxide, a nickel-containing oxide, a copper-containing oxide, a cobalt-containing oxide, a manganesecontaining oxide, a chromium-containing oxide, a tellurium-containing oxide, or a combination thereof; a metal sulfide such as zinc sulfide; or an organic material such as an amine derivative, but is not limited thereto.

In the photoelectric devices 100 and 200, when light enters said photoelectric device 100 and/or 200 and thus enters the active layer 30 thereof from (e.g., via) the first electrode 10 or the second electrode 20 and the active layer 30 thus absorbs the light in a particular (or, alternatively, predetermined) wavelength region, excitons may be generated thereinside. The excitons are separated into holes and electrons in the active layer 30, and the separated holes are transported to an anode that is one of the first electrode 10 or the second electrode 20 and the separated electrons are transported to the cathode that is the other of the first electrode 10 and the second electrode 20 so as to flow (e.g., induce, generate, etc.) a current.

The photoelectric devices 100 and 200 may be applied to (e.g., included in) a solar cell, an image sensor, a photodetector, a photosensor, and an organic light emitting diode (OLED), but example embodiments are not limited thereto.

The photoelectric devices 100 and 200 may be applied to (e.g., included in) an organic sensor. The organic sensor may be an organic CMOS sensor, for example, an organic CMOS infrared light sensor or an organic CMOS image sensor.

In some example embodiments, the photoelectric device 100 may include the near-infrared absorber in any of the elements thereof, including, in addition to or alternative to the active layer 30, one or more of the first electrode 10 or the second electrode 20. In some example embodiments, the photoelectric device 200 may include the near-infrared absorber in any of the elements thereof, including, in addition to or alternative to the active layer 30 and/or one or more of the charge auxiliary layers 40/45, one or more of the first electrode 10 or the second electrode 20.

Figure 3:
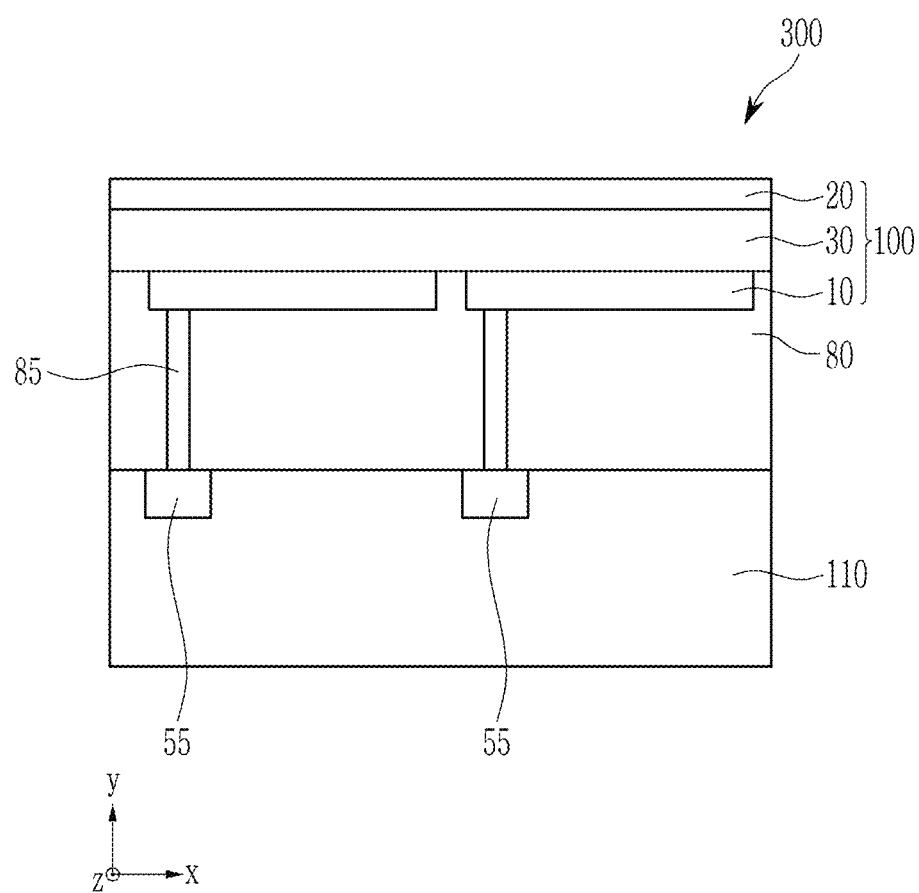
FIG. 3 is a cross-sectional view showing an organic sensor according to some example embodiments.

FIG. 3 is a cross-sectional view showing an organic sensor according to some example embodiments.

The organic sensor 300 according to some example embodiments includes a semiconductor substrate 110, an insulation layer 80, and a photoelectric device 100.

The semiconductor substrate 110 may be a silicon substrate and is integrated with a transmission transistor (not shown) and a charge storage 55. The charge storage 55 may be integrated in each pixel. The charge storage 55 is electrically connected to the photoelectric device 100 that will be described later and information of the charge storage 55 may be transferred by the transmission transistor.

A metal wire (not shown) and a pad (not shown) are formed on the semiconductor substrate 110. In order to decrease signal delay, the metal wire and pad may be made of a metal having low resistivity, for example, aluminum (Al), copper (Cu), silver (Ag), and alloys thereof, but are not limited thereto. Further, it is not limited to the structure, and the metal wire and pad may be disposed under the semiconductor substrate 110.

The insulation layer 80 is formed on the metal wire and pad. The insulation layer 80 may be made of an inorganic insulating material such as a silicon oxide and/or a silicon nitride, or a low dielectric constant (low K) material such as SiC, SiCOH, SiCO, and/or SiOF. The insulation layer 80 has a trench 85 exposing the charge storage 55. The trench 85 may be filled with fillers.

The aforementioned photoelectric device 100 is formed on the insulation layer 80. As described above, the photoelectric device 100 includes a first electrode 10, an active layer 30, and a second electrode 20. Even though a structure in which the first electrode 10, the active layer 30 and the second electrode 20 are sequentially stacked is shown as an example in the drawing, the present disclosure is not limited to this structure, and the second electrode 20, the active layer 30, and the electrodes 10 may be arranged in this order.

The first electrode 10 and the second electrode 20 may both be transparent electrodes, and the active layer 30 may be the same as described above with reference to FIGS. 1 and 2. The active layer 30 may selectively absorb light in a near-infrared wavelength region. Incident light from the side of the second electrode 20 may be photoelectrically converted by mainly absorbing light in a near-infrared wavelength region in the active layer 30. As noted above with reference to FIG. 1, the active layer 30 may include the aforementioned near-infrared absorber and thus may have improved sensitivity to near-infrared light, such that the operational performance and/or efficiency of the organic sensor 300 in absorbing and/or converting incident near-infrared light into electrical signals (e.g., photoelectric conversion performance and/or efficiency) may be improved.

Focusing lens (not shown) may be further formed on the photoelectric device 100. The focusing lens may control a direction of incident light and gather the light in one region. The focusing lens may have a shape of, for example, a cylinder or a hemisphere, but is not limited thereto.

Although the organic sensor to which the photoelectric device 100 of FIG. 1 is applied is illustrated in FIG. 3, the photoelectric device 200 according to FIG. 2 may be equally applied (e.g., included in place of photoelectric device 100 in the organic sensor 300).

The organic sensor according to some example embodiments may be an organic infrared light sensor, for example an iris sensor or a depth sensor.

The iris sensor identifies a person by using unique iris characteristics of every person and specifically, taking an image of an eye of a user within an appropriate distance, processing the image, and comparing it with his/her stored image.

The depth sensor identifies a shape and a location of an object from its three-dimensional information by taking an image of the object within an appropriate distance with a user and processing the image. This depth sensor may be for example used as a face recognition sensor.

Figure 4:
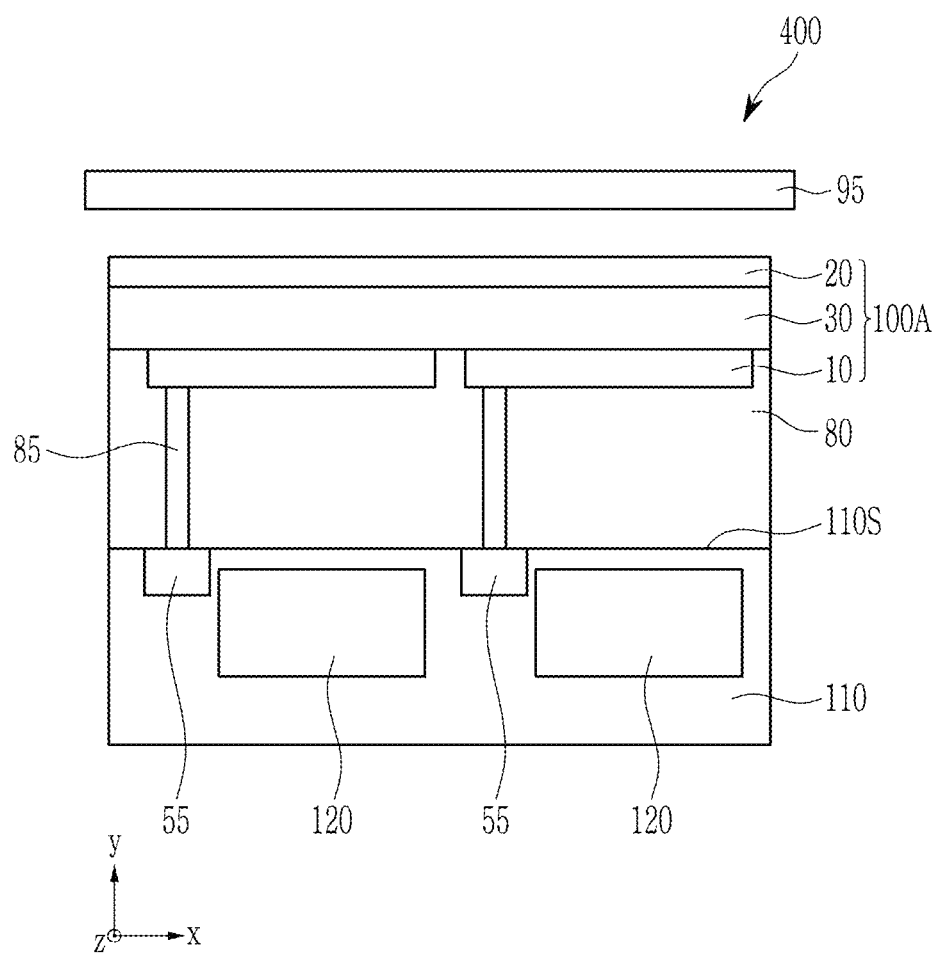
FIG. 4 is a cross-sectional view showing an organic sensor according to some example embodiments.

FIG. 4 is a cross-sectional view showing an organic sensor according to some example embodiments.

The organic sensor according to some example embodiments may include a plurality of sensors having different functions. For example, at least one of the plurality of sensors having different functions may be a biometric sensor, and the biometric sensor may be for example an iris sensor, a depth sensor, a fingerprint sensor, a blood vessel distribution sensor, and the like, but is not limited thereto.

For example, one sensor of the plurality of sensors having different functions may be an iris sensor and another sensor of the plurality of sensors having different functions may be a depth sensor.

For example, a plurality of sensors may include, for example a first infrared light sensor configured to sense (e.g., selectively absorb and/or convert (into electrical signals, e.g., photoelectrically convert)) light in an infrared region having a first wavelength ($\lambda_1$) in an infrared wavelength region and a second infrared light sensor configured to sense (e.g., selectively absorb and/or convert (into electrical signals, e.g., photoelectrically convert)) light in an infrared region having a second wavelength ($\lambda_2$) in an infrared wavelength region (e.g., a same or different infrared wavelength region as the infrared wavelength region including the first wavelength ($\lambda_1$)).

The first wavelength ($\lambda_1$) and the second wavelength ($\lambda_2$) may be for example different in a wavelength region of about 750 nm to about 3000 nm, and for example a difference between the first wavelength ($\lambda_1$) and the second wavelength ($\lambda_2$) may be greater than or equal to about 30 nm, greater than or equal to about 50 nm, greater than or equal to about 70 nm, greater than or equal to about 80 nm, or greater than or equal to about 90 nm.

For example, one of the first wavelength ($\lambda_1$) or the second wavelength ($\lambda_2$) may belong to a wavelength region of about 780 nm to about 900 nm and the other of the first wavelength ($\lambda_1$) or the second wavelength ($\lambda_2$) may belong to a wavelength region of greater than about 900 nm and less than or equal to about 1000 nm.

For example, one of the first wavelength ($\lambda_1$) or the second wavelength ($\lambda_2$) may belong to a wavelength region of about 780 nm to about 840 nm and the other of the first wavelength ($\lambda_1$) or the second wavelength ($\lambda_2$) may belong to a wavelength region of about 910 nm to about 970 nm.

For example, one of the first wavelength ($\lambda_1$) or the second wavelength ($\lambda_2$) may belong to a wavelength region of about 800 nm to about 830 nm and the other of the first wavelength ($\lambda_1$) or the second wavelength ($\lambda_2$) may belong to a wavelength region of about 930 nm to about 950 nm.

For example, one of the first wavelength ($\lambda_1$) or the second wavelength ($\lambda_2$) may belong to a wavelength region of about 805 nm to about 815 nm and the other of the first wavelength ($\lambda_1$) or the second wavelength ($\lambda_2$) may belong to a wavelength region of about 935 nm to about 945 nm.

For example, one of the first wavelength ($\lambda_1$) or the second wavelength ($\lambda_2$) may about 810 nm and the other of the first wavelength ($\lambda_1$) or the second wavelength ($\lambda_2$) may be about 940 nm.

The organic sensor 400 according to some example embodiments includes a dual bandpass filter 95, a first infrared light sensor 100A, an insulation layer 80, and a semiconductor substrate 110 integrated with a second infrared light sensor 120, such that the second infrared light sensor 120 is at least partially embedded within the semiconductor substrate 110. As shown in FIG. 4, the first infrared light sensor 100A and the second infrared light sensor 120 may be stacked, e.g., may overlap in a vertical direction that is perpendicular to the top surface 110S of the semiconductor substrate 110.

As shown in FIG. 4, dual bandpass filter 95 may be disposed on a front side of the organic sensor 400 and may selectively transmit infrared light (e.g., light in an infrared wavelength region) including the first wavelength ($\lambda_1$) and infrared light including the second wavelength ($\lambda_2$) and may block and/or absorb other light. Herein, other light may include light in an ultraviolet (UV) and visible region.

A first infrared light sensor 100A includes a first electrode 10, an active layer 30, and a second electrode 20. As shown in FIG. 4, the first infrared light sensor 100A may be the same as the photoelectric device 100 according to some example embodiments, including the example embodiments described with reference to FIG. 1, but it will be understood that, in some example embodiments, the first infrared light sensor 100A may be the same as the photoelectric device 200 according to some example embodiments, including the example embodiments described with reference to FIG. 2.

As shown in FIG. 4, the second infrared light sensor 120 may be integrated in the semiconductor substrate 110 and may be a photo-sensing device. The semiconductor substrate 110 (e.g., encompassed within a volume space defined by outer surfaces of the semiconductor substrate 110) may be for example a silicon substrate and may be integrated with the second infrared light sensor 120, the charge storage 55, and a transmission transistor (not shown).

The second infrared light sensor 120 may be a photodiode (e.g., a silicon-based photodiode) and may sense (e.g., absorb) entered light, and sensed information is transferred by the transmission transistor. Herein, the light entered into the second infrared light sensor 120 is light that passes through (e.g., is selectively transmitted by) the dual bandpass filter 95 and the first infrared light sensor 100A and may be infrared light in a particular (or, alternatively, predetermined) region including the second wavelength ($\lambda_2$). All infrared light in a particular (or, alternatively, predetermined) region including the first wavelength ($\lambda_1$) may be absorbed by the active layer 30 and may not reach the second infrared light sensor 120. In this case, a separate filter for wavelength selectivity with respect to the light entered into the second infrared light sensor 120 is not separately needed.

However, for the time when all infrared light in a particular (or, alternatively, predetermined) region including the first wavelength ($\lambda_1$) is not absorbed by active layer 30, a filter between the first infrared light sensor 100A and the second infrared light sensor 120 may be further disposed.

Accordingly, in the organic sensor 400, the first infrared light sensor 100A may be understood to include a photoelectric device (e.g., photoelectric device 100 and/or 200) configured to sense (e.g., selectively absorb and/or convert (into electrical signals, e.g., photoelectrically convert)) light in a first near-infrared wavelength region of incident light (e.g., a first near-infrared wavelength region including the first wavelength ($\lambda_1$)), and the second infrared light sensor 120 may be understood to be an additional sensor configured to selectively absorb and/or convert (into electrical signals, e.g., photoelectrically convert) light in a separate wavelength region of incident light (e.g., a second near-infrared wavelength region that is different from the first near-infrared wavelength region and includes the second wavelength ($\lambda_2$) and excludes the first wavelength ($\lambda_1$)).

The organic sensor according to some example embodiments may include two infrared light sensors respectively performing separately functions and thus may work as a combination sensor. In addition, two sensors performing separately functions are stacked in each pixel, and thus the number of pixel performing functioning of each sensor is twice increased while maintaining a size and resultantly, sensitivity may be much improved.

As noted above with reference to FIG. 1, the active layer 30, or any portion of the photoelectric device 100 and/or 200, may include the aforementioned near-infrared absorber and thus may have improved sensitivity to and/or absorbance of near-infrared light, such that the operational performance and/or efficiency of the organic sensor 400 in absorbing and/or photoelectrically converting incident near-infrared light into electrical signals (e.g., photoelectric conversion performance and/or efficiency) may be improved. In some example embodiments, the second infrared light sensor 120 may include the aforementioned near-infrared absorber and thus may have improved sensitivity to and/or absorbance of near-infrared light, such that the operational performance and/or efficiency of the organic sensor 400 in absorbing and/or converting incident near-infrared light into electrical signals (e.g., photoelectric conversion performance and/or efficiency) may be improved.

Figure 5:
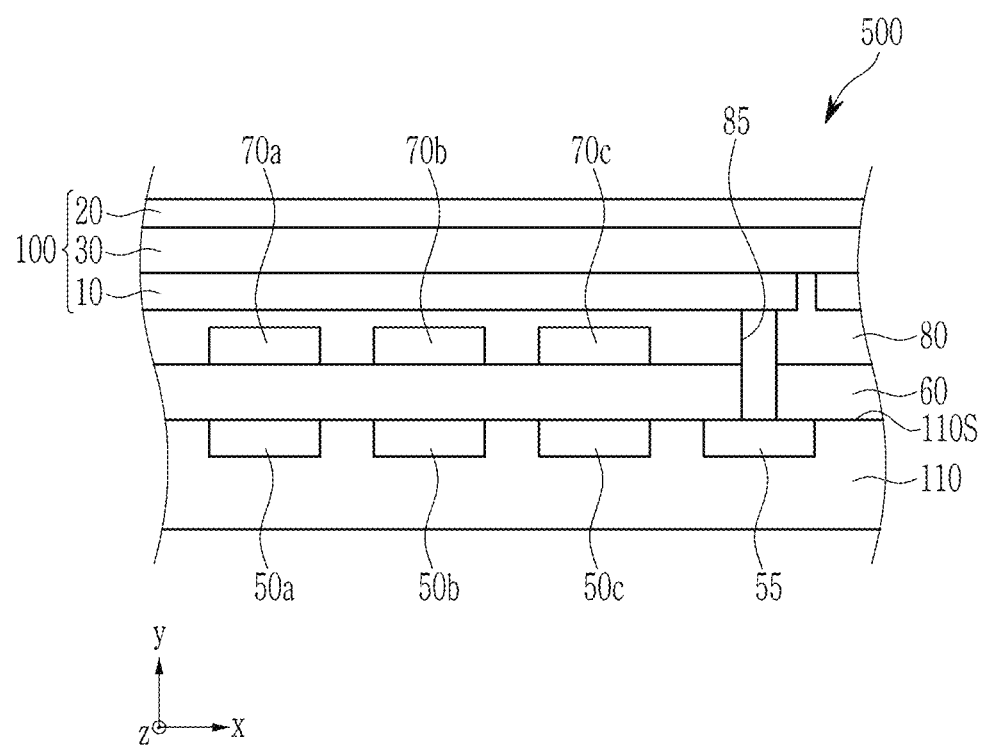
FIG. 5 is a cross-sectional view showing an organic sensor according to some example embodiments.

FIG. 5 is a cross-sectional view showing an example of an organic sensor according to some example embodiments.

An organic sensor according to some example embodiments may be an organic CMOS image sensor.

Referring to FIG. 5, an organic sensor 500 according to some example embodiments includes a semiconductor substrate 110 integrated with photo-sensing devices (e.g., photodiodes, including silicon-based photodiodes) 50a, 50b, and 50c, a transmission transistor (not shown), and a charge storage 55, a lower insulation layer 60, color filter layers 70a, 70b, and 70c, an upper insulation layer 80, and a photoelectric device 100.

The semiconductor substrate 110 may be integrated with photo-sensing devices 50a, 50b, and 50c, such that the photo-sensing devices 50a, 50b, and 50c are at least partially embedded within the semiconductor substrate 110 and are vertically overlapped by the photoelectric device 100 in the vertical direction that is perpendicular to the top surface 110S, a transmission transistor (not shown), and a charge storage 55. The photo-sensing devices 50a, 50b, and 50c may be photodiodes (e.g., silicon-based photodiodes) that may be configured to sense (e.g., selectively absorb and/or convert (into electric signals, e.g., photoelectrically convert)) light in different visible wavelength regions.

The photo-sensing devices 50a, 50b, and 50c, the transmission transistor, and/or the charge storage 55 may be integrated in each pixel. For example, the photo-sensing device 50a may be included in a red pixel, the photo-sensing device 50b may be included in a green pixel, and the photo-sensing device 50c may be included in a blue pixel.

The photo-sensing devices 50a, 50b, and 50c sense (e.g., selectively absorb and/or convert (into electrical signals, e.g., photoelectrically convert)) incident light, the information sensed by the photo-sensing devices may be transferred by the transmission transistor, the charge storage 55 is electrically connected to the photoelectric device 100, and the information of the charge storage 55 may be transferred by the transmission transistor.

A metal wire (not shown) and a pad (not shown) are formed on the semiconductor substrate 110. In order to decrease signal delay, the metal wire and pad may be made of a metal having low resistivity, for example, aluminum (Al), copper (Cu), silver (Ag), and alloys thereof, but are not limited thereto. Further, it is not limited to the structure, and the metal wire and pad may be disposed under the photo-sensing devices 50a and 50b.

The lower insulation layer 60 is formed on the metal wire and the pad. The lower insulation layer 60 may include a same or different material composition as the insulation layer 80.

Color filters 70a, 70b, and 70c are formed on the lower insulation layer 60. The color filters 70a, 70b, and 70c includes a blue filter 70a formed in a blue pixel, a red filter 70b formed in a red pixel, and a green filter 70c formed in a green pixel.

The insulation layer (also referred to as upper insulation layer) 80 is formed on the color filters 70a, 70b, and 70c. The insulation layer 80 eliminates steps caused by the color filters 70a, 70b, and 70c and planarizes the surface.

The aforementioned photoelectric device 100 is formed on the insulation layer 80. As described above, the photoelectric device 100 includes a first electrode 10, an active layer 30, and a second electrode 20. Even though a structure in which the first electrode 10, the active layer 30 and the second electrode 20 are sequentially stacked is shown as an example in the drawing, the present disclosure is not limited to this structure, and the second electrode 20, the active layer 30, and the first electrode 10 may be arranged in this order.

The first electrode 10 and the second electrode 20 may both be transparent electrodes, and the active layer 30 is the same as described above. The active layer 30 may selectively absorb and/or convert (into electrical signals, e.g., photoelectrically convert) light in a near-infrared wavelength region. As noted above with regard to photoelectric devices 100 and 200, any portion of the photoelectric device 100 (e.g., first electrode 10, second electrode 20, and/or active layer 30) may include the aforementioned near-infrared absorber.

Incident light from the side of the second electrode 20 may be photoelectrically converted by mainly absorbing light in a near-infrared wavelength region in the active layer 30. Light in the remaining wavelength region may pass through the first electrode 10 and the color filters 70a, 70b, and 70c, the light in a red wavelength region passing through the color filter 70a may be sensed by the photo-sensing device 50a, the light in a green wavelength region passing through the color filter 70b may be sensed by the photo-sensing device 50b, and the light in a blue wavelength region passing through the color filter 70c may be sensed by the photo-sensing device 50c.

As noted above with reference to FIG. 1, the active layer 30 may include the aforementioned near-infrared absorber and thus may have improved sensitivity to near-infrared light, such that the operational performance and/or efficiency of the organic sensor 500 in absorbing and/or converting incident near-infrared light into electrical signals (e.g., photoelectric conversion performance and/or efficiency) may be improved.

Accordingly, where an organic sensor includes a photoelectric device that includes the near-infrared absorber and is configured to selectively absorb and/or convert (into electrical signals, e.g., photoelectrically convert) light in a first near-infrared wavelength region, the organic sensor may include an additional sensor that includes a plurality of photodiodes (e.g., photo-sensing devices 50a, 50b, 50c) at least partially embedded within the semiconductor substrate and configured to selectively absorb and/or convert (into electrical signals, e.g., photoelectrically convert) light in separate visible wavelength regions (e.g., red, blue, and/or green light).

Figure 6:
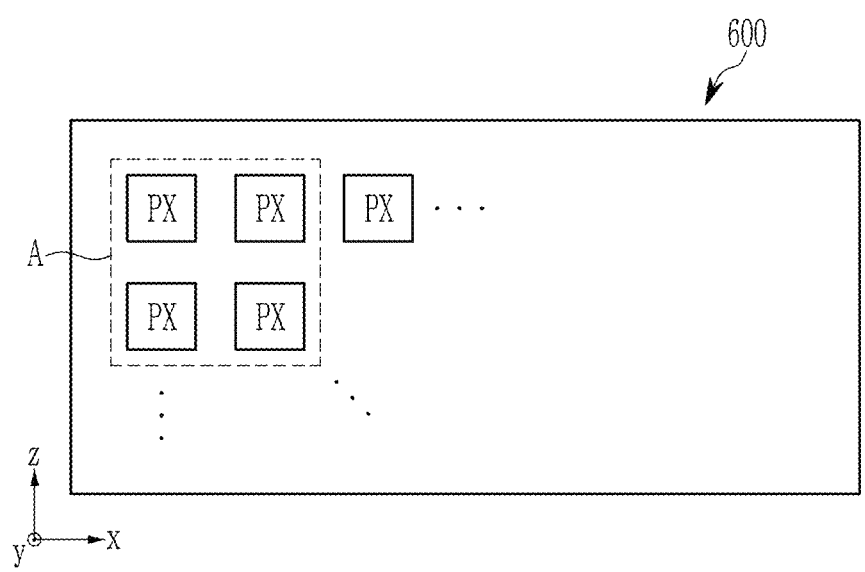
FIG. 6 is a schematic view showing an example of a pixel array of an organic sensor according to some example embodiments.

FIG. 6 is a schematic view showing an example of a pixel array of an organic sensor according to some example embodiments.

Referring to FIG. 6, an organic sensor 600 according to some example embodiments includes a plurality of pixels (PX) and the plurality of pixels (PX) may have a matrix array repeatedly arranged along rows and columns. The plurality of pixels (PX) may form ("at least partially comprise") a unit pixel group (A) of for example a 2×2 array of pixels as shown in FIG. 6. However, an arrangement of the pixels are not limited thereto but variously modified, and the unit pixel group (A) may be variously modified into different arrays of pixels, including a 3×3 array, a 4×4 array, or the like, besides the 2×2 array.

At least a part of the pixels may include a plurality of sensors having different functions inside one pixel, and the plurality of sensors may be stacked therein. In some example embodiments, each pixel (PX) may include two or more organic sensors that are configured to sense (e.g., absorb) light in different wavelength regions ("wavelength spectra of light") in relation to each other, and the organic sensors configured to sense the light in different wavelength regions each other may be stacked in a direction that is perpendicular (e.g., perpendicular within manufacturing tolerances and/or material tolerances) to a top surface 110S of a substrate of the organic sensor 600, as shown in at least FIG. 7 (e.g., a y direction).

Herein, the light of the different wavelength regions may be respectively selected from a visible wavelength region; an infrared wavelength region including a near-infrared wavelength region; and an ultraviolet (UV) wavelength region.

It will be understood that any of the organic sensors according to any of the example embodiments herein may have the pixel array structure of organic sensor 600 as shown in FIG. 6.

Figure 7:
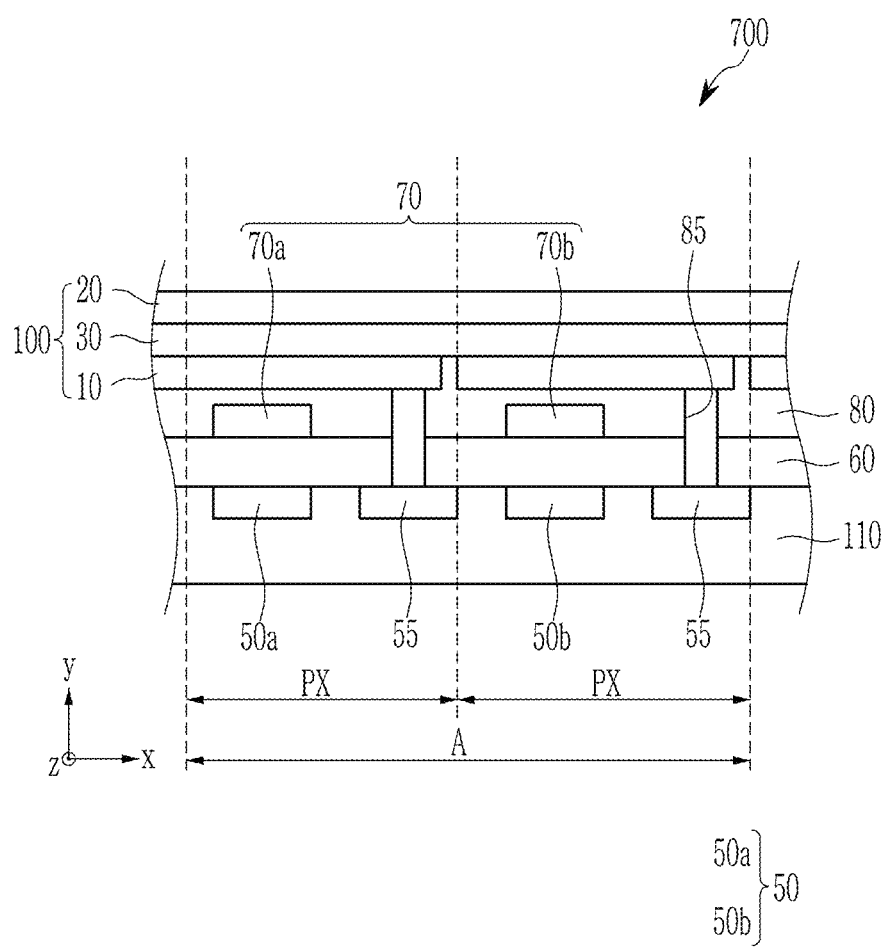
FIG. 7 is a cross-sectional view showing an organic sensor according to some example embodiments.

FIG. 7 is a cross-sectional view showing an organic sensor according to some example embodiments.

Referring to FIG. 7, an organic sensor 700 according to some example embodiments includes a semiconductor substrate 110 integrated with a visible light sensor 50 that includes photo-sensing devices 50a and 50b, a transmission transistor (not shown), and a charge storage 55; a lower insulation layer 60; a color filter layer 70; an insulation layer 80 (also referred to as an upper insulation layer when present with the lower insulation layer 60 in a same organic sensor); and a photoelectric device 100.

The semiconductor substrate 110 may be a silicon substrate, and is integrated with the photo-sensing devices 50a and 50b, the transmission transistor (not shown), and the charge storage 55. The photo-sensing devices 50a and 50b may be photodiodes (e.g., silicon-based photodiodes).

The photo-sensing devices 50a and 50b may sense light, the information sensed by the photo-sensing devices may be transferred by the transmission transistor, the charge storage 55 is electrically connected to the photoelectric device 100, and the information of the charge storage 55 may be transferred by the transmission transistor.

A metal wire (not shown) and a pad (not shown) are formed on the semiconductor substrate 110. In order to decrease signal delay, the metal wire and pad may be made of a metal having low resistivity, for example, aluminum (Al), copper (Cu), silver (Ag), and alloys thereof, but is not limited thereto. However, it is not limited to the structure, and the metal wire and pad may be disposed under the photo-sensing devices 50a and 50b.

The lower insulation layer 60 is formed on the metal wire and the pad. The lower insulation layer 60 may be made of an inorganic insulating material such as a silicon oxide and/or a silicon nitride, or a low dielectric constant (low K) material such as SiC, SiCOH, SiCO, and SiOF. The lower insulation layer 60 has a trench exposing the charge storage 55. The trench may be filled with fillers.

A color filter layer 70 is formed on the lower insulation layer 60. The color filter layer 70 includes a blue filter 70a formed in the blue pixel and a red filter 70b formed in the red pixel. In the example embodiments shown in FIG. 7, a green filter is not included, but a green filter may be further included.

The insulation layer 80 is formed on the color filter layer 70. The insulation layer 80 eliminates a step caused by the color filter layer 70 and smoothens the surface. The insulation layer 80 and lower insulation layer 60 may include a contact hole (not shown) exposing a pad, and a through hole (e.g., trench 85) exposing the charge storage 55 of a green pixel.

The photoelectric device 100 is formed on the insulation layer 80. The photoelectric device 100 includes a first electrode 10 and a second electrode 20 facing each other and an active layer 30 disposed between the first electrode 10 and the second electrode 20. The photoelectric device 100 may be the same as the photoelectric device 100 of FIG. 1.

In some example embodiments, the photoelectric device 100 of FIG. 7 may be replaced with the photoelectric device 200 of FIG. 2.

The first electrode 10 and the second electrode 20 may be all light-transmitting electrodes and the active layer 30 may selectively absorb and/or convert (into electrical signals, e.g., photoelectrically convert) light in a near-infrared wavelength region. In some example embodiments, including the example embodiments shown in FIG. 7, the active layer 30 may additionally selectively absorb and/or convert (into electrical signals, e.g., photoelectrically convert) light in a visible wavelength region (e.g., green light).

Focusing lens (not shown) may be further formed on the photoelectric device 100. The focusing lens may control a direction of incident light and gather the light in one region. The focusing lens may have a shape of, for example, a cylinder or a hemisphere, but is not limited thereto.

In FIG. 7, a structure where the photoelectric device 100 selectively absorbing light in a near-infrared wavelength region is stacked on the semiconductor substrate 110 is illustrated, but the present disclosure is not limited thereto. Among the light incident on the organic sensor 700 at a top surface of the photoelectric device 100, at least light in a near-infrared wavelength region may be mainly absorbed in the active layer 30 and photoelectrically converted, and light in a visible (e.g., blue, green, and/or red) wavelength region may pass through the first electrode 10 and be sensed by the photo-sensing devices 50a and 50b.

Figure 8:
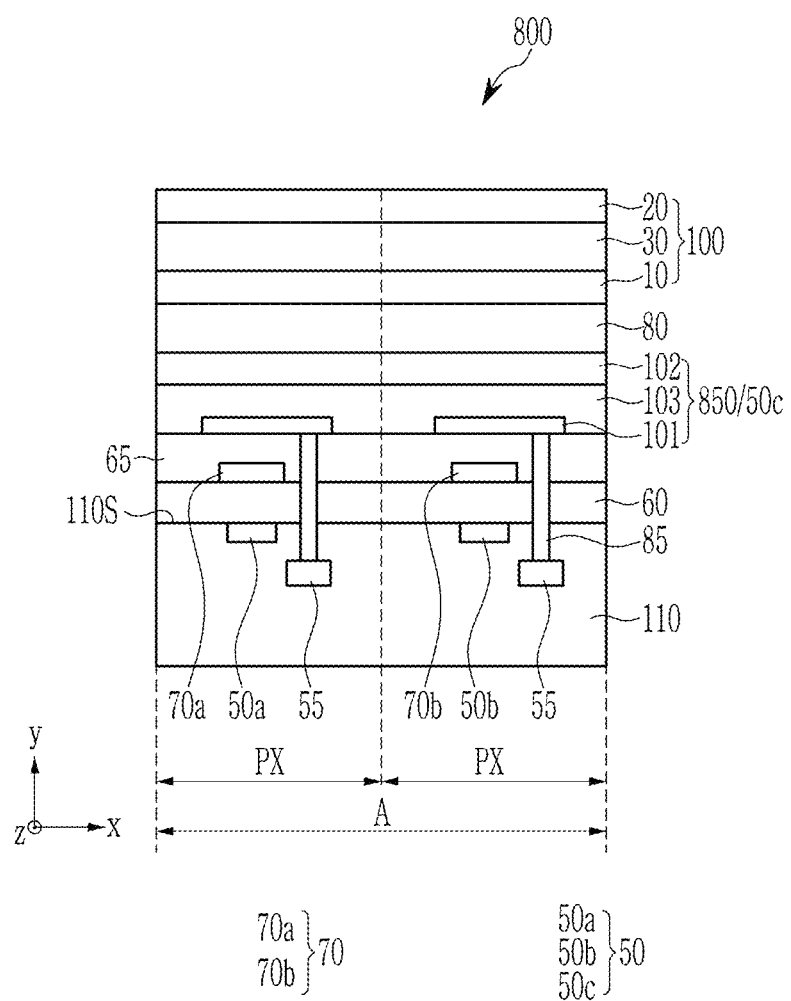
FIG. 8 is a cross-sectional view showing an organic sensor according to some example embodiments.

FIG. 8 is a cross-sectional view showing an organic sensor according to some example embodiments.

Referring to FIG. 8, the organic sensor 800 according to some example embodiments includes a visible light sensor 50, and the photoelectric device 100 as described above.

Referring to FIG. 8, in the organic sensor 800 according to some example embodiments, the visible light sensor 50 may be a combination of a photodiode integrated in the semiconductor substrate 110 and a photoelectric device disposed on the semiconductor substrate 110, and the photoelectric device 100 may be a separate photoelectric device.

Accordingly, where an organic sensor includes a photoelectric device (e.g., 100) that includes the near-infrared absorber and is configured to selectively absorb and/or convert (into electrical signals, e.g., photoelectrically convert) light in a first near-infrared wavelength region, and an additional sensor (e.g., 50a and/or 50b) configured to selectively absorb and/or convert (into electrical signals, e.g., photoelectrically convert) light in a separate wavelength region of incident light, the organic sensor may further include an additional photoelectric device (e.g., 50c) on the semiconductor substrate, the additional photoelectric device being between the photoelectric device 100 and the semiconductor substrate 110, the additional photoelectric device configured to selectively absorb and/or convert (into electrical signals, e.g., photoelectrically convert) light in an additional wavelength region of incident light that is different from the first near-infrared wavelength region and different from the separate wavelength region(s) absorbed by the additional sensor 50a and/or 50b.

In the semiconductor substrate 110, the blue photo-sensing device 50a, the red photo-sensing device 50b, the charge storage 55, and a transmission transistor (not shown) are integrated. The blue photo-sensing device 50a and the red photo-sensing device 50b are photodiodes (e.g., silicon-based photodiodes) and spaced apart from each other in a horizontal direction of the semiconductor substrate 110. The blue photo-sensing device 50a is integrated in a blue pixel, and the red photo-sensing device 50b is integrated in a red pixel.

On the semiconductor substrate 110, the lower insulation layer 60 and the color filter layer 70 are formed. The color filter layer 70 includes a blue filter 70a overlapped with the blue photo-sensing device 50a and a red filter 70b overlapped with the red photo-sensing device 50b.

An intermediate insulation layer 65 is formed on the color filter layer 70. The lower insulation layer 60 and the intermediate insulation layer 65 may have a through hole (e.g., trench 85) exposing the charge storage 55. The through hole (e.g., trench 85) may be filled with fillers. At least one of the lower insulation layer 60 or intermediate insulation layer 65 may be omitted.

On the intermediate insulation layer 65, the additional photoelectric device 850 is formed. In the example embodiments shown in FIG. 8, the additional photoelectric device 850 is also green sensor 50c, but it will be understood that in some example embodiments the additional photoelectric device 850 may be configured to sense (e.g., selectively absorb and/or convert (into electrical signals, e.g., photoelectrically convert)) light in a wavelength region that is different from the green wavelength region and may be a non-visible wavelength region (e.g., a second near-infrared wavelength region) that is different from the first near-infrared wavelength region sensed by the photoelectric device 100. The additional photoelectric device 850 includes a first electrode (lower electrode) 101 and a second electrode (upper electrode) 102 facing each other, and an active layer 103 between the first electrode 101 and the second electrode 102. One of the first electrode 101 or the second electrode 102 is an anode and the other is a cathode.

Both of the first electrode 101 and the second electrode 102 may be a light-transmitting electrode, and the light-transmitting electrode may be made of, in some example embodiments, a transparent conductor such as indium tin oxide (ITO) or indium zinc oxide (IZO), or may be a metal thin layer having a thin thickness of several nanometers to several tens of nanometers or a metal thin layer having a thin thickness of several nanometers to several tens of nanometers doped with a metal oxide.

The active layer 103 may have a composition similar to that of the active layer 30 of photoelectric device 100 and/or 200, and may include the near-infrared absorber. The active layer 103 may be a photoelectric conversion layer configured to selectively absorb and/or convert (into electrical signals, e.g., photoelectrically convert) light in at least a portion of a wavelength region (e.g., wavelength spectrum of the light). The active layer 103 may for example convert at least a portion of light in a green wavelength region (hereinafter, referred to as "green light"), light in a blue wavelength region (hereinafter, referred to as "blue light"), light in a red wavelength region (hereinafter, referred to as "red light"), light in an infrared wavelength region (hereinafter, referred to as "infrared light"), light in an ultraviolet wavelength region (hereinafter, referred to as "ultraviolet light"), or any combination thereof, or the like, into an electrical signal.

For example, the active layer 103 may be configured to selectively absorb and/or convert (into electrical signals, e.g., photoelectrically convert) at least one of the green light, the blue light, the red light, the infrared light, or the ultraviolet light. Herein, the selective absorption of at least one from the green light, the blue light, the red light, the infrared light, or the ultraviolet light means that a light-absorption spectrum has a peak absorption wavelength (Amax) in one of about 500 nm to about 600 nm, greater than or equal to about 380 nm and less than about 500 nm, greater than about 600 nm and less than or equal to about 700 nm, and greater than about 700 nm and less than or equal to about 3000 nm and a light-absorption spectrum in the corresponding wavelength region is remarkably higher than those in the other wavelength regions.

The active layer 103 may include at least one p-type semiconductor and at least one n-type semiconductor which form a pn junction and may produce excitons by receiving light from outside and then separate the produced excitons into holes and electrons. The p-type semiconductor and the n-type semiconductor may be independently light-absorbing materials, and for example at least one of the p-type semiconductor or the n-type semiconductor may be an organic light-absorbing material. For example, at least one of the p-type semiconductor or the n-type semiconductor may be a wavelength-selective light-absorbing material that selectively absorbs light in a particular (or, alternatively, predetermined) wavelength region, and for example at least one of the p-type semiconductor or the n-type semiconductor may be a wavelength-selective organic light-absorbing material.

The p-type semiconductor and the n-type semiconductor may have a peak absorption wavelength (Amax) in the same wavelength region or in a different wavelength region, among a green wavelength region, a blue wavelength region, a red wavelength region, and an infrared wavelength region. For example, the p-type semiconductor may be an organic material having a core structure including an electron donating moiety, a pi conjugation linking group, and an electron accepting moiety. The p-type semiconductor may be for example represented by Chemical Formula 2, but is not limited thereto.

EDG-HA-EAG            [Chemical Formula 2]

In Chemical Formula 2, HA may be a C2 to C30 heterocyclic group having at least one of S, Se, Te, or Si, EDG may be an electron-donating group, and EAG may be an electron accepting group. For example, the p-type semiconductor represented by Chemical Formula 2 may be for example represented by Chemical Formula 2A.

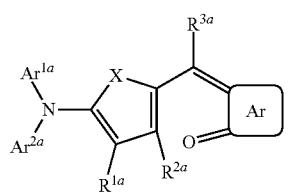

[Chemical Formula 2A]

In Chemical Formula 2A, X may be S, Se, Te, SO, $SO_2$, or $SiR^aR^b$, Ar may be a substituted or unsubstituted C6 to C30 arylene group, a substituted or unsubstituted C3 to C30 heterocyclic group, or a fused ring of the foregoing two or more, $Ar^{1a}$ and $Ar^{2a}$ may independently be a substituted or unsubstituted C6 to C30 aryl group or a substituted or unsubstituted C3 to C30 heteroaryl group, $Ar^{1a}$ and $Ar^{2a}$ may independently be present alone or may be linked with each other to form a fused ring, and $R^{1a}$ to $R^{3a}$, $R^a$, and $R^b$ may independently be hydrogen, deuterium, a substituted or unsubstituted C1 to C30 alkyl group, a substituted or unsubstituted C6 to C30 aryl group, a substituted or unsubstituted C3 to C30 heteroaryl group, a substituted or unsubstituted C1 to C6 alkoxy group, a halogen, or a cyano group.

For example, in Chemical Formula 2A, $Ar^{1a}$ and $Ar^{2a}$ may independently be one of a substituted or unsubstituted phenyl group, a substituted or unsubstituted naphthyl group, a substituted or unsubstituted anthracenyl group, a substituted or unsubstituted phenanthrenyl group, a substituted or unsubstituted pyridinyl group, a substituted or unsubstituted pyridazinyl group, a substituted or unsubstituted pyrimidinyl group, a substituted or unsubstituted pyrazinyl group, a substituted or unsubstituted quinolinyl group, a substituted or unsubstituted isoquinolinyl group, a substituted or unsubstituted naphthyridinyl group, a substituted or unsubstituted cinnolinyl group, a substituted or unsubstituted quinazolinyl group, a substituted or unsubstituted phthalazinyl group, a substituted or unsubstituted benzotriazinyl group, a substituted or unsubstituted pyridopyrazinyl group, a substituted or unsubstituted pyridopyrimidinyl group, and a substituted or unsubstituted pyridopyridazinyl group. For example, $Ar^{1a}$ and $Ar^{2a}$ of Chemical Formula 2A may be linked with each other to form a ring or for example, $Ar^{1a}$ and $Ar^{2a}$ may be linked with each other by one of a single bond, $-(CR^gR^h)_{n2}-$ (n2 is 1 or 2), $-O-$, $-S-$, $-Se-$, $-N=$, $-NR^i-$, $-SiR^jR^k-$, or $-GeR^lR^m-$ to form a ring. Herein, $R^g$ to $R^m$ may independently be hydrogen, a substituted or unsubstituted C1 to C30 alkyl group, a substituted or unsubstituted C6 to C30 aryl group, a substituted or unsubstituted C3 to C30 heteroaryl group, a substituted or unsubstituted C1 to C6 alkoxy group, a halogen, or a cyano group.

For example, the p-type semiconductor represented by Chemical Formula 2 may be for example represented by Chemical Formula 2B.

[Chemical Formula 2B]

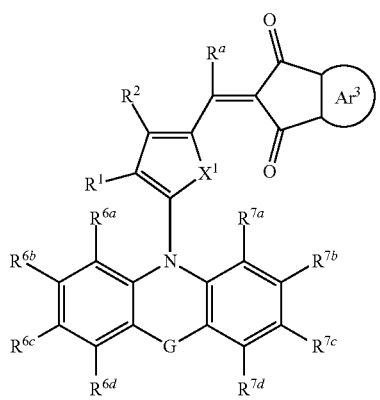

In Chemical Formula 2B, $X^1$ may be Se, Te, O, S, SO, or $SO_2$, $Ar^3$ may be a substituted or unsubstituted C6 to C30 arylene group, a substituted or unsubstituted C3 to C30 heterocyclic group, or a fused ring of the foregoing two or more, $R^1$ to $R^3$ may independently be one of hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group, a cyano-containing group, or a combination thereof, G may be one of a single bond, $-O-$, $-S-$, $-Se-$, $-N=$, $-(CR^fR^g)_k-$, $-NR^h-$, $-SiR^iR^j-$, $-GeR^kR^l-$, $-(C(R^m)=C(R^n))-$, or $SnR^oR^p$, wherein $R^f$, $R^g$, $R^h$, $R^i$, $R^j$, $R^k$, $R^l$, $R^m$, $R^n$, $R^o$, and $R^p$ may independently be one of hydrogen, a halogen, a substituted or unsubstituted C1 to C10 alkyl group, a substituted or unsubstituted C1 to C10 alkoxy group, and a substituted or unsubstituted C6 to C12 aryl group, $R^f$ and $R^g$, $R^i$ and $R^j$, $R^k$ and $R^l$, $R^m$ and $R^n$, and $R^o$ and $R^p$ may independently be present alone or may be linked with each other to provide a ring, and k may be 1 or 2, $R^{6a}$ to $R^{6d}$ and $R^{7a}$ to $R^{7d}$ may independently be one of hydrogen, a substituted or unsubstituted C1 to C30 alkyl group, a substituted or unsubstituted C6 to C30 aryl group, a substituted or unsubstituted C3 to C30 heteroaryl group, a halogen, a cyano group, a cyano-containing group, or a combination thereof, $R^{6a}$ to $R^{6d}$ may independently be present alone or adjacent two thereof may be linked with each other to form a fused ring, and $R^{7a}$ to $R^{7d}$ may independently be present alone or adjacent two thereof may be linked with each other to form a fused ring.

For example, $Ar^3$ of Chemical Formula 2B may be benzene ring, naphthylene ring, anthracene ring, thiophene ring, selenophene ring, tellurophene ring, pyridine ring, pyrimidine ring, or a fused ring of the foregoing two or more. The n-type semiconductor may be for example fullerene or a fullerene derivative, but is not limited thereto.

The active layer 103 may be an intrinsic layer (an I layer) wherein the p-type semiconductor and the n-type semiconductor are blended as a bulk heterojunction. Herein, the p-type semiconductor and the n-type semiconductor may be blended in a volume ratio of about 1:9 to about 9:1, for example about 2:8 to about 8:2, about 3:7 to about 7:3, about 4:6 to about 6:4, or about 5:5. The active layer 103 may include a bi-layer including a p-type layer including the aforementioned p-type semiconductor and an n-type layer including the aforementioned n-type semiconductor. Herein, a thickness ratio of the p-type layer and the n-type layer may be about 1:9 to about 9:1, for example about 2:8 to about 8:2, about 3:7 to about 7:3, about 4:6 to about 6:4, or about 5:5. The active layer 103 may further include a p-type layer and/or an n-type layer in addition to the intrinsic layer. The p-type layer may include the aforementioned p-type semiconductor and the n-type layer may include the aforementioned n-type semiconductor. For example, they may be included in various combinations of p-type layer/I layer, I layer/n-type layer, p-type layer/I layer/n-type layer, and the like.

In the example embodiments shown in FIG. 8, the active layer 103 is configured to selectively absorb and/or convert (into electrical signals, e.g., photoelectrically convert) green light, but example embodiments are not limited thereto, and in some example embodiments the active layer 103 may selectively absorb and/or convert (into electrical signals, e.g., photoelectrically convert) blue light, red light, or any visible wavelength region of light, or any non-visible wavelength region of light (e.g., a second wavelength region of near-infrared light that is selectively transmitted by the photoelectric device 100).

Figure 9:
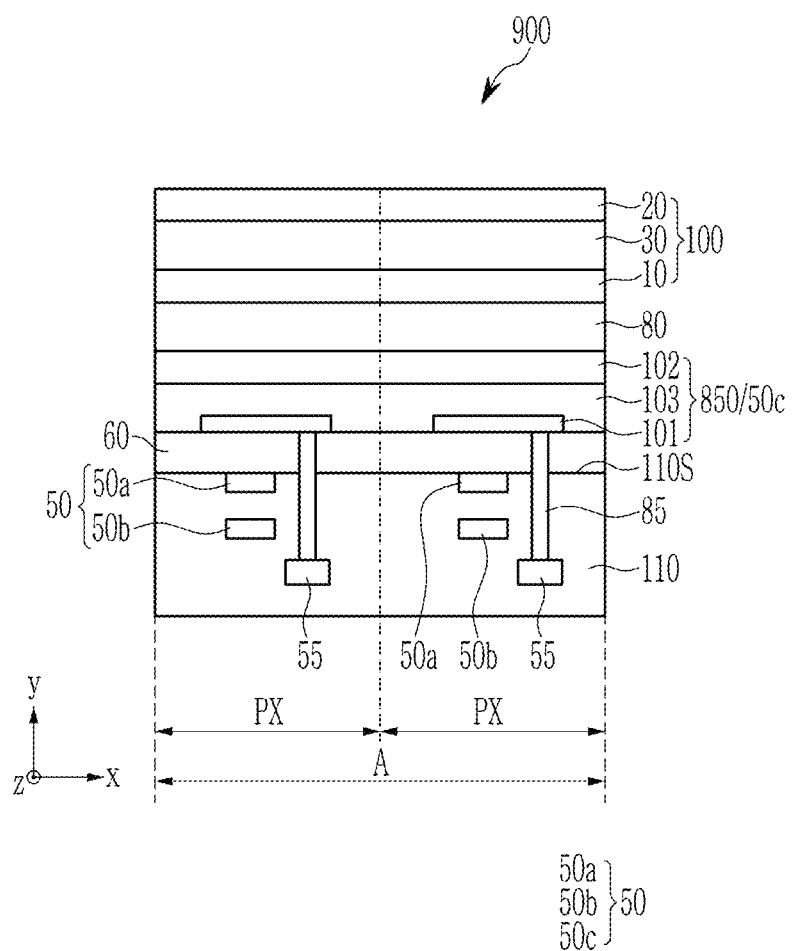
FIG. 9 is a cross-sectional view showing an organic sensor according to some example embodiments.

FIG. 9 is a cross-sectional view showing an organic sensor according to some example embodiments.

Referring to FIG. 9, the organic sensor 900 according to some example embodiments includes the visible light sensor 50, and the photoelectric device 100 like that of some example embodiments. The visible light sensor 50 includes the blue photo-sensing device 50a and the red photo-sensing device 50b integrated in the semiconductor substrate 110 and an additional photoelectric device 850 that includes a green sensor 50c disposed on the semiconductor substrate 110, wherein the blue photo-sensing device 50a and the red photo-sensing device 50b may be photodiodes (e.g., silicon-based photodiodes), and the additional photoelectric device 850 may be a green sensor 50c that may be the same as, or different than, the green sensor 50c shown in FIG. 8. The additional photoelectric device 850 includes a first electrode 101, active layer 103, and a second electrode (upper electrode) 102, and the photoelectric device 100 includes a first electrode 10, an active layer 30, and a second electrode 20.

However, in the organic sensor 900 according to some example embodiments, the blue photo-sensing device 50a and the red photo-sensing device 50b integrated in the semiconductor substrate 110 are stacked in a vertical direction (e.g., perpendicular to the top surface 110S of the semiconductor substrate 110). The blue photo-sensing device 50a and the red photo-sensing device 50b may be configured to selectively absorb and/or convert (into electrical signals, e.g., photoelectrically convert) light in each wavelength region depending on a stacking depth and thus sense it. In other words, the red photo-sensing device 50b configured to selectively absorb and/or convert (into electrical signals, e.g., photoelectrically convert) red light in a long wavelength region is disposed deeper from the surface of the semiconductor substrate 110 than the blue photo-sensing device 50a configured to selectively absorb and/or convert (into electrical signals, e.g., photoelectrically convert) blue light in a short wavelength region. In this way, the color filter layer 70 may be omitted by separating absorption wavelengths depending on the stacking depth.

Figure 10:
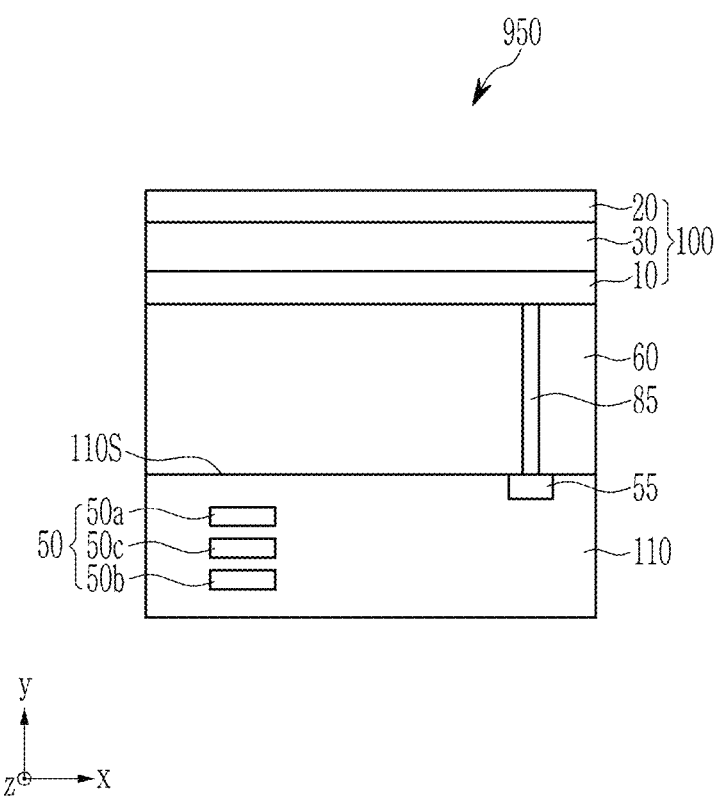
FIG. 10 is a cross-sectional view showing an organic sensor according to some example embodiments.

FIG. 10 is a cross-sectional view showing an organic sensor according to some example embodiments.

Referring to FIG. 10, the organic sensor 950 according to some example embodiments includes the visible light sensor 50, and the photoelectric device 100 like that of some example embodiments. The visible light sensor 50 includes the blue photo-sensing device 50a, green sensor 50c, and the red photo-sensing device 50b integrated in the semiconductor substrate 110, wherein the blue photo-sensing device 50a, green sensor 50c, and the red photo-sensing device 50b may be photodiodes.

In the organic sensor 950 according to some example embodiments, the blue photo-sensing device 50a, green sensor 50c, and the red photo-sensing device 50b integrated in the semiconductor substrate 110 are stacked in a vertical direction.

The blue photo-sensing device 50a, green sensor 50c, and the red photo-sensing device 50b may be configured to selectively absorb and/or convert (into electrical signals, e.g., photoelectrically convert) light in each wavelength region depending on a stacking depth from the top surface 110S and thus sense it. In other words, the red photo-sensing device 50b configured to selectively absorb and/or convert (into electrical signals, e.g., photoelectrically convert) red light in a long wavelength region is disposed deeper from the top surface 110S of the semiconductor substrate 110 than the blue photo-sensing device 50a configured to selectively absorb and/or convert (into electrical signals, e.g., photoelectrically convert) blue light in a short wavelength region, and the green sensor 50c configured to selectively absorb and/or convert (into electrical signals, e.g., photoelectrically convert) green light in a medium wavelength region is disposed deeper from the top surface 110S of the semiconductor substrate 110 than the blue photo-sensing device 50a and closer to the top surface 110S of the semiconductor substrate 110 than the red photo-sensing device 50b. In this way, the color filter layer 70 may be omitted by separating absorption wavelengths depending on the stacking depth.

Figure 11:
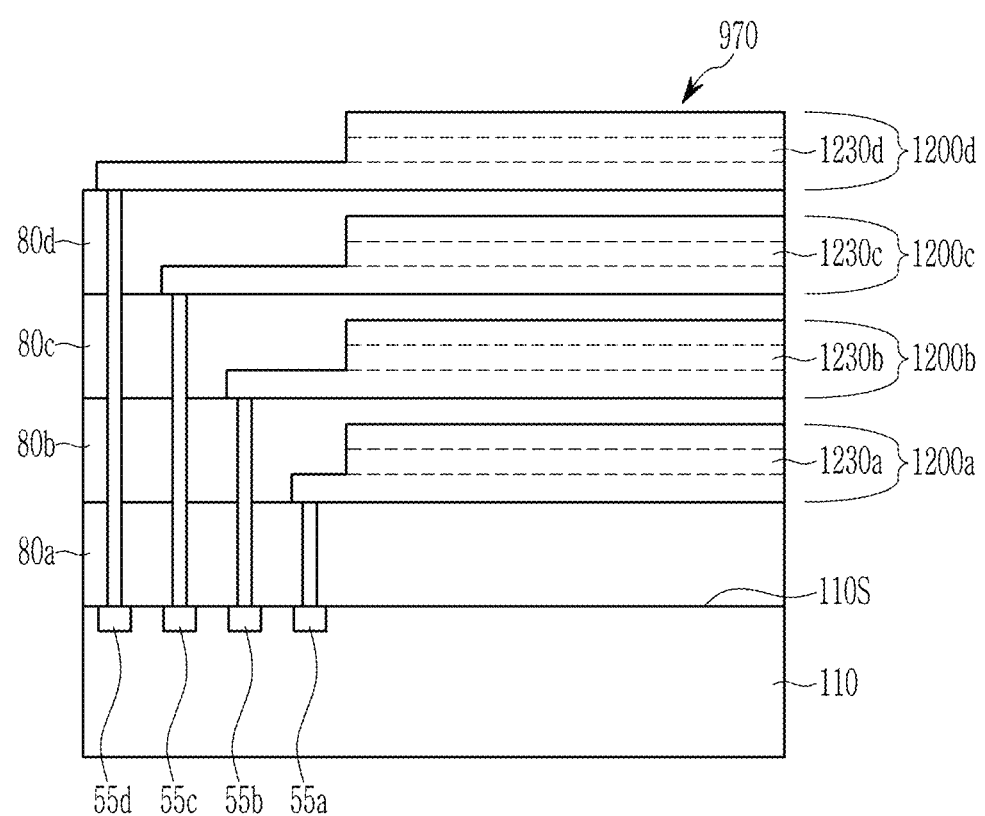
FIG. 11 is a cross-sectional view showing an organic sensor according to some example embodiments.

FIG. 11 is a cross-sectional view showing an organic sensor according to some example embodiments.

Referring to FIG. 11, the organic sensor 970 according to some example embodiments includes a first photoelectric device (e.g., infrared/near-infrared photoelectric device 1200d) configured to selectively absorb and/or convert (into electrical signals, e.g., photoelectrically convert) light in an infrared/near-infrared wavelength spectrum of incident light (e.g., a first near-infrared wavelength region), and at least one additional photoelectric device (e.g., 1200a-1200c) vertically stacked between the first photoelectric device and a semiconductor substrate (e.g., 110), each separate photoelectric device of the at least one additional photoelectric device including a separate photoelectric conversion layer and configured to selectively absorb and/or convert (into electrical signals, e.g., photoelectrically convert) light in a separate (e.g., respective) wavelength region of incident light that is different from the first near-infrared wavelength region and which may be a separate visible and/or non-visible wavelength region. For example, as shown in FIG. 11, the organic sensor 970 may include additional photoelectric devices that include a red photoelectric device configured to selectively absorb and/or convert (into electrical signals, e.g., photoelectrically convert) light in a red wavelength spectrum of incident light, a green photoelectric device configured to selectively absorb and/or convert (into electrical signals) light in a green wavelength spectrum of incident light, and a blue photoelectric device configured to selectively absorb and/or convert (into electrical signals) light in a blue wavelength spectrum of incident light, and they are stacked in the vertical direction (e.g., Z-direction).

Accordingly, it will be understood that, as shown in FIG. 11, the organic sensor 970 may include a plurality of photoelectric devices 1200a-1200d that are stacked vertically on the semiconductor substrate 110, such that the plurality of photoelectric devices 1200a to 1200d overlap each other in a direction extending perpendicular to a top surface 110S of the semiconductor substrate 110. While the organic sensor 970 includes multiple additional photoelectric devices 1200a-1200c in addition to the first photoelectric device (e.g., fourth photoelectric device 1200d) configured to selectively absorb and/or convert light in the first near-infrared wavelength region, it will be understood that in some example embodiments the organic sensor 970 may be limited to a single additional photoelectric device (e.g., any of 1200a to 1200c) between the photoelectric device 1200d and the semiconductor substrate 110.

The organic sensor 970 according to some example embodiments includes a semiconductor substrate 110, a lower insulation layer 80a, an intermediate insulation layer 80b, another intermediate insulation layer 80c, an upper insulation layer 80d, a first photoelectric device 1200a, a second photoelectric device 1200b, a third photoelectric device 1200c, and a fourth photoelectric device 1200d. In some example embodiments, the fourth photoelectric device 1200d may be referred to as a first photoelectric device configured to selectively absorb and/or convert (into electrical signals, e.g., photoelectrically convert) light in a first near-infrared wavelength region, and the first to third photoelectric devices 1200a to 1200c may be collectively referred to as at least one additional photoelectric device configured to selectively absorb and/or convert (into electrical signals, e.g., photoelectrically convert) light in one or more separate wavelength regions different from the first near-infrared wavelength region. As shown, the first to fourth photoelectric devices 1200a to 1200d are stacked vertically on the semiconductor substrate 110, such that the first to fourth photoelectric devices 1200a to 1200d overlap each other in a direction extending perpendicular to a top surface 110S of the semiconductor substrate 110.

The semiconductor substrate 110 may be a silicon substrate, and is integrated with the transmission transistor (not shown) and charge storages.

The first through third photoelectric devices 1200a-1200c may have a same structure as the additional photoelectric devices 850 shown in FIGS. 8 and 9, except each separate photoelectric device 1200a-1200c may be configured to photoelectrically convert a separate wavelength region of visible and/or non-visible (e.g., near-infrared) light, and the photoelectric conversion layers 1230a-1230c may have the same structure and/or composition as various example embodiments (e.g., different example embodiments) of the active layer 103 and/or active layer 30 as described herein so as to be configured to selectively absorb and/or convert (into electrical signals, e.g., photoelectrically convert) different visible and/or non-visible wavelength regions of light, and may include the near-infrared absorber. The fourth photoelectric device 1200d may have a same structure as photoelectric device 100 of FIG. 1 and/or photoelectric device 200 of FIG. 2, and the photoelectric conversion layer 1230d may have a same structure and/or composition as the active layer 30 as described herein, and may include the near-infrared absorber.

The first photoelectric device 1200a is formed on the lower insulation layer 80a. The first photoelectric device 1200a includes a photoelectric conversion layer 1230a. The first photoelectric device 1200a may be any one of the photoelectric devices described herein according to any of the example embodiments. The photoelectric conversion layer 1230a may selectively absorb and/or convert (into electrical signals, e.g., photoelectrically convert) light in one of infrared, red, blue, and green wavelength spectra of incident light. For example, the first photoelectric device 1200a may be a blue photoelectric device.

An intermediate insulation layer 80b is formed on the first photoelectric device 1200a.

The second photoelectric device 1200b is formed on the intermediate insulation layer 80b. The second photoelectric device 1200b includes a photoelectric conversion layer 1230b. The second photoelectric device 1200b may be any one of the photoelectric devices described herein according to any of the example embodiments. The photoelectric conversion layer 1230b may selectively absorb and/or convert (into electrical signals, e.g., photoelectrically convert) light in one of infrared, red, blue, or green wavelength spectra of incident light. For example, the second photoelectric device 1200b may be a green photoelectric device.

Another intermediate insulation layer 80c is formed on the second photoelectric device 1200b.

The third photoelectric device 1200c is formed on the intermediate insulation layer 80c. The third photoelectric device 1200c includes a photoelectric conversion layer 1230c. The third photoelectric device 1200c any one of the photoelectric devices described herein according to any of the example embodiments. The photoelectric conversion layer 1230c may selectively absorb and/or convert (into electrical signals, e.g., photoelectrically convert) light in one of infrared, red, blue, or green wavelength spectra of incident light. For example, the third photoelectric device 1200c may be a red photoelectric device.

The upper insulation layer 80d is formed on the third photoelectric device 1200c.

The lower insulation layer 80a, the intermediate insulation layers 80b and 80c, and the upper insulation layer 80d have a plurality of through holes exposing the charge storages 55a, 55b, 55c, and 55d.

The fourth photoelectric device 1200d is formed on the upper insulation layer 80d. The fourth photoelectric device 1200d includes a photoelectric conversion layer 1230d. The fourth photoelectric device 1200d may be any one of the photoelectric devices described herein according to any of the example embodiments. The photoelectric conversion layer 1230d may selectively absorb and/or convert (into electrical signals, e.g., photoelectrically convert) light in one of infrared, red, blue, or green wavelength spectra of light. For example, the fourth photoelectric device 1200d may be an infrared/near-infrared photoelectric device that may include the near-infrared absorber.

In the drawing, the first photoelectric device 1200a, the second photoelectric device 1200b, the third photoelectric device 1200c, and the fourth photoelectric device 1200d are sequentially stacked, but the present disclosure is not limited thereto, and they may be stacked in various orders.

As described above, the first photoelectric device 1200a, the second photoelectric device 1200b, the third photoelectric device 1200c, and the fourth photoelectric device 1200d have a stack structure, and thus the size of an organic sensor may be reduced to realize a down-sized organic sensor.

The organic sensor may be applied to various electronic devices, for example and the electronic devices may include for example a camera, a camcorder, a mobile phone internally having them, a display device, a security device, or a medical device, but are not limited thereto.

Figure 12:
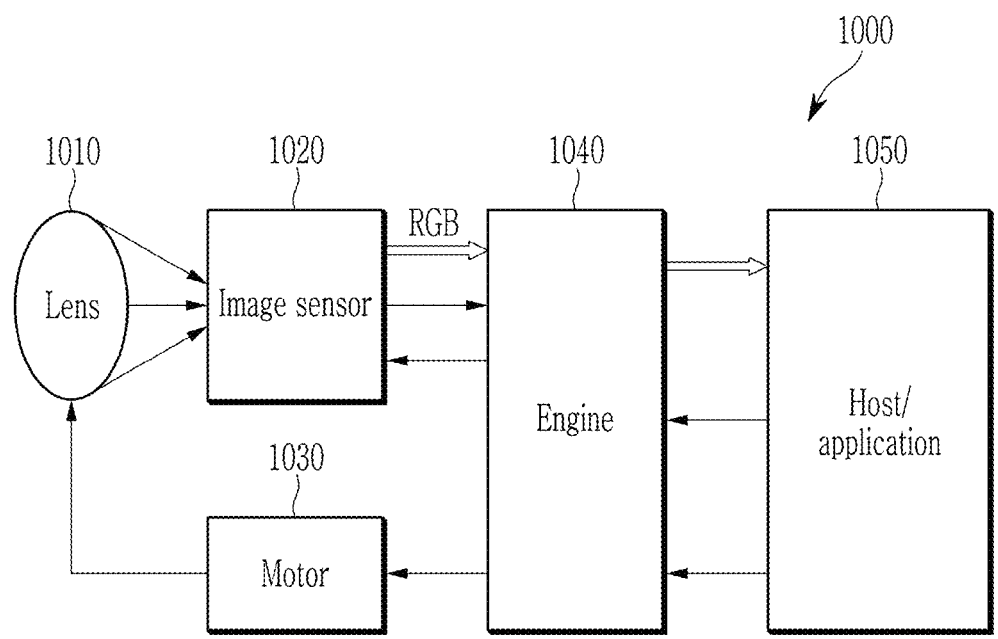
FIG. 12 is a block diagram of a digital camera including an organic sensor according to some example embodiments.

FIG. 12 is a block diagram of a digital camera including an image sensor according to some example embodiments.

Referring to FIG. 12, a digital camera 1000 includes a lens 1010, an image sensor 1020, a motor 1030, and an engine 1040. The image sensor 1020 may be one of image sensors according to some example embodiments, including the example embodiments shown in FIGS. 3 to 11.

The lens 1010 concentrates incident light on the image sensor 1020. The image sensor 1020 generates RGB data for received light through the lens 1010.

In example embodiments, the image sensor 1020 may interface with the engine 1040.

The motor 1030 may adjust the focus of the lens 1010 or perform shuttering in response to a control signal received from the engine 1040. The engine 1040 may control the image sensor 1020 and the motor 1030.

The engine 1040 may be connected to a host/application 1050.

Figure 13:
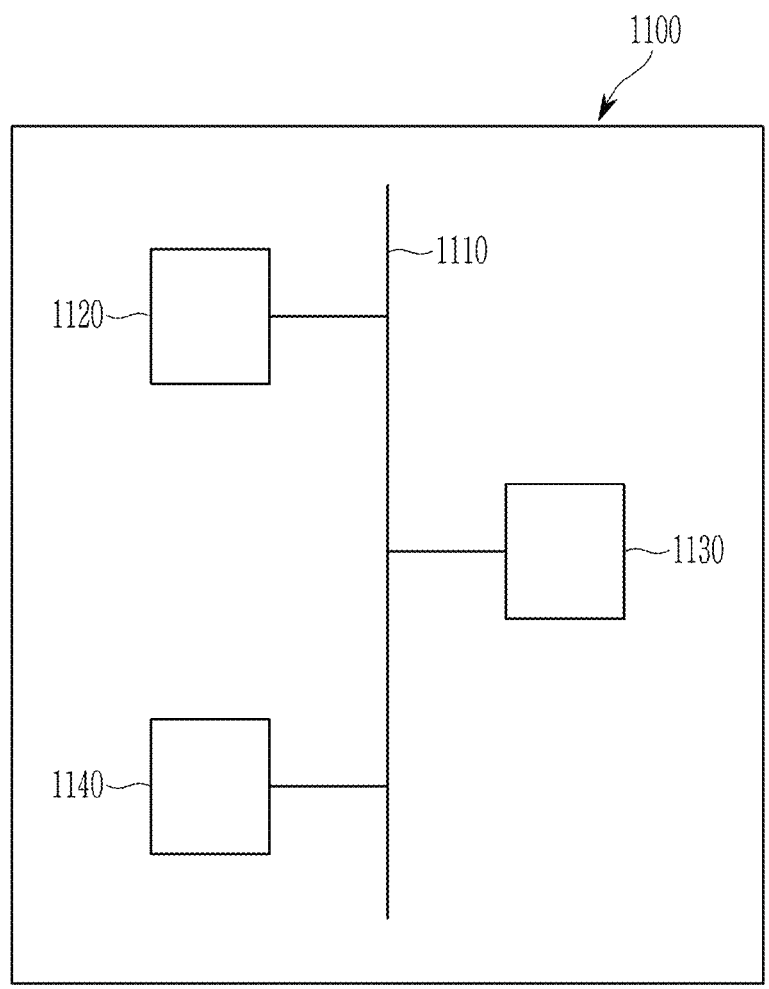
FIG. 13 is a schematic diagram showing an electronic device according to some embodiments.

FIG. 13 is a schematic diagram showing an electronic device 1100 according to some embodiments. Referring to FIG. 13, an electronic device 1100 may include a processor 1120, a memory 1130, and an image sensor 1140 that are electrically coupled together via a bus 1110. The image sensor 1140 may be an image sensor and/or organic sensor according to one of any of the example embodiments of image sensors and/or organic sensors. The memory 1130, which may be a non-transitory computer readable medium and may store a program of instructions. The memory 1130 may be a nonvolatile memory, such as a flash memory, a phase-change random access memory (PRAM), a magneto-resistive RAM (MRAM), a resistive RAM (ReRAM), or a ferro-electric RAM (FRAM), or a volatile memory, such as a static RAM (SRAM), a dynamic RAM (DRAM), or a synchronous DRAM (SDRAM). The processor 1120 may execute the stored program of instructions to perform one or more functions. For example, the processor 1120 may be configured to process electrical signals generated by the image sensor 1140. The processor 1120 may include processing circuitry such as hardware including logic circuits; a hardware/software combination such as a processor executing software; or a combination thereof. For example, the processing circuitry more specifically may include, but is not limited to, a central processing unit (CPU), an arithmetic logic unit (ALU), a digital signal processor, a microcomputer, a field programmable gate array (FPGA), a System-on-Chip (SoC), a programmable logic unit, a microprocessor, application-specific integrated circuit (ASIC), etc. The processor 1120 may be configured to generate an output (e.g., an image to be displayed on a display interface) based on such processing.

Hereinafter, some example embodiments are illustrated in more detail with reference to examples. However, the example embodiments are not limited to these examples.

SYNTHESIS EXAMPLES

Synthesis Example 1: Synthesis of Compound Represented by Chemical Formula 1-1

[Chemical Formula 1-1]

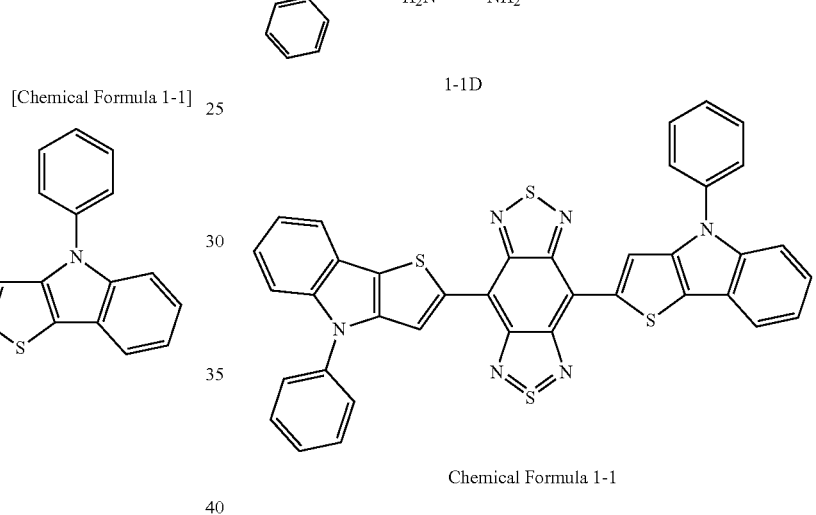

Chemical Formula 1-1

[Reaction Scheme 1-1]

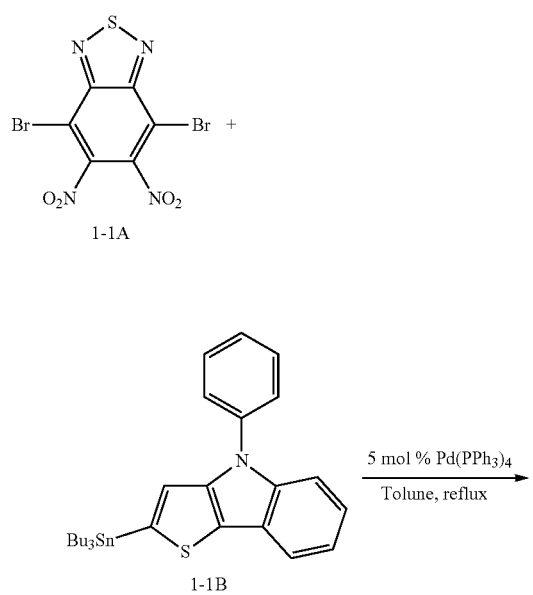

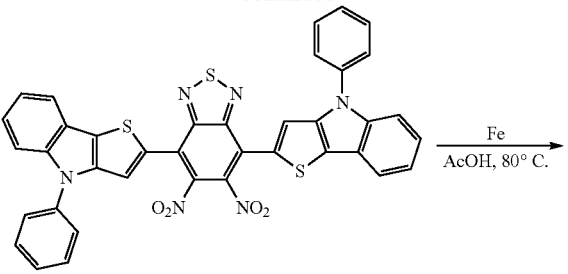

1-1C

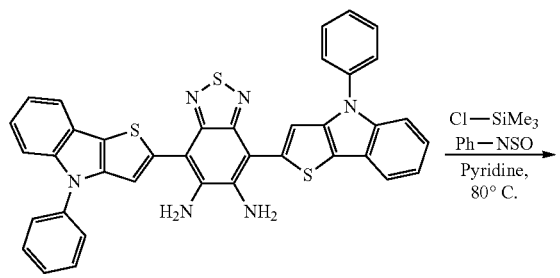

1-1D

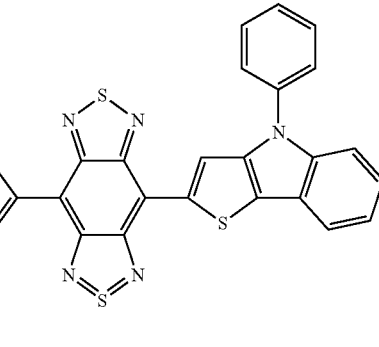

i) First Step: Synthesis of Compound 1-1C

In a round-bottomed flask under a nitrogen pressure, Compound 1-1A (4,7-dibromo-5,6-dinitrobenzo[c][1,2,5]thiadiazole, 0.71 g, 1.86 mmol) and Compound 1-1B (4-phenyl-2-(tributylstannyl)-4H-thieno[3,2-b]indole, 2 g, 3.71 mmol) are dissolved in toluene (18 ml), and tetrakis(triphenylphosphine)-palladium (0) (0.11 g, 0.093 mmol) is added thereto. Subsequently, the obtained mixture is heated at 110° C. and then, refluxed and stirred for 24 hours. When a reaction is complete, the reaction solution is concentrated by removing the toluene and then, separated through silica chromatography (Eluent: dichloromethane:n-hexane=1:4 in a volume ratio) and precipitated in 50 ml of methanol to obtain 0.95 g (Yield: 70%) of Compound 1-1C.

ii) Second Step: Synthesis of Compound 1-1D

In a round-bottomed flask under a nitrogen pressure, Compound 1-1C (0.56 g, 0.76 mmol) is dissolved in acetic acid (10 ml), and iron powder (0.33 g, 5.91 mmol) is added thereto. The obtained mixture is heated at 80° C. and stirred for 12 hours. The reactant is cooled down to room temperature, and distilled water is added thereto. Dichloromethane is used for extraction, and an organic layer therefrom is dried by using MgSO$_4$. After filtering the MgSO$_4$, a liquid therefrom is concentrated to obtain 0.28 g (Yield: 55%) of Compound 1-1D.

iii) Third Step: Synthesis of Compound represented by Chemical Formula 1-1

In a round-bottomed flask under a nitrogen pressure, Compound 1-1D (0.28 g, 0.42 mmol) is dissolved in pyridine (5 ml), and N-thionylaniline (0.19 ml, 1.69 mmol) and chlorotrimethyl silane (0.38 ml, 2.97 mmol) are added thereto and then, stirred at 80° C. for 12 hours. The reactant is cooled down to room temperature and then, precipitated in 50 ml of methanol and filtered, and a solid therefrom is sufficiently washed with dichloromethane and ethylacetate to obtain 0.15 g (Yield: 51%) of a compound represented by Chemical Formula 1-1.

MALDI-TOF molecular weight analysis: 688.376 m/z

Synthesis Example 2: Synthesis of Compound Represented by Chemical Formula 1-2

[Chemical Formula 1-2]

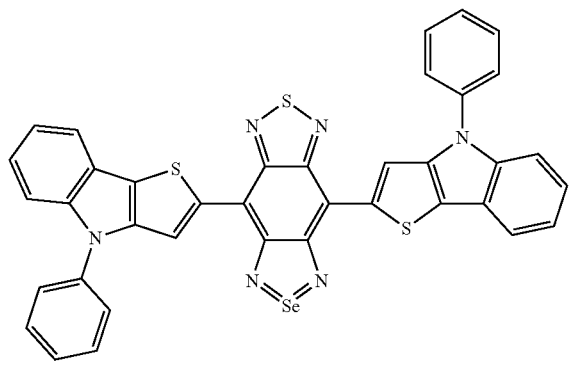

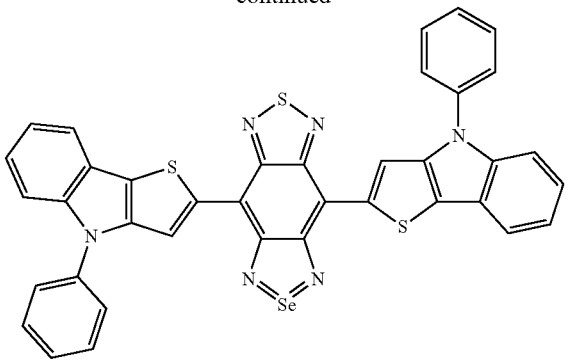

Chemical Formula 1-2

In a round-bottomed flask under a nitrogen pressure, Compound 1-1D (0.05 g, 0.076 mmol) of Synthesis Example 1 is dissolved in ethanol/chloroform, and selenium dioxide (0.011 g, 0.091 mmol) is added thereto and then, stirred at 80° C. for 12 hours. When a reaction is complete, the reactant is concentrated, and a solid therefrom is sufficiently washed with dichloromethane and ethylacetate to obtain 0.09 g (Yield: 40%) of a compound represented by Chemical Formula 1-2.

MALDI-TOF molecular weight analysis: 735.953 m/z

Synthesis Example 3: Synthesis of Compound Represented by Chemical Formula 1-3

[Chemical Formula 1-3]

[Reaction Scheme 1-2]

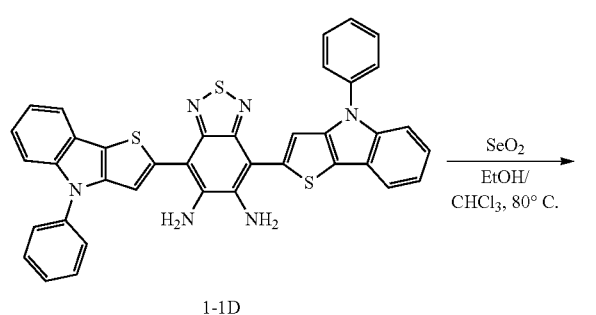

1-1D

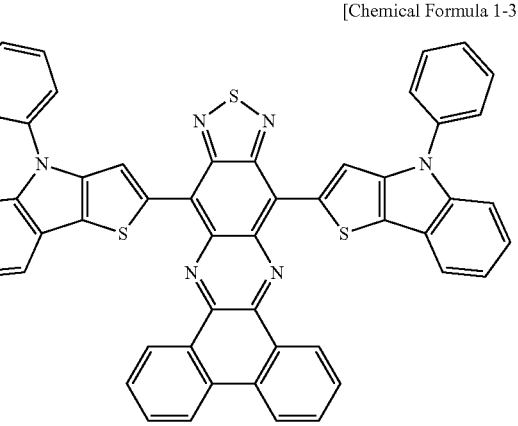

[Reaction Scheme 1-3]

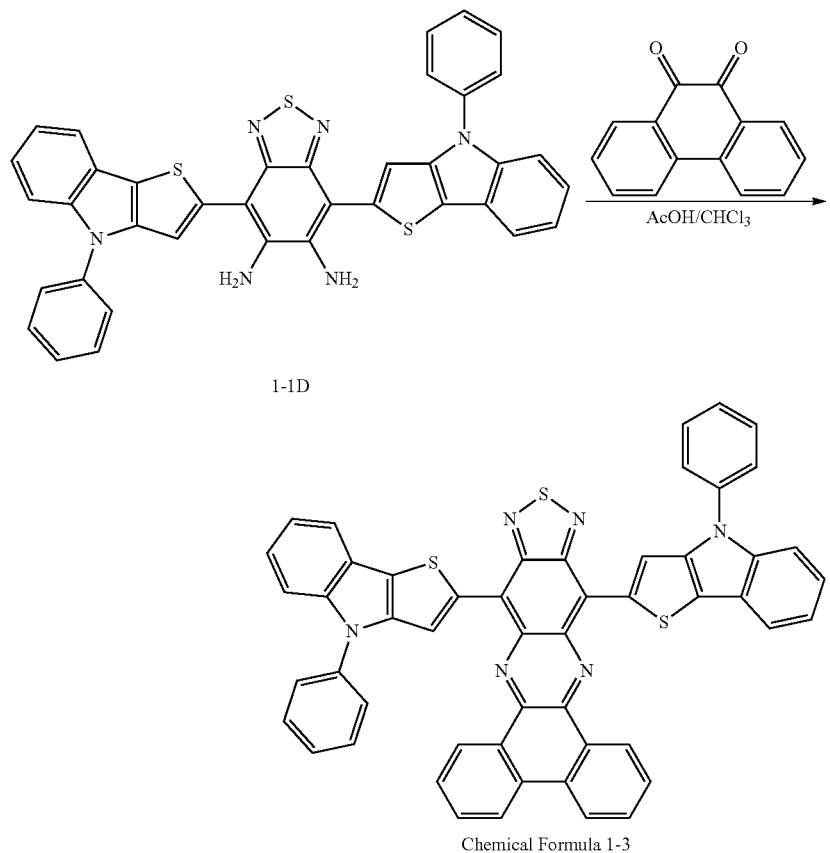

Chemical Formula 1-3

In a round-bottomed flask under a nitrogen pressure, Compound 1-1D (0.02 g, 0.03 mmol) of Synthesis Example 1 is dissolved in acetic acid/chloroform, and phenanthrene-9,10-dione (0.007 g, 0.033 mmol) are added thereto and then, stirred at 55° C. for 12 hours. Subsequently, distilled water is added to the reactant, and a solid therefrom is filtered and sufficiently washed with hexane and ethylacetate to obtain 0.016 g (Yield: 64%) of a compound represented by Chemical Formula 1-3.

MALDI-TOF molecular weight analysis: 832.487 m/z

Synthesis Example 4: Synthesis of Compound Represented by Chemical Formula 1-4

[Chemical Formula 1-4]

[Reaction Scheme 1-4]

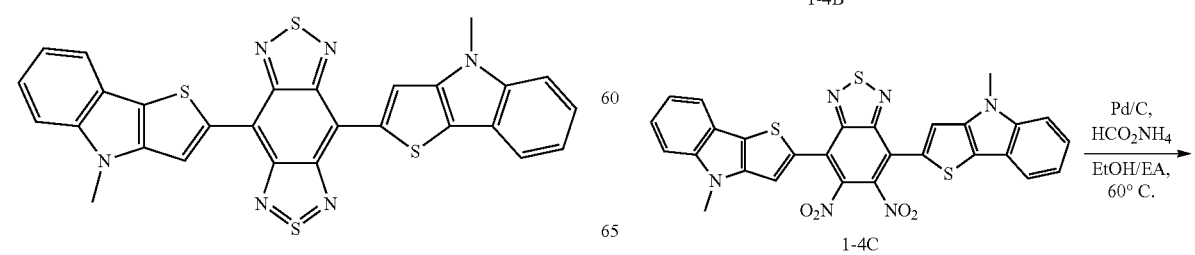

-continued

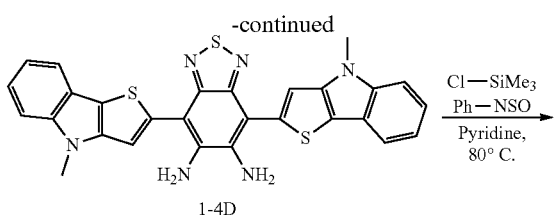

1-4D

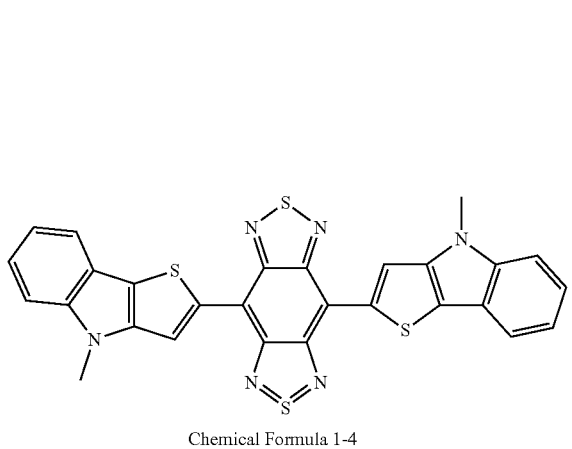

Chemical Formula 1-4 i) First Step: Synthesis of Compound 1-4C

In a round-bottomed flask under a nitrogen pressure, Compound 1-4A (4,7-dibromo-5,6-dinitrobenzo[c][1,2,5]thiadiazole, 0.8 g, 1.86 mmol) and Compound 1-4B (4-methyl-2-(tributylstannyl)-4H-thieno[3,2-b]indole, 12 g, 3.71 mmol) are dissolved in toluene (20 ml), and tetrakis(triphenylphosphine)-palladium (0) (0.12 g, 0.1 mmol) is added thereto. Subsequently, the mixture is heated at 110° C. and stirred for 24 hours. When a reaction is complete, after removing the toluene, the reaction solution is concentrated, separated through silica chromatography (Eluent: dichloromethane:n-hexane=1:4 in a volume ratio), and precipitated in 50 ml of methanol to obtain 0.9 g (Yield: 72%) of Compound 1-4C.

ii) Second Step: Synthesis of Compound 1-4D

In a round-bottomed flask under a nitrogen pressure, Compound 1-4C (0.34 g, 0.57 mmol) is dissolved in ethanol (9 ml) and ethylacetate (18 ml), and palladium on carbon (0.3 g, 0.28 mmol) and ammonium formate (3.59 g, 56.98 mmol) are added thereto. Subsequently, the mixture is heated at 60° C. and stirred for 12 hours. The reactant is cooled down to room temperature, separated through silica chromatography (Eluent: dichloromethane:n-hexane=2:1 in a volume ratio), and precipitated in 100 ml of hexane to obtain 0.16 g (Yield: 52%) of Compound 1-4D.

iii) Third Step: Synthesis of Compound represented by Chemical Formula 1-4

In a round-bottomed flask under a nitrogen pressure, Compound 1-4D (0.1 g, 0.42 mmol) is dissolved in pyridine (3 ml), and N-thionylaniline (0.08 ml, 0.74 mmol) and chlorotrimethyl silane (0.16 ml, 1.3 mmol) are added thereto and then, stirred at 80° C. for 12 hours. The reactant is cooled down to room temperature, precipitated in 30 ml of methanol, and filtered, and a solid obtained therefrom is sufficiently washed with dichloromethane and ethylacetate to obtain 0.06 g (Yield: 59%) of a compound represented by Chemical Formula 1-4.

Synthesis Example 5: Synthesis of Compound Represented by Chemical Formula 1-5

[Chemical Formula 1-5]

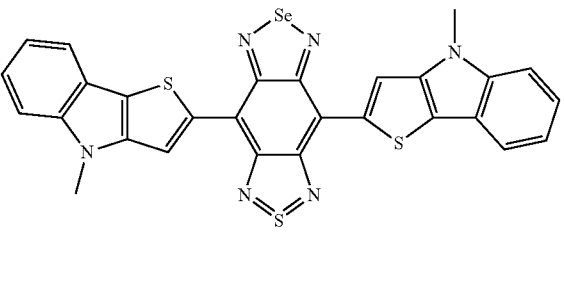

[Reaction Scheme 1-5]

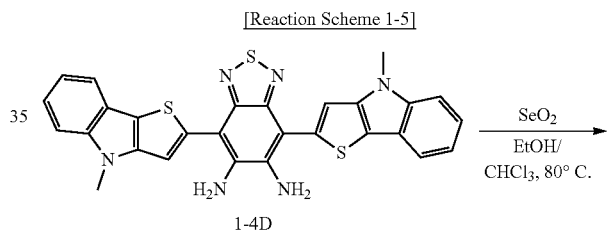

1-4D

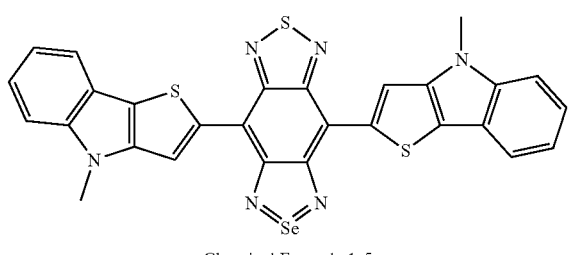

Chemical Formula 1-5

In a round-bottomed flask under a nitrogen pressure, Compound 1-4D (0.03 g, 0.055 mmol) is dissolved in ethanol/chloroform, and selenium dioxide (0.0074 g, 0.067 mmol) is added thereto and then, stirred at 80° C. for 12 hours. When a reaction is complete, the reactant is concentrated, and a solid obtained therefrom is sufficiently washed with dichloromethane and ethylacetate to obtain 0.02 g (Yield: 59%) of a compound represented by Chemical Formula 1-5.

Synthesis Example 6: Synthesis of Compound Represented by Chemical Formula 1-6

[Chemical Formula 1-6]

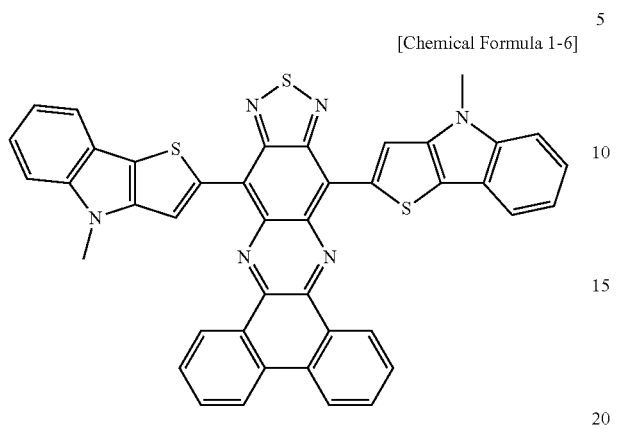

[Reaction Scheme 1-6]

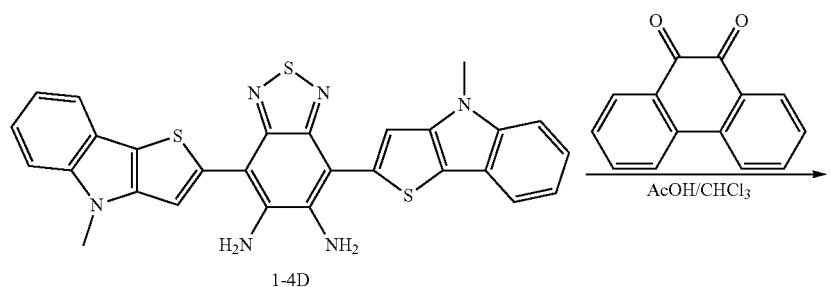

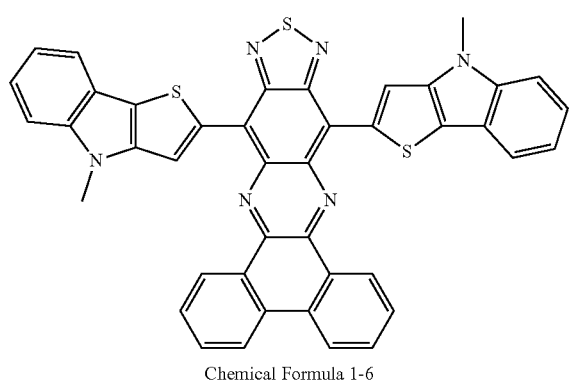

Chemical Formula 1-6

In a round-bottomed flask under a nitrogen pressure, Compound 1-4D (0.03 g, 0.055 mmol) of Synthesis Example 4 is dissolved in acetic acid/chloroform, and phenanthrene-9,10-dione (0.012 g, 0.061 mmol) is added thereto and then, stirred at 55° C. for 12 hours. A solid produced therein by adding distilled water to the reactant is filtered and sufficiently washed with hexane and ethylacetate to obtain 0.02 g (Yield: 59%) of a compound represented by Chemical Formula 1-6.

Synthesis Example 7: Synthesis of Compound Represented by Chemical Formula 1-7

[Chemical Formula 1-7]

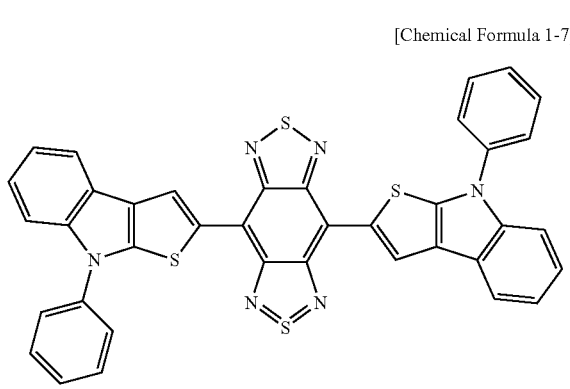 [SMILES: c1ccc(-n2c3ccccc3c3cc(-c4c5c(c(-c6cc7c8ccccc8n(-c8ccccc8)c7s6)c6nsnc46)N=S=N5)sc32)cc1]

[Reaction Scheme 1-7]

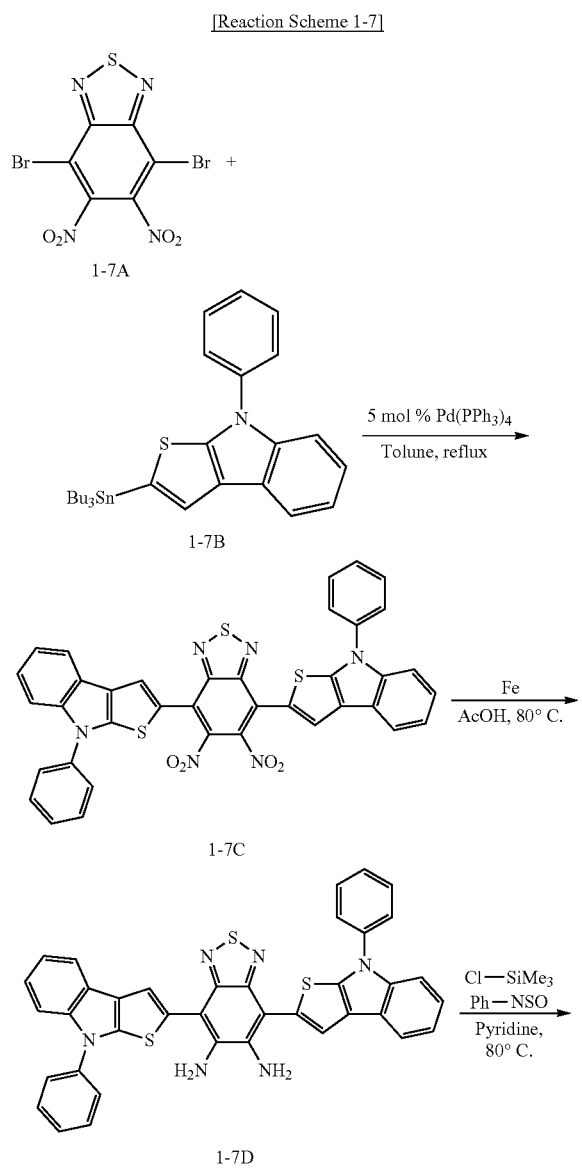

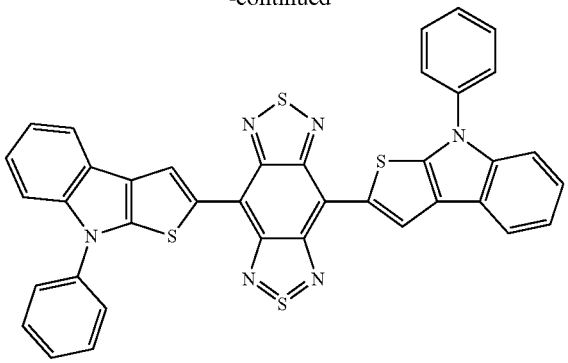

Chemical Formula 1-7 i) First Step: Synthesis of Compound 1-7C

In a round-bottomed flask under a nitrogen pressure, Compound 1-7A (4,7-dibromo-5,6-dinitrobenzo[c][1,2,5]thiadiazole, 0.71 g, 1.86 mmol) and Compound 1-7B (8-phenyl-2-(tributylstannyl)-8H-thieno[2,3-b]indole, 2 g, 3.71 mmol) are dissolved in toluene (18 ml), and tetrakis(triphenylphosphine)-palladium (0) (0.11 g, 0.093 mmol) is added thereto. Subsequently, the mixture is heated at 110° C. and then, refluxed and stirred for 24 hours. When a reaction is complete, after removing the toluene, the reaction solution is concentrated, separated through silica chromatography (Eluent: dichloromethane:n-hexane=1:4 in a volume ratio), and precipitated in 50 ml of methanol to obtain 0.1 g (Yield: 74%) of Compound 1-7C.

ii) Second Step: Synthesis of Compound 1-7D

In a round-bottomed flask under a nitrogen pressure, Compound 1-7C (0.6 g, 0.83 mmol) is dissolved in acetic acid (20 ml), and iron powder (1.39 g, 24.97 mmol) is added thereto. Subsequently, the mixture is heated at 80° C. and stirred for 12 hours. The reactant is cooed down to room temperature, and distilled water is added thereto. Dichloromethane is used for extraction, and an organic layer therefrom is dried by using $MgSO_4$. After filtering the $MgSO_4$, a liquid therefrom is concentrated to obtain 0.31 g (Yield: 56%) of Compound 1-7D.

iii) Third Step: Synthesis of Compound Represented by Chemical Formula 1-7

In a round-bottomed flask under a nitrogen pressure, Compound 1-7D (0.1 g, 0.15 mmol) is dissolved in pyridine (2 ml), and N-thionylaniline (0.07 ml, 0.6 mmol) and chlorotrimethyl silane (0.13 ml, 1.06 mmol) are added thereto and then, stirred at 80° C. for 12 hours. The reactant is cooled down to room temperature, precipitated in 30 ml of methanol, and paper-filtered, and a solid obtained therefrom is sufficiently washed with dichloromethane and ethylacetate to obtain 0.08 g (Yield: 77%) of a compound represented by Chemical Formula 1-7.

Synthesis Example 8: Synthesis of Compound Represented by Chemical Formula 1-8

[Chemical Formula 1-8]

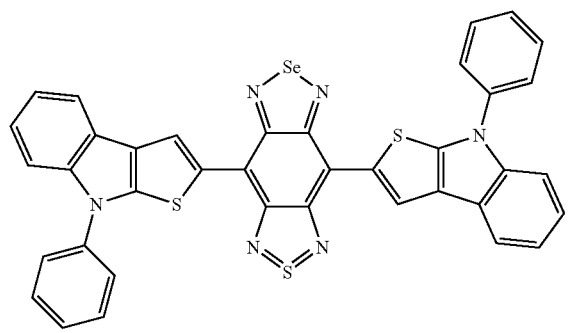

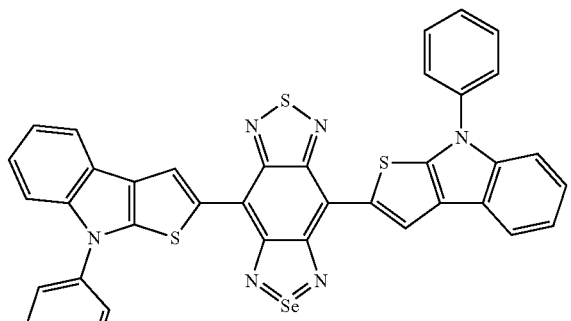

Chemical Formula 1-8

In a round-bottomed flask under a nitrogen pressure, Compound 1-7D (0.1 g, 0.15 mmol) of Synthesis Example 7 is dissolved in ethanol/chloroform, and selenium dioxide (0.02 g, 0.18 mmol) is added thereto and then, stirred at 80° C. for 12 hours. When a reaction is complete, the reactant is concentrated, and a solid obtained therefrom is sufficiently washed with dichloromethane and ethyl acetate to obtain 0.07 g (Yield: 63%) of a compound represented by Chemical Formula 1-8.

Synthesis Example 9: Synthesis of Compound Represented by Chemical Formula 1-9

[Reaction Scheme 1-8]

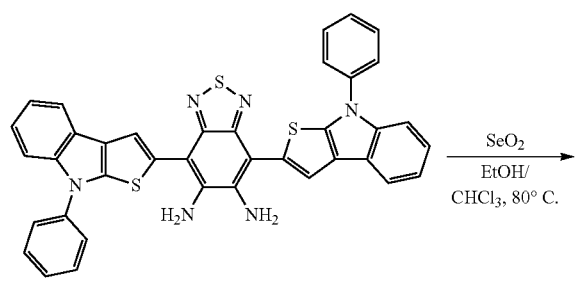

[Chemical Formula 1-9]

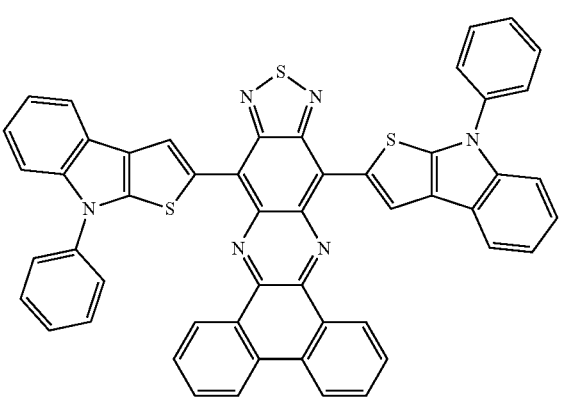

[Reaction Scheme 1-9]

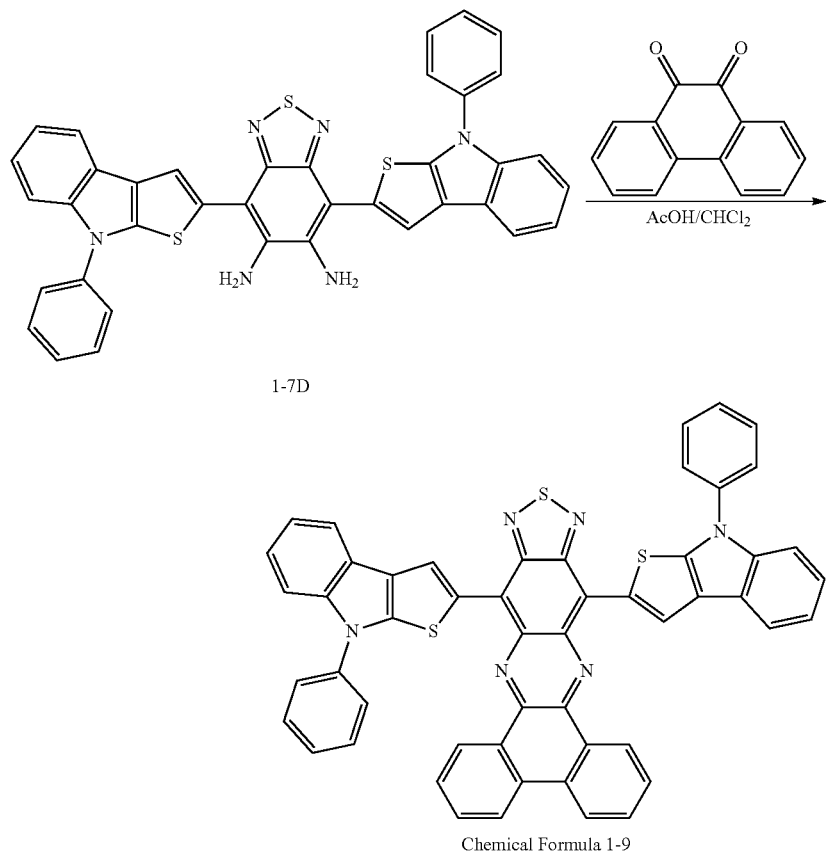

Chemical Formula 1-9

In a round-bottomed flask under a nitrogen pressure, Compound 1-7D (0.1 g, 0.15 mmol) of Synthesis Example 7 is dissolved in acetic acid/chloroform, and phenanthrene-9,10-dione (0.038 g, 0.18 mmol) is added thereto and then stirred at 55° C. for 12 hours. A solid produced therein by adding distilled water to the reactant is filtered and then, sufficiently washed with hexane and ethyl acetate to obtain a 0.09 g (Yield: 72%) of a product.

MALDI-TOF molecular weight analysis: 832.487 m/z

Comparative Synthesis Example 1: Synthesis of Compound Represented by Chemical Formula 2-1

[Chemical Formula 2-1]

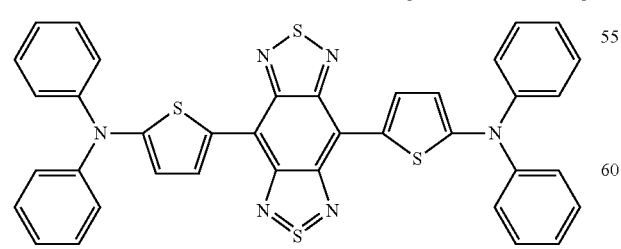

N,N-diphenyl-5-(tributylstannyl)thiophen-2-amine (0.18 g, 0.34 mmol), 4,8-dibromobenzo[1,2-c;4,5-c]bis([1,2,5] thiadiazole) (0.1 g, 0.28 mmol), and tetrakis(triphenylphosphine)palladium (0) (0.008 g, 0.014 mmol) are dissolved in 5 ml of dry toluene and then, stirred at 110° C. for 18 hours. When a reaction is complete, the toluene is evaporated and concentrated, and dichloromethane is used for precipitation to obtain 0.1 g (Yield: 52%) of a product.

MALDI-TOF molecular weight analysis: 692 m/z

Comparative Synthesis Example 2: Synthesis of Compound Represented by Chemical Formula 2-2

[Chemical Formula 2-2]

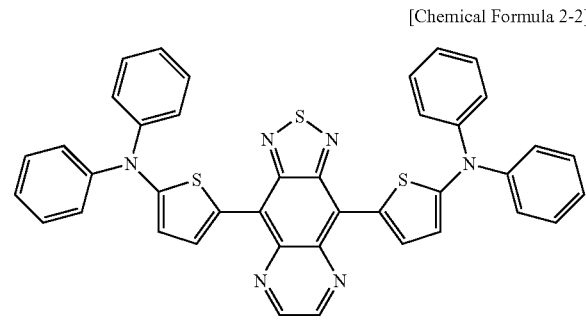 [SMILES: c1ccc(N(c2ccccc2)c2ccc(-c3c4nccnc4c(-c4ccc(N(c5ccccc5)c5ccccc5)s4)c4nsnc34)s2)cc1]

[Reaction Scheme 2-2]

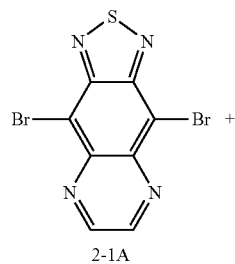

2-1A

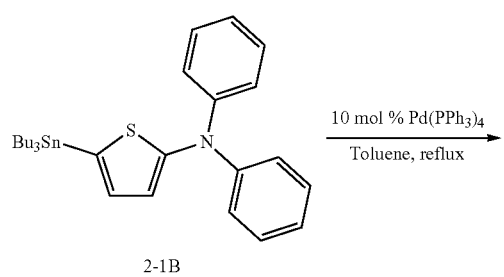

2-1B

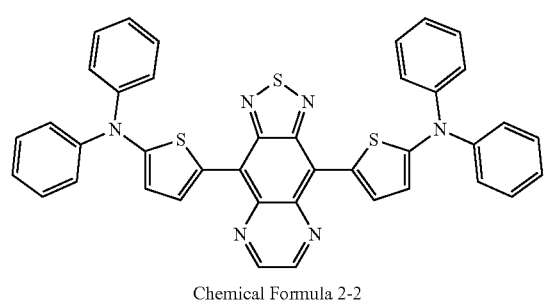

Chemical Formula 2-2

In a round-bottomed flask under a nitrogen pressure, 4,9-dibromo-[1,2,5]thiadiazolo[3,4-g]quinoxaline (Compound 2-1A, 1.13 g, 3.26 mmol) and N,N-diphenyl-5-(tributylstannyl)thiophen-2-amine (Compound 2-1B, 4.4 g, 8.14 mmol) are dissolved in toluene (15 ml), and tetrakis (triphenylphosphine)-palladium (0) (0.376 g, 0.326 mmol) is added thereto. Subsequently, the mixture is heated at 110° C. and refluxed and stirred for 24 hours. The reactant is cooled down to room temperature (24° C.) and concentrated, and ethylacetate is added thereto. Subsequently, a solid produced therein is filtered and then, washed with n-hexane/ethylacetate/methanol. The solid is vacuum-dried to obtain a green solid of a compound (1.5 g) represented by Chemical Formula 2-2.

$^1$H NMR (500 MHz, CDCl$_3$): d 8.92 (d, 2H), d 8.75 (s, 2H), d 7.35 (t, 8H), d 7.30 (d, 8H), d 7.14 (t, 4H), d 6.75 (d, 2H).

UPLC-MS: [M+H]$^+$ 687.06

Comparative Synthesis Example 3: Synthesis of Compound Represented by Chemical Formula 2-3

In a method described in an article (D. Ma, Z. Y. Wang et al. J. Phys. Chem. C, 2009, 113, 1589 to 1595), a compound represented by Chemical Formula 2-3 is synthesized.

[Chemical Formula 2-3]

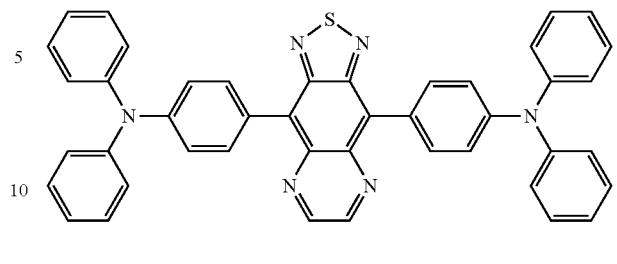

Comparative Synthesis Example 4: Synthesis of Compound Represented by Chemical Formula 2-4

[Chemical Formula 2-4]

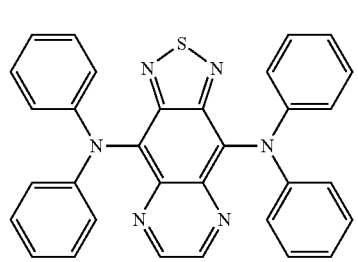

[Reaction Scheme 2-4]

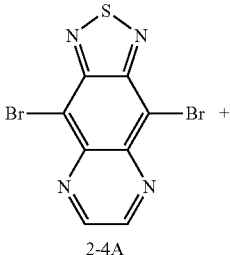

2-4A

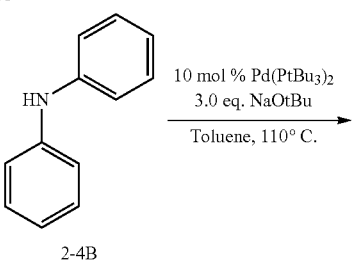

2-4B

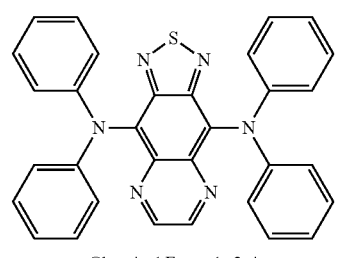

Chemical Formula 2-4

In a round-bottomed flask under a nitrogen pressure, Compound 2-4A (4,9-dibromo-[1,2,5]thiadiazolo[3,4-g]quinoxaline, 530 mg, 1.53 mmol), Compound 2-4B (diphenylamine, 646 mg, 3.82 mmol), and sodium tert-butoxide (317 mg, 4.59 mmol) are dissolved in toluene (10 ml), and bis(tri-tert-butylphosphine)palladium (0) (78 mg, 0.153 mmol) is added thereto. Subsequently, the mixture is heated at 110° C. and then, refluxed and stirred for 24 hours. The reactant is cooled down to room temperature (24° C.) and concentrated, and then, ethylacetate, distilled water, and an ammonium chloride aqueous solution in order are added thereto. The ethylacetate is used for extraction, and an organic layer therefrom is dried by using $MgSO_4$. After filtering the $MgSO_4$, the solution is concentrated, purified through silica chromatography (Eluent: ethyl acetate: hexane=1:4 in a volume ratio), and vacuum-dried to obtain 120 mg (Yield: 15%) of a green solid of a compound represented by Chemical Formula 2-4.

$^1$H NMR (300 MHz, $CD_2Cl_2$): d 8.57 (s, 2H), d 7.19 (d, 8H), d 7.06 (d, 8H), d 6.98 (t, 4H).

UPLC-MS: $[M+H]^+$ 523.14

Comparative Synthesis Example 5: Synthesis of Compound Represented by Chemical Formula 2-5

A method described in Scheme 1 (ACS Nano, Highly Stable Organic Small Molecular Nanoparticles as an Advanced and Biocompatible Phototheranostic Agent of Tumor in Living Mice, 2017, 7177-7188) is used to synthesize a compound represented by Chemical Formula 2-5.

TABLE 1

|  | $\lambda_{max}$ (nm) (solution) | $\lambda_{max}$ (nm) (thin film) |
| --- | --- | --- |
| Synthesis Example 1 | 908 | 963 |
| Comparative Synthesis Example 3 | 594 | 623 |
| Comparative Synthesis Example 4 | 692 | 690 |

TABLE 2

|  | $\lambda_{max}$ (nm) (solution) |
| --- | --- |
| Synthesis Example 2 | 1001 |
| Synthesis Example 3 | 853 |
| Synthesis Example 4 | 923 |
| Synthesis Example 5 | 1020 |
| Synthesis Example 6 | 889 |
| Synthesis Example 7 | 943 |
| Synthesis Example 8 | 1051 |
| Synthesis Example 9 | 852 |
| Comparative Synthesis Example 5 | 780 |

Referring to Tables 1 and 2, the compounds according to Synthesis Examples 1 to 9 exhibit a sufficient wavelength absorption in a near-infrared wavelength region compared with the compounds according to Comparative Synthesis Examples 1 to 5.

[Chemical Formula 2-5]

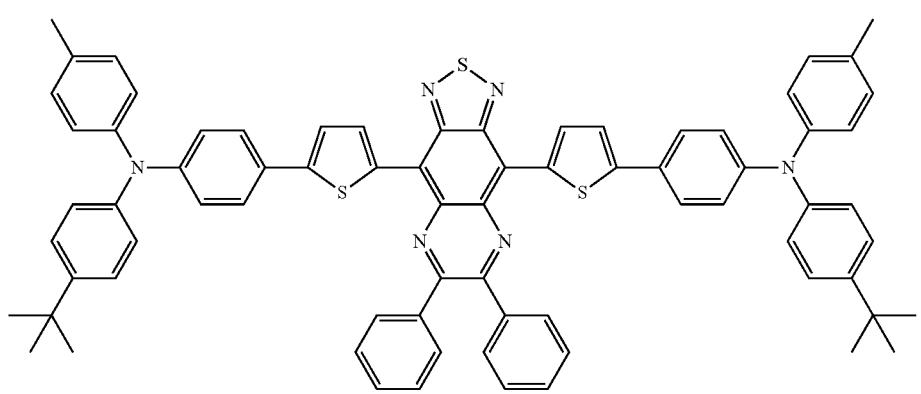

Evaluation I: Light Absorption Characteristics

The compounds of Synthesis Example 1 and Comparative Synthesis Examples 3 and 4 are respectively dissolved in dichloromethane at a concentration of $1\times10^{-5}$ M to evaluate light absorption characteristics thereof in a solution state.

In addition, the compound of Synthesis Example 1 is deposited on a glass substrate to form a 30 nm-thick thin film and thus evaluate light absorption characteristics thereof in a thin film state. On the other hand, the compounds of Comparative Synthesis Examples 1 and 2 are not depositable and thus cannot be evaluated. The light absorption characteristics are evaluated by measuring a maximum absorption wavelength (λmax) with a UV-Vis-NIR spectrometer (Shimadzu UV-3600 Plus). The results are shown in Table 1.

On the other hand, with respect to the compounds according to Synthesis Examples 2 to 9 and Comparative Synthesis Example 5, DFT, TD-DFT (wB97X-D function with 6-311G (d,p) basis set) are calculated by using a Gaussian09 (G09) program assuming that the samples are toluene solutions. The results are shown in Table 2.

The compounds of Synthesis Examples 1 to 7 are used to calculate oscillator strength in a DFT B3LYP/6-311G(d,p) level by using the Gaussian 09 program, and the results are shown in Table 3.

TABLE 3

|  | Oscillator Strength (a.u.) |
| --- | --- |
| Synthesis Example 1 | 0.81 |
| Synthesis Example 2 | 0.67 |
| Synthesis Example 3 | 0.72 |
| Synthesis Example 4 | 0.80 |
| Synthesis Example 5 | 0.66 |
| Synthesis Example 6 | 0.72 |
| Synthesis Example 7 | 0.69 |

Referring to Table 3, the compounds according to Synthesis Examples 1 to 7 exhibit high oscillator strength and thus a high absorption coefficient.

Evaluation II: Deposition Characteristics

Deposition characteristics of the compounds of Synthesis Examples 1 to 9 and Comparative Synthesis Examples 1 to 5 are evaluated. The deposition characteristics are evaluated through a thermal gravimetric analysis (TGA) by sublimating the compounds under high vacuum of less than or equal to 10 Pa to evaluate thermal stability from a weight loss according to a temperature increase.

The results of Synthesis Examples 1 to 3 and Comparative Synthesis Examples 1 and 2 are shown in Table 4.

TABLE 4

|  | $T_s$(° C.) (−10 wt %) |
|---|---|
| Synthesis Example 1 | 365 |
| Synthesis Example 2 | 375 |
| Synthesis Example 3 | 370 |
| Comparative Synthesis Example 1 | Not depositable |
| Comparative Synthesis Example 2 | Not depositable |

* $T_s$(° C.) (−10 wt %): a temperature that a weight of a sample is 10 wt % decreased Referring to Table 4, the compounds of Synthesis Examples 1 to 3 are depositable. On the other hand, the compounds of Comparative Synthesis Examples 1 and 2 are not depositable and thus cannot be evaluated.

Example and Comparative Example: Production of Photoelectric Device

A 150 nm-thick anode is formed by sputtering ITO on a glass substrate. Subsequently, each compound according to Synthesis Examples 1 to 9 and Comparative Synthesis Examples 3 to 5 is co-deposited with C60 in a 1:1 volume ratio, respectively, to form a 150 nm-thick active layer (photoelectric conversion layer). Then, C60 is deposited on the active layer to form a 30 nm-thick auxiliary layer. Then, ITO is sputtered on the auxiliary layer to form a 7 nm-thick cathode. Aluminum oxide ($Al_2O_3$) is deposited on the cathode to form a 50 nm-thick anti-reflection layer and encapsulated with a glass plate to produce the photoelectric devices according to Examples 1 to 9 and Comparative Examples 3 to 5.

Evaluation III: Photoelectric Conversion Efficiency

Figure 14:
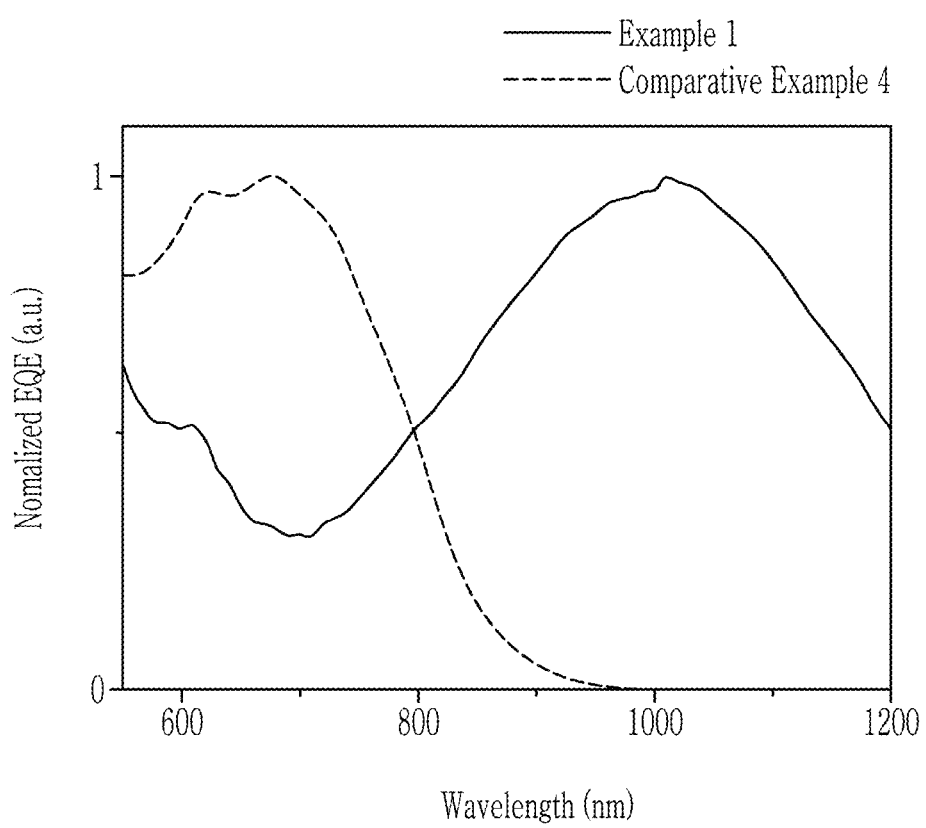
FIG. 14 is a graph showing photoelectric conversion efficiency of the photoelectric devices of Example 1 and Comparative Example 4.

Photoelectric conversion efficiency of the photoelectric devices according to Examples 1 to 9 and Comparative Examples 3 to 5 is evaluated. The photoelectric conversion efficiency is measured by using an IPCE measurement system (TNE Technology Co., Ltd., Korea). First, the system is calibrated by using a Si photodiode (Hamamatsu Photonics K.K., Japan) and then, mounted on a photoelectric device to measure the photoelectric conversion efficiency in a wavelength range of about 400 nm to about 1600 nm. The results of Example 1 and Comparative Example 4 are shown in FIG. 14. FIG. 14 is a graph showing photoelectric conversion efficiency of the photoelectric devices of Example 1 and Comparative Example 4.

Referring to FIG. 14, the photoelectric device of Example 1 exhibits excellent photoelectric conversion efficiency in a long wavelength region of about 870 nm, compared with the photoelectric device of Comparative Example 4.

While this disclosure has been described in connection with what is presently considered to be practical example embodiments, it is to be understood that the inventive concepts are not limited to the disclosed example embodiments. On the contrary, the inventive concepts are intended to cover various modifications and equivalent arrangements included within the spirit and scope of the appended claims.

What is claimed is:

1. A near-infrared absorber, comprising:
a compound represented by Chemical Formula 1:

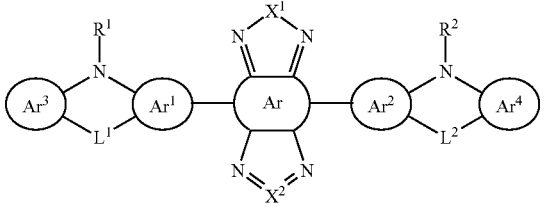

[Chemical Formula 1]

wherein, in Chemical Formula 1,
Ar is a substituted or unsubstituted C6 to C30 aromatic ring, a substituted or unsubstituted C3 to C30 heteroaromatic ring, or a combination thereof,
$X^1$ is O, S, Se, Te, S(=O), S(=$O_2$), $NR^a$, $CR^bR^c$, $SiR^dR^e$, $GeR^fR^g$, $CR^h$=$CR^i$, or $CR^{hh}$=$CR^{ii}$, wherein $R^a$, $R^b$, $R^c$, $R^d$, $R^e$, $R^f$, $R^g$, $R^h$, and $R^i$ are independently hydrogen, deuterium, a C1 to C30 alkyl group, a C1 to C30 haloalkyl group, a C6 to C30 aryl group, a C6 to C30 aryloxy group, a C3 to C30 heteroaryl group, a halogen, a cyano group, or a combination thereof, $R^{hh}$ and $R^{ii}$ are independently $(CH)_w$ where w is a positive integer or at least one heteroatom of O, N, S, Se, or Te, and $R^{hh}$ and $R^{ii}$ are linked to each other to form an aromatic ring or a heteroaromatic ring,
$X^2$ is O, S, Se, Te, C, $CR^x$=$CR^y$, $CR^{xx}$=$CR^{yy}$, S(=O) or S(=$O_2$), wherein $R^x$ and $R^y$ are independently hydrogen, deuterium, a C1 to C30 alkyl group, a C1 to C30 haloalkyl group, a C6 to C30 aryl group, a C6 to C30 aryloxy group, a C3 to C30 heteroaryl group, a halogen, a cyano group, or a combination thereof, $R^{xx}$ and $R^{yy}$ are independently $(CH)_v$ where v is a positive integer or at least one heteroatom of O, N, S, Se, or Te, and $R^{xx}$ and $R^{yy}$ are linked to each other to form an aromatic ring or a heteroaromatic ring,
$Ar^1$ and $Ar^2$ are independently a heteroarene group including at least one heteroatom of O, S, Se, or Te,
$Ar^3$ and $Ar^4$ are independently a substituted or unsubstituted C6 to C30 arene group, a substituted or unsubstituted C3 to C30 heteroarene group, or a condensed ring group thereof,
$R^1$ and $R^2$ are independently hydrogen, deuterium, a halogen, a cyano group, a nitro group, a hydroxyl group, a substituted or unsubstituted C1 to C10 alkyl group, a substituted or unsubstituted C1 to C10 alkoxy group, a substituted or unsubstituted C6 to C10 aryl group, or a substituted or unsubstituted C3 to C10 heteroaryl group, and
$L^1$ and $L^2$ are independently a single bond, —O—, —S—, —Se—, —Te—, —N=, —$NR^a$—, —$SiR^bR^c$—, —$GeR^dR^e$—, —$(CR^fR^g)_n$—, or —$(C(R^h)$=$C(R^i))$—, wherein $R^a$, $R^b$, $R^c$, $R^d$, $R^e$, $R^f$, $R^g$, $R^h$, and $R^i$ are independently hydrogen, deuterium, a halogen, a cyano group, a substituted or unsubstituted C1 to C10 alkyl group, or a substituted or unsubstituted C6 to C10 aryl group, wherein $R^b$ and $R^c$, $R^d$ and $R^e$, $R^f$ and $R^g$, or $R^h$ and $R^i$ are independently present or are linked to each other to form a separate ring, and n of —$(CR^fR^g)_n$— is an integer of 1 or 2.

2. The near-infrared absorber of claim 1, wherein in Chemical Formula 1, Ar is benzene ring, a substituted or unsubstituted naphthalene ring, a substituted or unsubstituted anthracene ring, a substituted or unsubstituted phenanthrene ring, a substituted or unsubstituted tetracene ring, or a substituted or unsubstituted pyrene ring.

3. The near-infrared absorber of claim 1, wherein in Chemical Formula 1, Ar is a substituted or unsubstituted quinoline ring, a substituted or unsubstituted isoquinoline ring, a substituted or unsubstituted quinoxaline ring, a substituted or unsubstituted quinazoline ring, or a substituted or unsubstituted phenanthroline ring.

4. The near-infrared absorber of claim 1, wherein in Chemical Formula 1, Ar is one moiety of a set of moieties represented by Chemical Formula A-1, each moiety including at least one aromatic ring and left and right linking groups:

[Chemical Formula A-1]

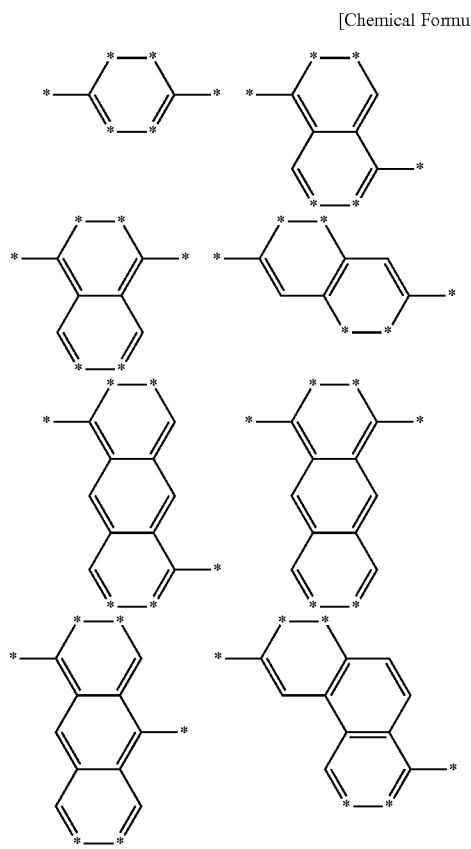

wherein, in Chemical Formula A-1,
hydrogen of each aromatic ring is optionally replaced by a halogen, a cyano group, a C1 to C10 alkyl group, a C1 to C10 alkoxy group, a C1 to C10 haloalkyl group, —SiH$_3$, or a C1 to C10 alkylsilyl group,
separate adjacent pairs of *'s inside the at least one aromatic ring are linking portions with separate, respective ones of an N—X$^1$—N-containing ring of Chemical Formula 1 or —N=X$^2$=N— containing ring of Chemical Formula 1, and
*'s of the left and right linking groups are portions linked to separate, respective ones of Ar$^1$ or Ar$^2$ of Chemical Formula 1.

5. The near-infrared absorber of claim 1, wherein in Chemical Formula 1, Ar is one moiety of a set of moieties represented by Chemical Formula A-2, each moiety including at least one aromatic ring and left and right linking groups:

[Chemical Formula A-2]

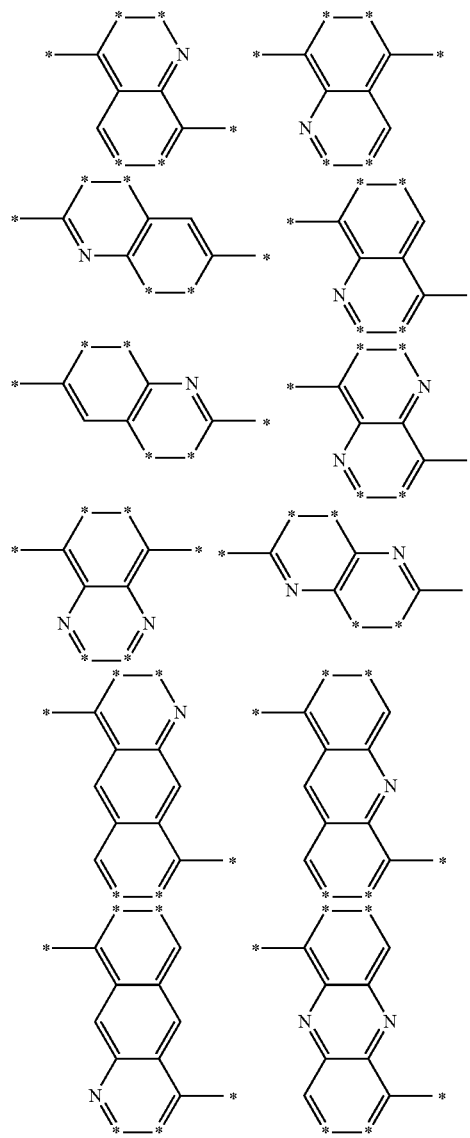

wherein, in Chemical Formula A-2,
hydrogen of each aromatic ring is optionally replaced by a halogen, a cyano group, a C1 to C10 alkyl group, a C1 to C10 alkoxy group, a C1 to C10 haloalkyl group, —SiH$_3$, or a C1 to C10 alkylsilyl group,
separate adjacent pairs of *'s inside the at least one aromatic ring are linking portions with separate, respective ones of an N—X$^1$—N-containing ring of Chemical Formula 1 and —N=X$^2$=N-containing ring of Chemical Formula 1, and
*'s of the left and right linking groups are portions linked to separate, respective ones of Ar$^1$ and Ar$^2$ of Chemical Formula 1.

6. The near-infrared absorber of claim 1, wherein in Chemical Formula 1, when X$^2$ is CR$^{xx}$—CR$^{yy}$, the aromatic ring formed by linking R$^{xx}$ with R$^{yy}$ is a substituted or unsubstituted benzene ring, a substituted or unsubstituted naphthalene ring, a substituted or unsubstituted acenaphthene ring, a substituted or unsubstituted anthracene ring, a substituted or unsubstituted phenanthrene ring, a substituted or unsubstituted tetracene ring, or a substituted or unsubstituted pyrene ring.

7. The near-infrared absorber of claim 1, wherein in Chemical Formula 1, when $X^2$ is $CR^{xx}$—$CR^{yy}$, the aromatic ring formed by linking $R^{xx}$ with $R^{yy}$ is a substituted or unsubstituted quinoline ring, a substituted or unsubstituted isoquinoline ring, a substituted or unsubstituted quinoxaline ring, a substituted or unsubstituted quinazoline ring, a substituted or unsubstituted phenanthroline ring, a substituted or unsubstituted pyrimidine ring, or a substituted or unsubstituted benzodithiophene ring.

8. The near-infrared absorber of claim 1, wherein in Chemical Formula 1, when $X^2$ is $CR^{xx}$—$CR^{yy}$, the aromatic ring formed by linking $R^{xx}$ with $R^{yy}$ is one moiety of a set of moieties represented by Chemical Formula B-1, each moiety including at least one aromatic ring:

[Chemical Formula B-1]

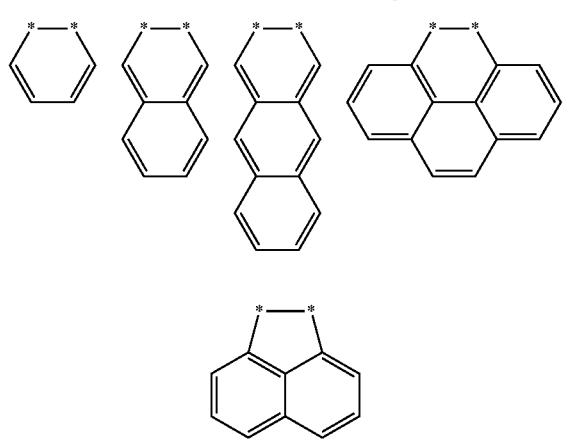

wherein, in Chemical Formula B-1, hydrogen of each aromatic ring is optionally replaced by a halogen, a cyano group, a C1 to C30 alkyl group, a C1 to C30 alkoxy group, a C1 to C30 haloalkyl group, —$SiH_3$, a C1 to C30 alkylsilyl group, a C6 to C30 aryl group, a C6 to C30 aryloxy group, or a C3 to C30 heteroaryl group, and

*'s inside the at least one aromatic ring are linking portions with a carbon of $CR^{xx}$—$CR^{yy}$.

9. The near-infrared absorber of claim 1, wherein in Chemical Formula 1, when $X^2$ is $CR^{xx}$—$CR^{yy}$, the aromatic ring formed by linking $R^{xx}$ with $R^{yy}$ is one moiety of a set of moieties represented by Chemical Formula B-2, each moiety including at least one aromatic ring:

[Chemical Formula B-2]

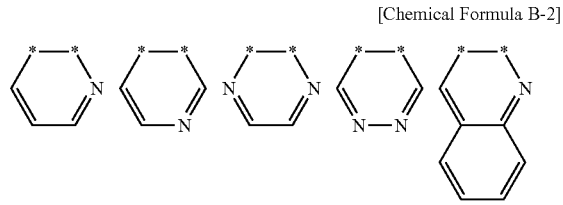

-continued

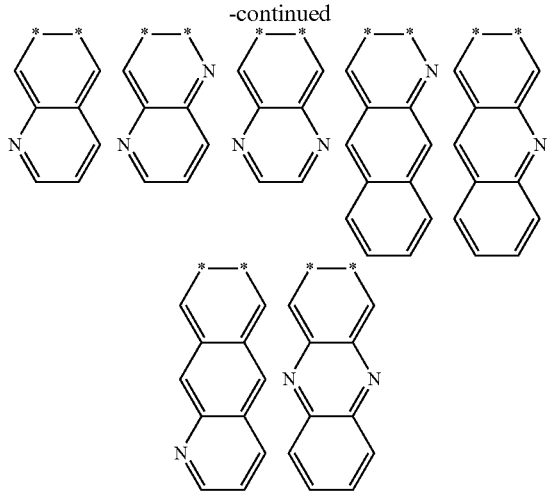

wherein, in Chemical Formula B-2, hydrogen of each aromatic ring is optionally replaced by a halogen, a cyano group, a C1 to C30 alkyl group, a C1 to C30 alkoxy group, a C1 to C30 haloalkyl group, —$SiH_3$, a C1 to C30 alkylsilyl group, a C6 to C30 aryl group, a C6 to C30 aryloxy group, or a C3 to C30 heteroaryl group, and

*'s inside the at least one aromatic ring are linking portions with a carbon of $CR^{xx}$—$CR^{yy}$.

10. The near-infrared absorber of claim 1, wherein in Chemical Formula 1, when $X^2$ is $CR^{xx}$—$CR^{yy}$, the aromatic ring formed by linking $R^{xx}$ with $R^{yy}$ is a moiety represented by Chemical Formula B-3-1 or a moiety represented by Chemical Formula B-3-2, each moiety including at least one aromatic ring:

[Chemical Formula B-3-1]

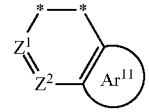

[Chemical Formula B-3-2]

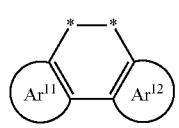

wherein, in Chemical Formulas B-3-1 and B-3-2, $Ar^{11}$ and $Ar^{12}$ are independently a substituted or unsubstituted C6 to C30 arene group or a substituted or unsubstituted C3 to C30 heteroarene group, in Chemical Formula B-3-1, $Z^1$ and $Z^2$ are independently $CR^a$ or N, wherein $R^a$ is hydrogen, deuterium, a C1 to C30 alkyl group, a C1 to C30 haloalkyl group, —$SiH_3$, a C1 to C30 alkylsilyl group, —$NH_2$, a C1 to C30 alkylamine group, a C6 to C30 arylamine group, a C6 to C30 aryl group, C6 to C30 aryloxy group, C3 to C30 heteroaryl group, a halogen, a cyano group, or a combination thereof, hydrogen of each aromatic ring is optionally replaced by a halogen, a cyano group, a C1 to C30 alkyl group, a C1 to C30 alkoxy group, a C1 to C30 haloalkyl group, —$SiH_3$, a C1 to C30 alkylsilyl group, a C6 to C30 aryl group, a C6 to C30 aryloxy group, or a C3 to C30 heteroaryl group, and

*'s inside the at least one aromatic ring are linking portions with a carbon of CR$^{xx}$—CR$^{yy}$.

11. The near-infrared absorber of claim 10, wherein the moiety represented by Chemical Formula B-3-1 is one moiety of a set of moieties represented by Chemical Formula B-3-11, each moiety including at least one aromatic ring, and the moiety represented by Chemical Formula B-3-21, each moiety including at least one aromatic ring:

[Chemical Formula B-3-11]

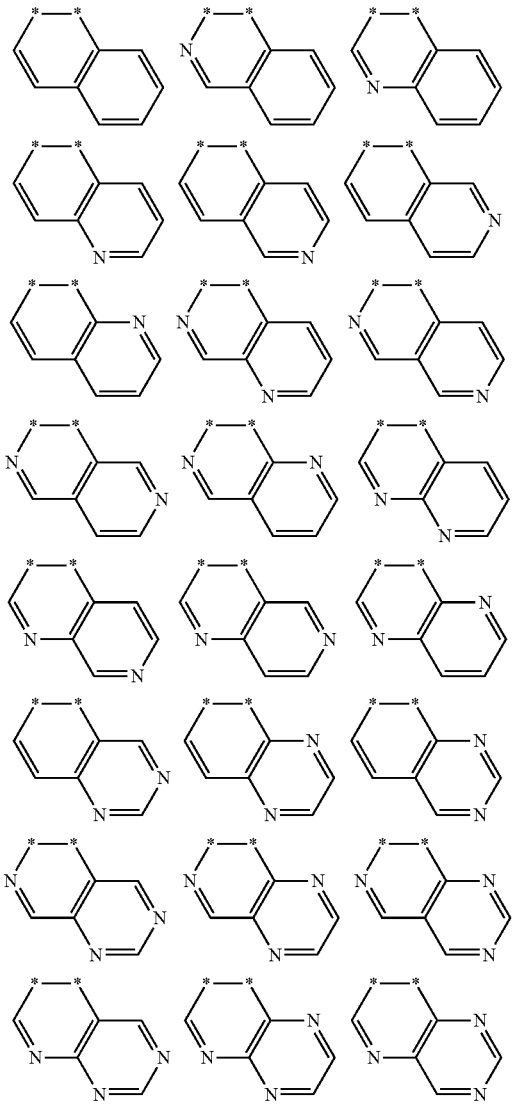

[Chemical Formula B-3-21]

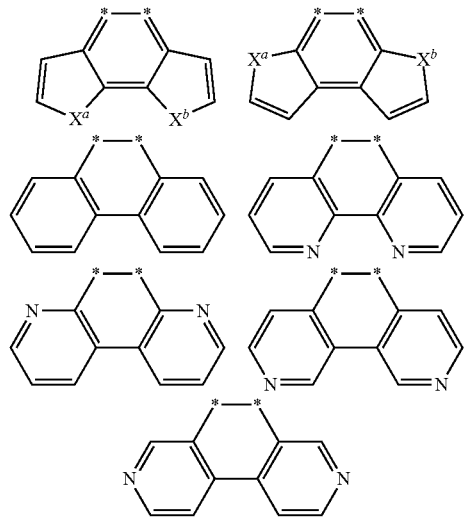

wherein, in Chemical Formula B-3-11,
hydrogen of each aromatic ring is optionally replaced by a halogen, a cyano group, a C1 to C30 alkyl group, a C1 to C30 alkoxy group, a C1 to C30 haloalkyl group, —SiH$_3$, a C1 to C30 alkylsilyl group, a C6 to C30 aryl group, a C6 to C30 aryloxy group, or a C3 to C30 heteroaryl group, and

*'s inside the at least one aromatic ring are linking portions with the carbon of CR$^{xx}$—CR$^{yy}$, wherein, in Chemical Formula B-3-21,
hydrogen of each aromatic ring is optionally replaced by a halogen, a cyano group, a C1 to C30 alkyl group, a C1 to C30 alkoxy group, a C1 to C30 haloalkyl group, —SiH$_3$, a C1 to C30 alkylsilyl group, a C6 to C30 aryl group, a C6 to C30 aryloxy group, or a C3 to C30 heteroaryl group, and X$^a$ and X$^b$ are independently O, S, Se, Te, NR$^a$, SiR$^b$R$^c$, or GeR$^d$R$^e$, wherein R$^a$, R$^b$, R$^c$, R$^d$, and R$^e$ are independently hydrogen, a halogen, a cyano group, a substituted or unsubstituted C1 to C30 alkyl group, a substituted or unsubstituted C1 to C30 alkoxy group, a substituted or unsubstituted C6 to C30 aryl group, or a substituted or unsubstituted C6 to C30 aryloxy group, and

*'s inside the aromatic ring are linking portions with the carbon of CR$^{xx}$—CR$^{yy}$.

12. The near-infrared absorber of claim 1, wherein in Chemical Formula 1, Ar$^1$ and Ar$^2$ are the same or different and are each represented by one of Chemical Formula C-1-1, Chemical Formula C-1-2, or Chemical Formula C-1-3 that each include at least one aromatic ring:

[Chemical Formula C-1-1]

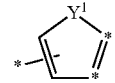

[Chemical Formula C-1-2]

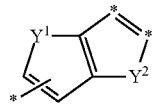

[Chemical Formula C-1-3]

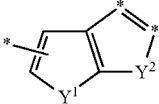

wherein, in Chemical Formulas C-1-1 to C-1-3,
hydrogen of each aromatic ring is optionally replaced by a halogen, a cyano group, a C1 to C30 alkyl group, a C1 to C30 alkoxy group, a C1 to C30 haloalkyl group, —SiH$_3$, a C1 to C30 alkylsilyl group, a C6 to C30 aryl group, a C6 to C30 aryloxy group, or a C3 to C30 heteroaryl group, Y$^1$ is O, S, Se, Te, S(=O), S(=O)$_2$, NR$^{a1}$, SiR$^{b1}$R$^{c1}$, or GeR$^{d1}$R$^{e1}$, wherein R$^{a1}$, R$^{b1}$, R$^{c1}$, R$^{d1}$, and R$^{e1}$ are independently hydrogen, a C1 to C10 alkyl group, a C1 to C10 haloalkyl group, a C1 to C10 alkoxy group, —SiH$_3$, a C1 to C10 alkylsilyl group, —NH$_2$, a C1 to C10 alkylamine group, a C6 to C10 arylamine group, a C6 to C14 aryl group, a C6 to C14 aryloxy group, a C3 to C12 heteroaryl group, a halogen, a cyano group, or a combination thereof, Y$^2$ is O, S, Se, Te, S(=O), S(=O)$_2$, NR$^{a2}$, SiR$^{b2}$R$^{c2}$, GeR$^{d2}$R$^{e2}$, or CR$^{f2}$R$^{g2}$, wherein R$^{a2}$, R$^{b2}$, R$^{c2}$, R$^{d2}$, R$^{e2}$, R$^{f2}$, and R$^{g2}$ are independently hydrogen, a C1 to C10 alkyl group, a C1 to C10 haloalkyl group, a C1 to C10 alkoxy group, —SiH$_3$, a C1 to C10 alkylsilyl group, —NH$_2$, a C1 to C10 alkylamine group, a C6 to C10 arylamine group, a C6 to C14 aryl group, a C6 to C14 aryloxy group, a C3 to C12 heteroaryl group, a halogen, a cyano group, or a combination thereof, R$^{b1}$ and R$^{c1}$, R$^{d1}$ and R$^{e1}$, R$^{b2}$ and R$^{c2}$, R$^{d2}$ and R$^{e2}$, and R$^{f2}$ and R$^{g2}$ are independently present or combined with each other to form a spiro ring, and an * outside the at least one aromatic ring is a linking point with Ar of Chemical Formula 1, and

*'s inside the at least one aromatic ring are linking portions with an N(R$^1$)— containing ring that includes R$^1$ of Chemical Formula 1 and an N(R$^2$)-containing ring that includes R$^2$ of Chemical Formula 1.

13. The near-infrared absorber of claim 1, wherein in Chemical Formula 1, Ar$^1$ and Ar$^2$ are the same or different and are each represented by one of Chemical Formulas C-2-1 to C-2-4 that each include at least one aromatic ring:

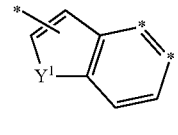

[Chemical Formula C-2-1]

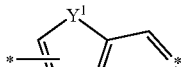

[Chemical Formula C-2-2]

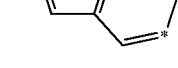

[Chemical Formula C-2-3]

[Chemical Formula C-2-4]

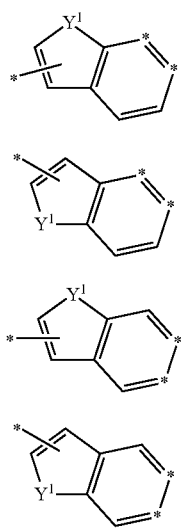

wherein, in Chemical Formulas C-2-1 to C-2-4, hydrogen of each aromatic ring is optionally replaced by a halogen, a cyano group, a C1 to C30 alkyl group, a C1 to C30 alkoxy group, a C1 to C30 haloalkyl group, —SiH$_3$, a C1 to C30 alkylsilyl group, a C6 to C30 aryl group, a C6 to C30 aryloxy group, or a C3 to C30 heteroaryl group, Y$^1$ is O, S, Se, Te, S(=O), S(=O)$_2$, NR$^{a1}$, SiR$^{b1}$R$^{c1}$, or GeR$^{d1}$R$^{e1}$, wherein R$^{a1}$, R$^{b1}$, R$^{c1}$, R$^{d1}$, and R$^{e1}$ are independently hydrogen, a C1 to C10 alkyl group, a C1 to C10 haloalkyl group, a C1 to C10 alkoxy group, —SiH$_3$, a C1 to C10 alkylsilyl group, —NH$_2$, a C1 to C10 alkylamine group, a C6 to C10 arylamine group, a C6 to C14 aryl group, a C6 to C14 aryloxy group, a C3 to C12 heteroaryl group, a halogen, a cyano group, or a combination thereof, R$^{b1}$ and R$^{c1}$ and R$^{d1}$ and R$^{e1}$ are independently present or combined with each other to form a spiro ring, an * outside the at least one aromatic ring is a linking point with Ar of Chemical Formula 1, and

*'s inside the at least one aromatic ring are linking portions with an N(R$^1$)— containing ring that includes R$^1$ of Chemical Formula 1 and an N(R$^2$)-containing ring that includes R$^2$ of Chemical Formula 1.

14. The near-infrared absorber of claim 1, wherein in Chemical Formula 1, Ar$^1$ and Ar$^2$ are the same or different and are each represented by one of Chemical Formulas C-3-1 to C-3-6 that each include at least one aromatic ring:

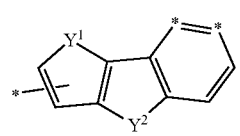

[Chemical Formula C-3-1]

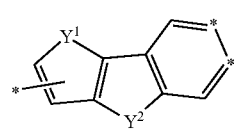

[Chemical Formula C-3-2]

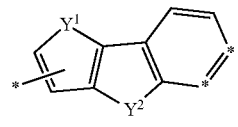

[Chemical Formula C-3-3]

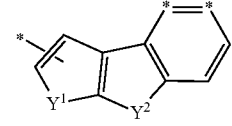

[Chemical Formula C-3-4]

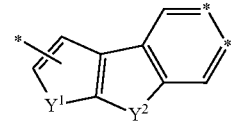

[Chemical Formula C-3-5]

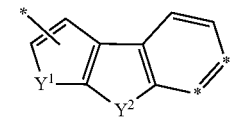

[Chemical Formula C-3-6]

wherein, in Chemical Formulas C-3-1 to C-3-6, hydrogen of each aromatic ring is optionally replaced by a halogen, a cyano group, a C1 to C30 alkyl group, a C1 to C30 alkoxy group, a C1 to C30 haloalkyl group, —SiH$_3$, a C1 to C30 alkylsilyl group, a C6 to C30 aryl group, a C6 to C30 aryloxy group, or a C3 to C30 heteroaryl group, Y$^1$ is O, S, Se, Te, S(=O), S(=O)$_2$, NR$^{a1}$, SiR$^{b1}$R$^{c1}$, or GeR$^{d1}$R$^{e1}$, wherein R$^{a1}$, R$^{b1}$, R$^{c1}$, R$^{d1}$, and R$^{e1}$ are independently hydrogen, a C1 to C10 alkyl group, a C1 to C10 haloalkyl group, a C1 to C10 alkoxy group, —SiH$_3$, a C1 to C10 alkylsilyl group, —NH$_2$, a C1 to C10 alkylamine group, a C6 to C10 arylamine group, a C6 to C14 aryl group, a C6 to C14 aryloxy group, a C3 to C12 heteroaryl group, a halogen, a cyano group, or a combination thereof, $Y^2$ is O, S, Se, Te, S(=O), S(=O)$_2$, NR$^{a2}$, SiR$^{b2}$R$^{c2}$, GeR$^{d2}$R$^{e2}$, or CR$^{f2}$R$^{g2}$, wherein R$^{a2}$, R$^{b2}$, R$^{c2}$, R$^{d2}$, R$^{e2}$, R$^{f2}$, and R$^{g2}$ are independently hydrogen, a C1 to C10 alkyl group, a C1 to C10 haloalkyl group, a C1 to C10 alkoxy group, —SiH$_3$, a C1 to C10 alkylsilyl group, —NH$_3$, a C1 to C10 alkylamine group, a C6 to C10 arylamine group, a C6 to C14 aryl group, a C6 to C14 aryloxy group, a C3 to C12 heteroaryl group, a halogen, a cyano group, or a combination thereof, R$^{b1}$ and R$^{c1}$, R$^{d1}$ and R$^{e1}$, R$^{b2}$ and R$^{c2}$, R$^{d2}$ and R$^{e2}$, and R$^{f2}$ and R$^{g2}$ are independently present or combined with each other to form a spiro ring, an * outside the at least one aromatic ring is a linking point with Ar of Chemical Formula 1, and

*'s inside the at least one aromatic ring are linking portions with an N(R$^1$)— containing ring that includes R$^1$ of Chemical Formula 1 and an N(R$^2$)-containing ring that includes R$^2$ of Chemical Formula 1.

15. The near-infrared absorber of claim 1, wherein in Chemical Formula 1, Ar$^1$ and Ar$^2$ are the same or different and each represented by one of Chemical Formula C-4-1 or Chemical Formula C-4-2 that each include at least one aromatic ring:

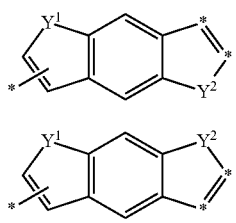

[Chemical Formula C-4-1]

[Chemical Formula C-4-2]

wherein, in Chemical Formulas C-4-1 and C-4-2, hydrogen of each aromatic ring is optionally replaced by a halogen, a cyano group, a C1 to C30 alkyl group, a C1 to C30 alkoxy group, a C1 to C30 haloalkyl group, —SiH$_3$, a C1 to C30 alkylsilyl group, a C6 to C30 aryl group, a C6 to C30 aryloxy group, or a C3 to C30 heteroaryl group, $Y^1$ is O, S, Se, Te, S(=O), S(=O)$_2$, NR$^{a1}$, SiR$^{b1}$R$^{c1}$, or GeR$^{d1}$R$^{e1}$, wherein R$^{a1}$, R$^{b1}$, R$^{c1}$, R$^{d1}$, and R$^{e1}$ are independently hydrogen, a C1 to C10 alkyl group, a C1 to C10 haloalkyl group, a C1 to C10 alkoxy group, —SiH$_3$, a C1 to C10 alkylsilyl group, —NH$_3$, a C1 to C10 alkylamine group, a C6 to C10 arylamine group, a C6 to C14 aryl group, a C6 to C14 aryloxy group, a C3 to C12 heteroaryl group, a halogen, a cyano group, or a combination thereof, $Y^2$ is O, S, Se, Te, S(=O), S(=O)$_2$, NR$^{a2}$, SiR$^{b2}$R$^{c2}$, GeR$^{d2}$R$^{e2}$, or CR$^{f2}$R$^{g2}$, wherein R$^{a2}$, R$^{b2}$, R$^{c2}$, R$^{d2}$, R$^{e2}$, R$^{f2}$, and R$^{g2}$ are independently hydrogen, a C1 to C10 alkyl group, a C1 to C10 haloalkyl group, a C1 to C10 alkoxy group, —SiH$_3$, a C1 to C10 alkylsilyl group, —NH$_3$, a C1 to C10 alkylamine group, a C6 to C10 arylamine group, a C6 to C14 aryl group, a C6 to C14 aryloxy group, a C3 to C12 heteroaryl group, a cyano group, or a combination thereof, R$^{b1}$ and R$^{c1}$, R$^{d1}$ and R$^{e1}$, R$^{b2}$ and R$^{c2}$, R$^{d2}$ and R$^{e2}$, and R$^{f2}$ and R$^{g2}$ are independently present or combined with each other to form a spiro ring, an * outside the at least one aromatic ring is a linking point with Ar of Chemical Formula 1, and

*'s inside the aromatic ring are linking portions with an N(R$^1$)-containing ring that includes R$^1$ of Chemical Formula 1 and an N(R$^2$)-containing ring that includes R$^2$ of Chemical Formula 1.

16. The near-infrared absorber of claim 1, wherein in Chemical Formula 1, Ar$^1$ and Ar$^2$ are the same or different and are each represented by one of Chemical Formulas C-5-1 to C-5-8 that each include at least one aromatic ring:

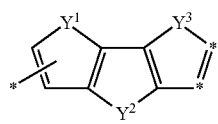

[Chemical Fromula C-5-1]

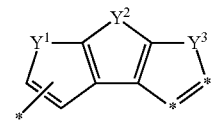

[Chemical Fromula C-5-2]

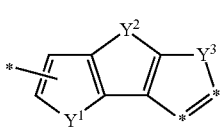

[Chemical Fromula C-5-3]

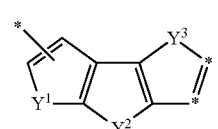

[Chemical Fromula C-5-4]

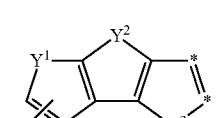

[Chemical Fromula C-5-5]

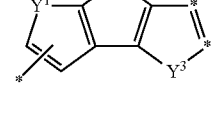

[Chemical Fromula C-5-6]

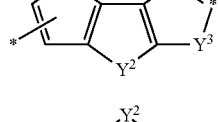

[Chemical Fromula C-5-7]

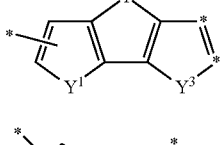

[Chemical Fromula C-5-8]

wherein, in Chemical Formulas C-5-1 to C-5-8, hydrogen of each aromatic ring is optionally replaced by a halogen, a cyano group, a C1 to C30 alkyl group, a C1 to C30 alkoxy group, a C1 to C30 haloalkyl group, —SiH$_3$, a C1 to C30 alkylsilyl group, a C6 to C30 aryl group, a C6 to C30 aryloxy group, or a C3 to C30 heteroaryl group, $Y^1$ is O, S, Se, Te, S(=O), S(=O)$_2$, NR$^{a1}$, SiR$^{b1}$R$^{c1}$, or GeR$^{d1}$R$^{e1}$, wherein R$^{a1}$, R$^{b1}$, R$^{c1}$, R$^{d1}$, and R$^{e1}$ are independently hydrogen, a C1 to C10 alkyl group, a C1 to C10 haloalkyl group, a C1 to C10 alkoxy group, —SiH$_3$, a C1 to C10 alkylsilyl group, —NH$_3$, a C1 to C10 alkylamine group, a C6 to C10 arylamine group, a C6 to C14 aryl group, a C6 to C14 aryloxy group, a C3 to C12 heteroaryl group, a halogen, a cyano group, or a combination thereof, Y$^2$ and Y$^3$ are independently O, S, Se, Te, S(=O), S(=O)$_2$, NR$^{a2}$, SiR$^{b2}$R$^{c2}$, GeR$^{d2}$R$^{e2}$, or CR$^{f2}$R$^{g2}$, wherein R$^{a2}$, R$^{b2}$, R$^{c2}$, R$^{d2}$, R$^{e2}$, R$^{f2}$, and R$^{g2}$ are independently hydrogen, a C1 to C10 alkyl group, a C1 to C10 haloalkyl group, a C1 to C10 alkoxy group, —SiH$_3$, a C1 to C10 alkylsilyl group, —NH$_3$, a C1 to C10 alkylamine group, a C6 to C10 arylamine group, a C6 to C14 aryl group, a C6 to C14 aryloxy group, a C3 to C12 heteroaryl group, a halogen, a cyano group, or a combination thereof, R$^{b1}$ and R$^{c1}$, R$^{d1}$ and R$^{e1}$, R$^{b2}$ and R$^{c2}$, R$^{d2}$ and R$^{e2}$, and R$^{f2}$ and R$^{g2}$ are independently present or combined with each other to form a spiro ring, an * outside the at least one aromatic ring is a linking point with Ar of Chemical Formula 1, and

*'s inside the at least one aromatic ring are linking portions with an N(R$^1$)— containing ring that includes R$^1$ of Chemical Formula 1 and an N(R$^2$)-containing ring that includes R$^2$ of Chemical Formula 1.

17. The near-infrared absorber of claim 1, wherein the near-infrared absorber has a peak absorption wavelength in a wavelength region of about 750 nm to about 3000 nm.

18. A near-infrared absorbing/blocking film comprising the near-infrared absorber of claim 1.

19. A photoelectric device, comprising:
a first electrode and a second electrode facing each other; and
an active layer between the first electrode and the second electrode,
wherein the active layer includes a near-infrared absorber that includes a compound represented by Chemical Formula 1:

[Chemical Formula 1]

wherein, in Chemical Formula 1,
Ar is a substituted or unsubstituted C6 to C30 aromatic ring, a substituted or unsubstituted C3 to C30 heteroaromatic ring, or a combination thereof,
X$^1$ is O, S, Se, Te, S(=O), S(=O)$_2$), NR$^a$, CR$^b$R$^c$, SiR$^d$R$^e$, GeR$^f$R$^g$, CR$^h$=CR$^i$, or CR$^{hh}$=CR$^{ii}$, wherein R$^a$, R$^b$, R$^c$, R$^d$, R$^e$, R$^f$, R$^g$, R$^h$, and R$^i$ are independently hydrogen, deuterium, a C1 to C30 alkyl group, a C1 to C30 haloalkyl group, a C6 to C30 aryl group, a C6 to C30 aryloxy group, a C3 to C30 heteroaryl group, a halogen, a cyano group, or a combination thereof, R$^{hh}$ and R$^{ii}$ are independently (CH)$_w$ where w is a positive integer or at least one heteroatom of O, N, S, Se, or Te, and R$^{hh}$ and R$^{ii}$ are linked to each other to form an aromatic ring or a heteroaromatic ring, X$^2$ is O, S, Se, Te, C, CR$^x$—CR$^y$, CR$^{xx}$—CR$^{yy}$, S(=O) or S=O$_2$, wherein R$^x$ and R$^y$ are independently hydrogen, deuterium, a C1 to C30 alkyl group, a C1 to C30 haloalkyl group, a C6 to C30 aryl group, a C6 to C30 aryloxy group, a C3 to C30 heteroaryl group, a halogen, a cyano group, or a combination thereof, R$^{xx}$ and R$^{yy}$ are independently (CH)$_v$ where v is a positive integer or at least one heteroatom of O, N, S, Se, or Te, and R$^{xx}$ and R$^{yy}$ are linked to each other to form an aromatic ring or a heteroaromatic ring, Ar$^1$ and Ar$^2$ are independently a heteroarene group including at least one heteroatom of O, S, Se, or Te, Ar$^3$ and Ar$^4$ are independently a substituted or unsubstituted C6 to C30 arene group, a substituted or unsubstituted C3 to C30 heteroarene group, or a condensed ring group thereof, R$^1$ and R$^2$ are independently hydrogen, deuterium, a halogen, a cyano group, a nitro group, a hydroxyl group, a substituted or unsubstituted C1 to C10 alkyl group, a substituted or unsubstituted C1 to C10 alkoxy group, a substituted or unsubstituted C6 to C10 aryl group, or a substituted or unsubstituted C3 to C10 heteroaryl group, and L$^1$ and L$^2$ are independently a single bond, —O—, —S—, —Se—, —Te—, —N=, —NR$^a$—, —SiR$^b$R$^c$—, —GeR$^d$R$^e$—, —(CR$^f$R$^g$)$_n$—, or —(C(R$^h$)=C(R$^i$))—, wherein R$^a$, R$^b$, R$^c$, R$^d$, R$^e$, R$^f$, R$^g$, R$^h$, and R$^i$ are independently hydrogen, deuterium, a halogen, a cyano group, a substituted or unsubstituted C1 to C10 alkyl group, or a substituted or unsubstituted C6 to C10 aryl group, wherein R$^b$ and R$^c$, R$^d$ and R$^e$, R$^f$ and R$^g$, or R$^h$ and R$^i$ are independently present or are linked to each other to form a separate ring, and n of —(CR$^f$R$^g$)$_n$— is an integer of 1 or 2.

20. The photoelectric device of claim 19, wherein in Chemical Formula 1, Ar is benzene ring, a substituted or unsubstituted naphthalene ring, a substituted or unsubstituted anthracene ring, a substituted or unsubstituted phenanthrene ring, a substituted or unsubstituted tetracene ring, or a substituted or unsubstituted pyrene ring.

21. The photoelectric device of claim 19, wherein in Chemical Formula 1, Ar is a substituted or unsubstituted quinoline ring, a substituted or unsubstituted isoquinoline ring, a substituted or unsubstituted quinoxaline ring, a substituted or unsubstituted quinazoline ring, or a substituted or unsubstituted phenanthroline ring.

22. The photoelectric device of claim 19, wherein in Chemical Formula 1, Ar is one moiety of a set of moieties represented by Chemical Formula A-1, each moiety including at least one aromatic ring and left and right linking groups:

[Chemical Formula A-1]

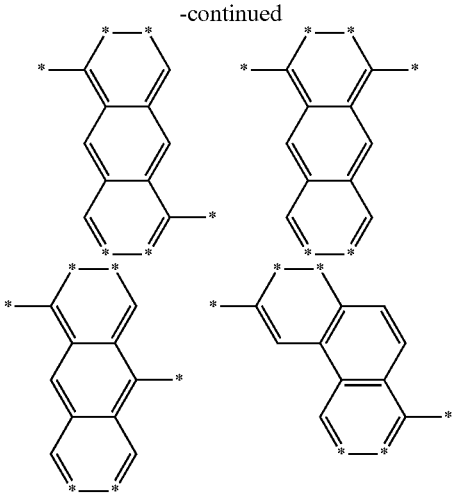

wherein, in Chemical Formula A-1,
hydrogen of each aromatic ring is optionally replaced by a halogen, a cyano group, a C1 to C10 alkyl group, a C1 to C10 alkoxy group, a C1 to C10 haloalkyl group, —SiH$_3$, or a C1 to C10 alkylsilyl group, separate adjacent pairs of *'s inside the at least one aromatic ring are linking portions with separate, respective ones of an N—X$^1$—N— containing ring of Chemical Formula 1 or —N=X$^2$=N-containing ring of Chemical Formula 1, and

*'s of the left and right linking groups are portions linked to separate, respective ones of Ar$^1$ or Ar$^2$ of Chemical Formula 1.

23. The photoelectric device of claim 19, wherein in Chemical Formula 1, Ar is one moiety of a set of moieties represented by Chemical Formula A-2, each moiety including at least one aromatic ring and left and right linking groups:

[Chemical Formula A-2]

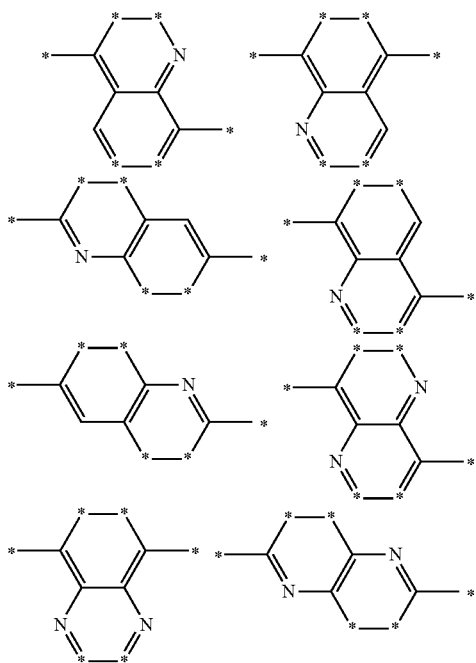

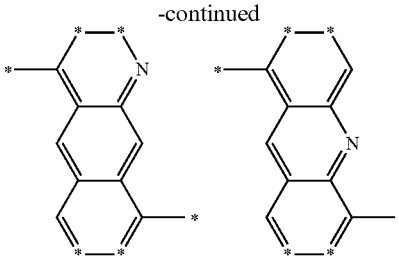

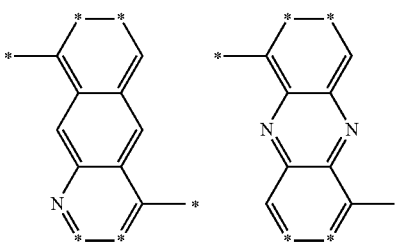

wherein, in Chemical Formula A-2,
hydrogen of each aromatic ring is optionally replaced by a halogen, a cyano group, a C1 to C10 alkyl group, a C1 to C10 alkoxy group, a C1 to C10 haloalkyl group, —SiH$_3$, or a C1 to C10 alkylsilyl group, separate adjacent pairs of *'s inside the at least one aromatic ring are linking portions with separate, respective ones of an N—X$^1$—N-containing ring of Chemical Formula 1 and an —N=X$^2$=N-containing ring of Chemical Formula 1, and

*'s of the left and right linking groups are portions linked to separate, respective ones of Ar$^1$ and Ar$^2$ of Chemical Formula 1.

24. The photoelectric device of claim 19, wherein in Chemical Formula 1, when X$^2$ is CR$^{xx}$—CR$^{yy}$, the aromatic ring formed by linking R$^{xx}$ with R$^{yy}$ is a substituted or unsubstituted benzene ring, a substituted or unsubstituted naphthalene ring, a substituted or unsubstituted acenaphthene ring, a substituted or unsubstituted anthracene ring, a substituted or unsubstituted phenanthrene ring, a substituted or unsubstituted tetracene ring, or a substituted or unsubstituted pyrene ring.

25. The photoelectric device of claim 19, wherein in Chemical Formula 1, when X$^2$ is CR$^{xx}$—CR$^{yy}$, the aromatic ring formed by linking R$^{xx}$ with R$^{yy}$ is a substituted or unsubstituted quinoline ring, a substituted or unsubstituted isoquinoline ring, a substituted or unsubstituted quinoxaline ring, a substituted or unsubstituted quinazoline ring, a substituted or unsubstituted phenanthroline ring, a substituted or unsubstituted pyrimidine ring, or a substituted or unsubstituted benzodithiophene ring.

26. The photoelectric device of claim 19, wherein in Chemical Formula 1, when X$^2$ is CR$^{xx}$—CR$^{yy}$, the aromatic ring formed by linking R$^{xx}$ with R$^{yy}$ is one moiety of a set of moieties represented by Chemical Formula B-1, each moiety including at least one aromatic ring:

[Chemical Formula B-1]

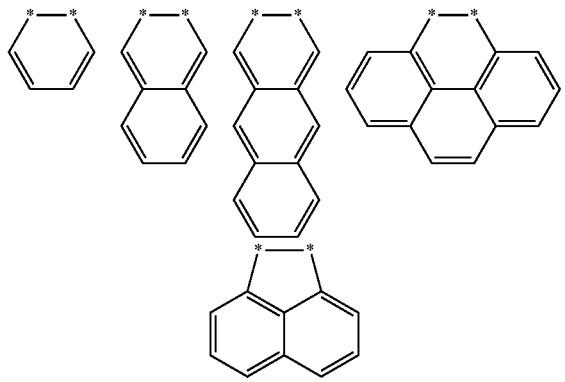

wherein, in Chemical Formula B-1, hydrogen of each aromatic ring is optionally replaced by a halogen, a cyano group, a C1 to C30 alkyl group, a C1 to C30 alkoxy group, a C1 to C30 haloalkyl group, —SiH$_3$, a C1 to C30 alkylsilyl group, a C6 to C30 aryl group, a C6 to C30 aryloxy group, or a C3 to C30 heteroaryl group, and

*'s inside the at least one aromatic ring are linking portions with a carbon of CR$^{xx}$—CR$^{yy}$.

27. The photoelectric device of claim 19, wherein in Chemical Formula 1, when X$^2$ is CR$^{xx}$—CR$^{yy}$, the aromatic ring formed by linking R$^{xx}$ with R$^{yy}$ is one moiety of a set of moieties represented by Chemical Formula B-2, each moiety including at least one aromatic ring:

[Chemical Formula B-2]

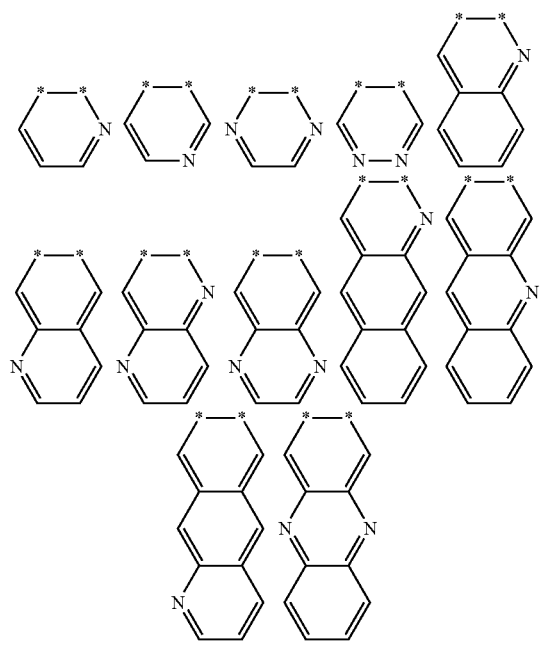

wherein, in Chemical Formula B-2, hydrogen of each aromatic ring is optionally replaced by a halogen, a cyano group, a C1 to C30 alkyl group, a C1 to C30 alkoxy group, a C1 to C30 haloalkyl group, —SiH$_3$, a C1 to C30 alkylsilyl group, a C6 to C30 aryl group, a C6 to C30 aryloxy group, or a C3 to C30 heteroaryl group, and

*'s inside the at least one aromatic ring are linking portions with a carbon of CR$^{xx}$—CR$^{yy}$.

28. The photoelectric device of claim 19, wherein in Chemical Formula 1, when X$^2$ is CR$^{xx}$—CR$^{yy}$, the aromatic ring formed by linking R$^{xx}$ with R$^{yy}$ is a moiety represented by Chemical Formula B-3-1 or a moiety represented by Chemical Formula B-3-2, each moiety including at least one aromatic ring:

[Chemical Formula B-3-1]

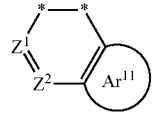

[Chemical Formula B-3-2]

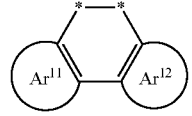

wherein, in Chemical Formulas B-3-1 and B-3-2,

Ar$^{11}$ and Ar$^{12}$ are independently a substituted or unsubstituted C6 to C30 arene group or a substituted or unsubstituted C3 to C30 heteroarene group, in Chemical Formula B-3-1, Z$^1$ and Z$^2$ are independently CR$^a$ or N, wherein R$^a$ is hydrogen, deuterium, a C1 to C30 alkyl group, a C1 to C30 haloalkyl group, —SiH$_3$, a C1 to C30 alkylsilyl group, —NH$_2$, a C1 to C30 alkylamine group, a C6 to C30 arylamine group, a C6 to C30 aryl group, C6 to C30 aryloxy group, C3 to C30 heteroaryl group, a halogen, a cyano group, or a combination thereof, hydrogen of each aromatic ring is optionally replaced by a halogen, a cyano group, a C1 to C30 alkyl group, a C1 to C30 alkoxy group, a C1 to C30 haloalkyl group, —SiH$_3$, a C1 to C30 alkylsilyl group, a C6 to C30 aryl group, a C6 to C30 aryloxy group, or a C3 to C30 heteroaryl group, and

*'s inside the at least one aromatic ring are linking portions with a carbon of CR$^{xx}$—CR$^{yy}$.

29. The photoelectric device of claim 28, wherein the moiety represented by Chemical Formula B-3-1 is one moiety of a set of moieties represented by Chemical Formula B-3-11, each moiety including at least one aromatic ring, and the moiety represented by Chemical Formula B-3-21, each moiety including at least one aromatic ring:

[Chemical Formula B-3-11]

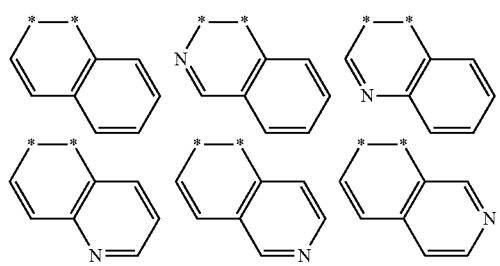

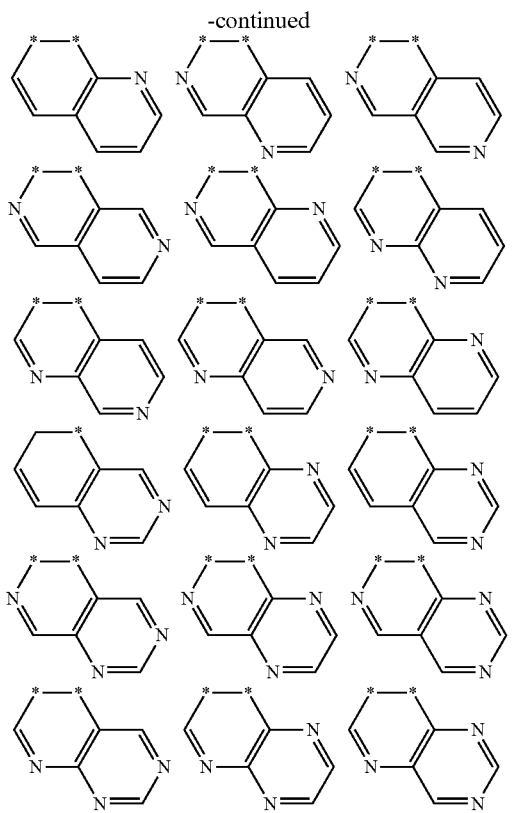

wherein, in Chemical Formula B-3-11,
hydrogen of each aromatic ring is optionally replaced by a halogen, a cyano group, a C1 to C30 alkyl group, a C1 to C30 alkoxy group, a C1 to C30 haloalkyl group, —SiH₃, a C1 to C30 alkylsilyl group, a C6 to C30 aryl group, a C6 to C30 aryloxy group, or a C3 to C30 heteroaryl group, and

*'s inside the at least one aromatic ring are linking portions with the carbon of $CR^{xx}$—$CR^{yy}$,

[Chemical Formula B-3-21]

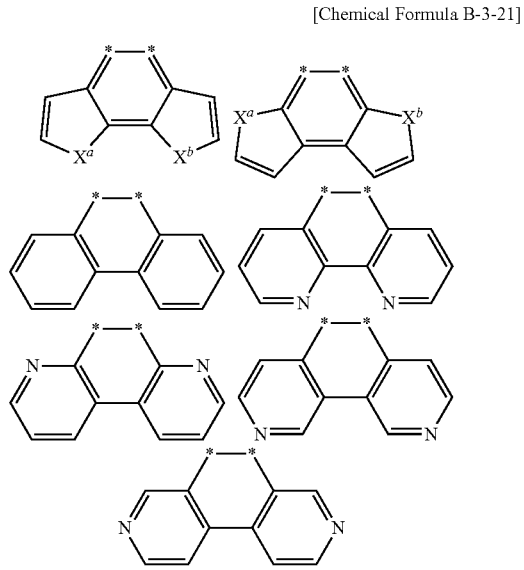

wherein, in Chemical Formula B-3-21,
hydrogen of each aromatic ring is optionally replaced by a halogen, a cyano group, a C1 to C30 alkyl group, a C1 to C30 alkoxy group, a C1 to C30 haloalkyl group, —SiH₃, a C1 to C30 alkylsilyl group, a C6 to C30 aryl group, a C6 to C30 aryloxy group, or a C3 to C30 heteroaryl group, $X^a$ and $X^b$ are independently O, S, Se, Te, $NR^a$, $SiR^bR^c$, or $GeR^dR^e$, wherein $R^a$, $R^b$, $R^c$, $R^d$, and $R^e$ are independently hydrogen, a halogen, a cyano group, a substituted or unsubstituted C1 to C30 alkyl group, a substituted or unsubstituted C1 to C30 alkoxy group, a substituted or unsubstituted C6 to C30 aryl group, or a substituted or unsubstituted C6 to C30 aryloxy group, and

*'s inside the at least one aromatic ring are linking portions with the carbon of $CR^{xx}$—$CR^{yy}$.

30. The photoelectric device of claim 19, wherein in Chemical Formula 1, $Ar^1$ and $Ar^2$ are the same or different and each represented by one of Chemical Formula C-1-1, Chemical Formula C-1-2, or Chemical Formula C-1-3 that each include at least one aromatic ring:

[Chemical Formula C-1-1]

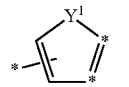

[Chemical Formula C-1-2]

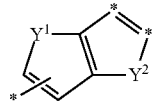

[Chemical Formula C-1-3]

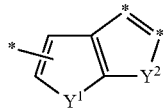

wherein, in Chemical Formulas C-1-1 to C-1-3,
hydrogen of each aromatic ring is optionally replaced by a halogen, a cyano group, a C1 to C30 alkyl group, a C1 to C30 alkoxy group, a C1 to C30 haloalkyl group, —SiH₃, a C1 to C30 alkylsilyl group, a C6 to C30 aryl group, a C6 to C30 aryloxy group, or a C3 to C30 heteroaryl group, $Y^1$ is O, S, Se, Te, S(=O), S(=O)₂, $NR^{a1}$, $SiR^{b1}R^{c1}$, or $GeR^{d1}R^{e1}$, wherein $R^{a1}$, $R^{b1}$, $R^{c1}$, $R^{d1}$, and $R^{e1}$ are independently hydrogen, a C1 to C10 alkyl group, a C1 to C10 haloalkyl group, a C1 to C10 alkoxy group, —SiH₃, a C1 to C10 alkylsilyl group, —NH₃, a C1 to C10 alkylamine group, a C6 to C10 arylamine group, a C6 to C14 aryl group, a C6 to C14 aryloxy group, a C3 to C12 heteroaryl group, a halogen, a cyano group, or a combination thereof, $Y^2$ is O, S, Se, Te, S(=O), S(=O)₂, $NR^{a2}$, $SiR^{b2}R^{c2}$, $GeR^{d2}R^{e2}$, or $CR^{f2}R^{g2}$, wherein $R^{a2}$, $R^{b2}$, $R^{c2}$, $R^{d2}$, $R^{e2}$, $R^{f2}$, and $R^{g2}$ are independently hydrogen, a C1 to C10 alkyl group, a C1 to C10 haloalkyl group, a C1 to C10 alkoxy group, —SiH₃, a C1 to C10 alkylsilyl group, —NH₃, a C1 to C10 alkylamine group, a C6 to C10 arylamine group, a C6 to C14 aryl group, a C6 to C14 aryloxy group, a C3 to C12 heteroaryl group, a halogen, a cyano group, or a combination thereof, $R^{b1}$ and $R^{c1}$, $R^{d1}$ and $R^{e1}$, $R^{b2}$ and $R^{c2}$, $R^{d2}$ and $R^{e2}$, and $R^{f2}$ and $R^{g2}$ are independently present or combined with each other to form a spiro ring, an * outside the at least one aromatic ring is a linking point with Ar of Chemical Formula 1, and

*'s inside the at least one aromatic ring are linking portions with an N(R¹)— containing ring that includes R¹ of Chemical Formula 1 and an N(R²)-containing ring that includes R² of Chemical Formula 1.

31. The photoelectric device of claim 19, wherein in Chemical Formula 1, Ar¹ and Ar² are the same or different and are represented by one of Chemical Formulas C-2-1 to C-2-4 that each include at least one aromatic ring:

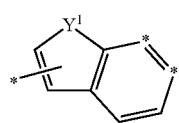

[Chemical Formula C-2-1]

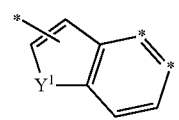

[Chemical Formula C-2-2]

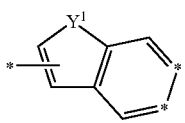

[Chemical Formula C-2-3]

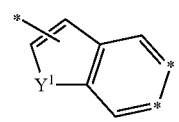

[Chemical Formula C-2-4]

wherein, in Chemical Formulas C-2-1 to C-2-4, hydrogen of each aromatic ring is optionally replaced by a halogen, a cyano group, a C1 to C30 alkyl group, a C1 to C30 alkoxy group, a C1 to C30 haloalkyl group, —SiH₃, a C1 to C30 alkylsilyl group, a C6 to C30 aryl group, a C6 to C30 aryloxy group, or a C3 to C30 heteroaryl group, Y¹ is O, S, Se, Te, S(=O), S(=O)₂, NR$^{a1}$, SiR$^{b1}$R$^{c1}$, or GeR$^{d1}$R$^{e1}$, wherein R$^{a1}$, R$^{b1}$, R$^{c1}$, R$^{d1}$, and R$^{e1}$ are independently hydrogen, a C1 to C10 alkyl group, a C1 to C10 haloalkyl group, a C1 to C10 alkoxy group, —SiH₃, a C1 to C10 alkylsilyl group, —NH₃, a C1 to C10 alkylamine group, a C6 to C10 arylamine group, a C6 to C14 aryl group, a C6 to C14 aryloxy group, a C3 to C12 heteroaryl group, a halogen, a cyano group, or a combination thereof, R$^{b1}$ and R$^{c1}$ and R$^{d1}$ and R$^{e1}$ are independently present or combined with each other to form a spiro ring, an * outside the at least one aromatic ring is a linking point with Ar of Chemical Formula 1, and

*'s inside the at least one aromatic ring are linking portions with an N(R¹)— containing ring that includes R¹ of Chemical Formula 1 and an N(R²)-containing ring that includes R² of Chemical Formula 1.

32. The photoelectric device of claim 19, wherein in Chemical Formula 1, Ar¹ and Ar² are the same or different and are each represented by one of Chemical Formulas C-3-1 to C-3-6 that each include at least one aromatic ring:

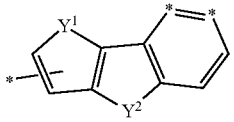

[Chemical Formula C-3-1]

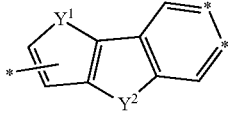

[Chemical Formula C-3-2]

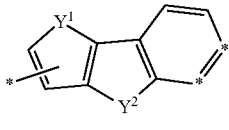

[Chemical Formula C-3-3]

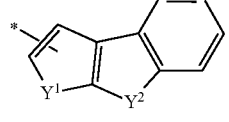

[Chemical Formula C-3-4]

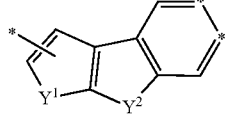

[Chemical Formula C-3-5]

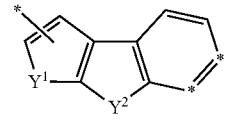

[Chemical Formula C-3-6]

wherein, in Chemical Formulas C-3-1 to C-3-6, hydrogen of each aromatic ring is optionally replaced by a halogen, a cyano group, a C1 to C30 alkyl group, a C1 to C30 alkoxy group, a C1 to C30 haloalkyl group, —SiH₃, a C1 to C30 alkylsilyl group, a C6 to C30 aryl group, a C6 to C30 aryloxy group, or a C3 to C30 heteroaryl group, Y¹ is O, S, Se, Te, S(=O), S(=O)₂, NR$^{a1}$, SiR$^{b1}$R$^{c1}$, or GeR$^{d1}$R$^{e1}$, wherein R$^{a1}$, R$^{b1}$, R$^{c1}$, R$^{d1}$, and R$^{e1}$ are independently hydrogen, a C1 to C10 alkyl group, a C1 to C10 haloalkyl group, a C1 to C10 alkoxy group, —SiH₃, a C1 to C10 alkylsilyl group, —NH₃, a C1 to C10 alkylamine group, a C6 to C10 arylamine group, a C6 to C14 aryl group, a C6 to C14 aryloxy group, a C3 to C12 heteroaryl group, a halogen, a cyano group, or a combination thereof, Y² is O, S, Se, Te, S(=O), S(=O)₂, NR$^{a2}$, SiR$^{b2}$R$^{c2}$, GeR$^{d2}$R$^{e2}$, or CR$^{f2}$R$^{g2}$, wherein R$^{a2}$, R$^{b2}$, R$^{c2}$, R$^{d2}$, R$^{e2}$, R$^{f2}$, and R$^{g2}$ are independently hydrogen, a C1 to C10 alkyl group, a C1 to C10 haloalkyl group, a C1 to C10 alkoxy group, —SiH₃, a C1 to C10 alkylsilyl group, —NH₃, a C1 to C10 alkylamine group, a C6 to C10 arylamine group, a C6 to C14 aryl group, a C6 to C14 aryloxy group, a C3 to C12 heteroaryl group, a halogen, a cyano group, or a combination thereof, R$^{b1}$ and R$^{c1}$, R$^{d1}$ and R$^{e1}$, R$^{b2}$ and R$^{c2}$, R$^{d2}$ and R$^{e2}$, and R$^{f2}$ and R$^{g2}$ are independently present or combined with each other to form a spiro ring, an * outside the at least one aromatic ring is a linking point with Ar of Chemical Formula 1, and

*'s inside the at least one aromatic ring are linking portions with an N(R¹)— containing ring that includes R¹ of Chemical Formula 1 and an N(R²)-containing ring that includes R² of Chemical Formula 1.

33. The photoelectric device of claim 19, wherein in Chemical Formula 1, Ar¹ and Ar² are the same or different and are each represented by one of Chemical Formula C-4-1 or Chemical Formula C-4-2 that each include at least one aromatic ring:

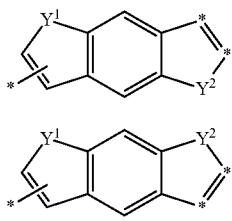

[Chemical Formula C-4-1]

[Chemical Formula C-4-2]

wherein, in Chemical Formulas C-4-1 and C-4-2,
hydrogen of each aromatic ring is optionally replaced by a halogen, a cyano group, a C1 to C30 alkyl group, a C1 to C30 alkoxy group, a C1 to C30 haloalkyl group, —SiH₃, a C1 to C30 alkylsilyl group, a C6 to C30 aryl group, a C6 to C30 aryloxy group, or a C3 to C30 heteroaryl group,
$Y^1$ is O, S, Se, Te, S(=O), S(=O)₂, $NR^{a1}$, $SiR^{b1}R^{c1}$, or $GeR^{d1}R^{e1}$, wherein $R^{a1}$, $R^{b1}$, $R^{c1}$, $R^{d1}$, and $R^{e1}$ are independently hydrogen, a C1 to C10 alkyl group, a C1 to C10 haloalkyl group, a C1 to C10 alkoxy group, —SiH₃, a C1 to C10 alkylsilyl group, —NH₃, a C1 to C10 alkylamine group, a C6 to C10 arylamine group, a C6 to C14 aryl group, a C6 to C14 aryloxy group, a C3 to C12 heteroaryl group, a halogen, a cyano group, or a combination thereof,
$Y^2$ is O, S, Se, Te, S(=O), S(=O)₂, $NR^{a2}$, $SiR^{b2}R^{c2}$, $GeR^{d2}R^{e2}$, or $CR^{f2}R^{g2}$, wherein $R^{a2}$, $R^{b2}$, $R^{c2}$, $R^{d2}$, $R^{e2}$, $R^{f2}$, and $R^{g2}$ are independently hydrogen, a C1 to C10 alkyl group, a C1 to C10 haloalkyl group, a C1 to C10 alkoxy group, —SiH₃, a C1 to C10 alkylsilyl group, —NH₃, a C1 to C10 alkylamine group, a C6 to C10 arylamine group, a C6 to C14 aryl group, a C6 to C14 aryloxy group, a C3 to C12 heteroaryl group, a halogen, a cyano group, or a combination thereof,
$R^{b1}$ and $R^{c1}$, $R^{d1}$ and $R^{e1}$, $R^{b2}$ and $R^{c2}$, $R^{d2}$ and $R^{e2}$, and $R^{f2}$ and $R^{g2}$ are independently present or combined with each other to form a spiro ring,
an * outside the at least one aromatic ring is a linking point with Ar of Chemical Formula 1, and
*'s inside the aromatic ring are linking portions with an N(R¹)-containing ring that includes R¹ of Chemical Formula 1 and an N(R²)-containing ring that includes R² of Chemical Formula 1.

34. The photoelectric device of claim 19, wherein in Chemical Formula 1, Ar¹ and Ar² are the same or different and are each represented by one of Chemical Formulas C-5-1 to C-5-8 that each include at least one aromatic ring:

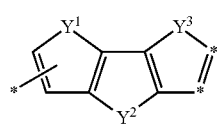

[Chemical Formula C-5-1]

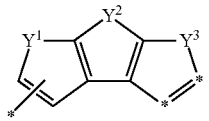

[Chemical Fromula C-5-2]

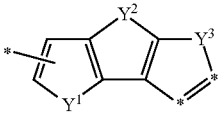

[Chemical Fromula C-5-3]

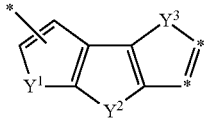

[Chemical Fromula C-5-4]

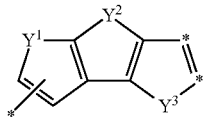

[Chemical Fromula C-5-5]

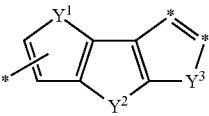

[Chemical Fromula C-5-6]

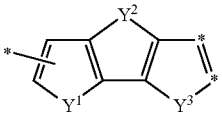

[Chemical Fromula C-5-7]

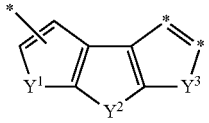

[Chemical Fromula C-5-8]

wherein, in Chemical Formulas C-5-1 to C-5-8,
hydrogen of each aromatic ring is optionally replaced by a halogen, a cyano group, a C1 to C30 alkyl group, a C1 to C30 alkoxy group, a C1 to C30 haloalkyl group, —SiH₃, a C1 to C30 alkylsilyl group, a C6 to C30 aryl group, a C6 to C30 aryloxy group, or a C3 to C30 heteroaryl group,
$Y^1$ is O, S, Se, Te, S(=O), S(=O)₂, $NR^{a1}$, $SiR^{b1}R^{c1}$, or $GeR^{d1}R^{e1}$, wherein $R^{a1}$, $R^{b1}$, $R^{c1}$, $R^{d1}$, and $R^{e1}$ are independently hydrogen, a C1 to C10 alkyl group, a C1 to C10 haloalkyl group, a C1 to C10 alkoxy group, —SiH₃, a C1 to C10 alkylsilyl group, —NH₃, a C1 to C10 alkylamine group, a C6 to C10 arylamine group, a C6 to C14 aryl group, a C6 to C14 aryloxy group, a C3 to C12 heteroaryl group, a halogen, a cyano group, or a combination thereof,
$Y^2$ and $Y^3$ are independently O, S, Se, Te, S(=O), S(=O)₂, $NR^{a2}$, $SiR^{b2}R^{c2}$, $GeR^{d2}R^{e2}$, or $CR^{f2}R^{g2}$, wherein $R^{a2}$, $R^{b2}$, $R^{c2}$, $R^{d2}$, $R^{e2}$, $R^{f2}$, and $R^{g2}$ are independently hydrogen, a C1 to C10 alkyl group, a C1 to C10 haloalkyl group, a C1 to C10 alkoxy group, —SiH₃, a C1 to C10 alkylsilyl group, —NH₃, a C1 to C10 alkylamine group, a C6 to C10 arylamine group, a C6 to C14 aryl group, a C6 to C14 aryloxy group, a C3 to C12 heteroaryl group, a halogen, a cyano group, or a combination thereof, $R^{b1}$ and $R^{c1}$, $R^{d1}$ and $R^{e1}$, $R^{b2}$ and $R^{c2}$, $R^{d2}$ and $R^{e2}$, and $R^{f2}$ and $R^{g2}$ are independently present or combined with each other to form a spiro ring, an * outside the at least one aromatic ring is a linking point with Ar of Chemical Formula 1, and

*'s inside the at least one aromatic ring are linking portions with an $N(R^1)$— containing ring that includes $R^1$ of Chemical Formula 1 and an $N(R^2)$-containing ring that includes $R^2$ of Chemical Formula 1.

35. The photoelectric device of claim 19, wherein the active layer further includes fullerene or a fullerene derivative.

36. The photoelectric device of claim 19, wherein the active layer has a peak absorption wavelength in a wavelength region of about 750 nm to about 3000 nm.

37. An organic sensor comprising the photoelectric device of claim 19.

38. An electronic device comprising the organic sensor of claim 37.

39. An electronic device comprising the photoelectric device of claim 19.

40. A photoelectric device, comprising:
a first electrode and a second electrode facing each other;
an active layer between the first electrode and the second electrode; and
a charge auxiliary layer between
the active layer and the first electrode, or
the active layer and the second electrode,
wherein the charge auxiliary layer includes the near-infrared absorber of claim 1.

41. The photoelectric device of claim 36, wherein the active layer further includes the near-infrared absorber.

42. An organic sensor, comprising:
a semiconductor substrate;
a first photoelectric device on the semiconductor substrate, the first photoelectric device configured to selectively absorb light in a first near-infrared wavelength region; and
an additional sensor configured to selectively absorb light in a separate wavelength region that is different from the first near-infrared wavelength region,
wherein the first photoelectric device includes a near-infrared absorber that includes a compound represented by Chemical Formula 1:

[Chemical Formula 1]

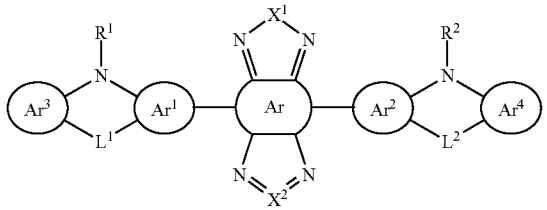

wherein, in Chemical Formula 1,
Ar is a substituted or unsubstituted C6 to C30 aromatic ring, a substituted or unsubstituted C3 to C30 heteroaromatic ring, or a combination thereof, $X^1$ is O, S, Se, Te, S(=O), S(=$O_2$), $NR^a$, $CR^bR^c$, $SiR^dR^e$, $GeR^fR^g$, $CR^h$=$CR^i$, or $CR^{hh}$=$CR^{ii}$, wherein $R^a$, $R^b$, $R^c$, $R^d$, $R^e$, $R^f$, $R^g$, $R^h$, and $R^i$ are independently hydrogen, deuterium, a C1 to C30 alkyl group, a C1 to C30 haloalkyl group, a C6 to C30 aryl group, a C6 to C30 aryloxy group, a C3 to C30 heteroaryl group, a halogen, a cyano group, or a combination thereof, $R^{hh}$ and $R^{ii}$ are independently (CH), where w is a positive integer or at least one heteroatom of O, N, S, Se, or Te, and $R^{hh}$ and $R^{ii}$ are linked to each other to form an aromatic ring or a heteroaromatic ring, $X^2$ is O, S, Se, Te, C, $CR^x$—$CR^y$, $CR^{xx}$—$CR^{yy}$, S(=O) or S(=$O_2$), wherein $R^x$ and $R^y$ are independently hydrogen, deuterium, a C1 to C30 alkyl group, a C1 to C30 haloalkyl group, a C6 to C30 aryl group, a C6 to C30 aryloxy group, a C3 to C30 heteroaryl group, a halogen, a cyano group, or a combination thereof, $R^{xx}$ and $R^{yy}$ are independently (CH), where v is a positive integer or at least one heteroatom of O, N, S, Se, or Te, and $R^{xx}$ and $R^{yy}$ are linked to each other to form an aromatic ring or a heteroaromatic ring, $Ar^1$ and $Ar^2$ are independently a heteroarene group including at least one heteroatom of O, S, Se, or Te, $Ar^3$ and $Ar^4$ are independently a substituted or unsubstituted C6 to C30 arene group, a substituted or unsubstituted C3 to C30 heteroarene group, or a condensed ring group thereof, $R^1$ and $R^2$ are independently hydrogen, deuterium, a halogen, a cyano group, a nitro group, a hydroxyl group, a substituted or unsubstituted C1 to C10 alkyl group, a substituted or unsubstituted C1 to C10 alkoxy group, a substituted or unsubstituted C6 to C10 aryl group, or a substituted or unsubstituted C3 to C10 heteroaryl group, and $L^1$ and $L^2$ are independently a single bond, —O—, —S—, —Se—, —Te—, —N=, —$NR^a$—, —$SiR^bR^c$—, —$GeR^dR^e$—, —$(CR^fR^g)_n$—, or —$(C(R^h)=C(R^i))$—, wherein $R^a$, $R^b$, $R^c$, $R^d$, $R^e$, $R^f$, $R^g$, $R^h$, and $R^i$ are independently hydrogen, deuterium, a halogen, a cyano group, a substituted or unsubstituted C1 to C10 alkyl group, or a substituted or unsubstituted C6 to C10 aryl group, wherein $R^b$ and $R^c$, $R^d$ and $R^e$, $R^f$ and $R^g$, or $R^h$ and $R^i$ are independently present or are linked to each other to form a separate ring, and n of —$(CR^fR^g)_n$— is an integer of 1 or 2.

43. The organic sensor of claim 42, wherein
the additional sensor is an infrared light sensor at least partially embedded within the semiconductor substrate, and the separate wavelength region is a separate near-infrared wavelength region that is different from the first near-infrared wavelength region, and
the first photoelectric device and the infrared light sensor overlap in a vertical direction that is perpendicular to a top surface of the semiconductor substrate.

44. The organic sensor of claim 42, wherein
the additional sensor includes a plurality of photodiodes at least partially embedded within the semiconductor substrate, the plurality of photodiodes configured to selectively absorb light in separate visible wavelength regions, and
the first photoelectric device and the plurality of photodiodes overlap in a vertical direction that is perpendicular to a top surface of the semiconductor substrate.

45. The organic sensor of claim 44, further comprising:
an additional photoelectric device on the semiconductor substrate, the additional photoelectric device being between the first photoelectric device and the semiconductor substrate, the additional photoelectric device configured to selectively absorb light in an additional wavelength region that is different from the first near-infrared wavelength region and the separate visible wavelength regions.

46. The organic sensor of claim 42, wherein
the additional sensor includes at least one additional photoelectric device vertically stacked between the first photoelectric device and the semiconductor substrate, each separate photoelectric device of the at least one additional photoelectric device including a separate photoelectric conversion layer and configured to selectively absorb light in a separate, respective wavelength region that is different from the first near-infrared wavelength region.

47. The organic sensor of claim 42, wherein the first photoelectric device includes
a first electrode and a second electrode facing each other; and
an active layer between the first electrode and the second electrode, wherein the active layer includes the near-infrared absorber.

48. The organic sensor of claim 42, wherein the first photoelectric device includes
a first electrode and a second electrode facing each other;
an active layer between the first electrode and the second electrode; and
a charge auxiliary layer between
the active layer and the first electrode, or
the active layer and the second electrode,
wherein the charge auxiliary layer includes the near-infrared absorber.

* * * * *